United States Patent
Jackson et al.

(10) Patent No.: US 7,189,569 B2
(45) Date of Patent: Mar. 13, 2007

(54) MODULATION OF CELL DIVISION BY AN EARLY MITOTIC INHIBITOR PROTEIN

(75) Inventors: Peter K. Jackson, Stanford, CA (US); Julie Regan Reimann, Menlo Park, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 582 days.

(21) Appl. No.: 10/155,789

(22) Filed: May 24, 2002

(65) Prior Publication Data

US 2003/0022837 A1    Jan. 30, 2003

Related U.S. Application Data

(60) Provisional application No. 60/293,921, filed on May 24, 2001.

(51) Int. Cl.
*A61K 48/00*    (2006.01)

(52) U.S. Cl. .......................................... 435/455; 514/44

(58) Field of Classification Search ............. 424/184.1; 435/4; 514/44
See application file for complete search history.

(56) References Cited

U.S. PATENT DOCUMENTS 5,948,639 A * 9/1999 Gimeno et al. ............ 435/69.1
6,720,181 B1 * 4/2004 Chiaur et al. ................ 435/325

FOREIGN PATENT DOCUMENTS

WO    WO 00/12679    3/2000

OTHER PUBLICATIONS

Reimann et al. (Molecular Biology of the Cell, Annual Meeting American Society Cell Biology, Dec. 2000, vol. 11, Supplement, pp. 7a).*
Craig et al., Progress in Biophys. & Molecul. Biol., (1999), 72: 299-328.
Reimann et al., Genes & Development, (2001), 15: 3278-3285.
Tyers et al., Current Opinion in Genetics, (2000), 10: 54-64.
Cenciarelli et al., Current Biology, (1999), 9: 1177-1179.
Hsu et al., Mol. Biol. Of Cell, (2000), vol. VII, Supplement, p. 448a.
Jackson et al., The Lore of the Rings: Substrate Recognition and Catalysis by Ubiquitin Ligases, Trends Cell. Biol., (2000), 10 (10): 429-39.
Page et al., The Anaphase-Promoting Complex: New Subunits and Regulators, Annue. Rev. Biochem., (1999), 68:583-609.
Zachariae et al., Whose End is Destruction: Cell Division and the Anaphase-Promoting Complex, Genes. Dev., (1999), 13 (16): 2039-58.

* cited by examiner

*Primary Examiner*—Misook Yu
(74) *Attorney, Agent, or Firm*—Pamela J. Sherwood; Bozicevic, Field & Francis LLP

(57) ABSTRACT

Emi1 regulates progression through early mitosis by preventing premature APC activation. Depleting Emi1 from cycling cells strongly delays cyclin B accumulation and mitotic entry, while expression of a stabilized form of Emi1 stabilizes APC substrates and causes a mitotic block. Emi1 binds the APC activators Cdc2O and Cdh1 and inhibits APC activation by Cdc20 or Cdh1. Hence, products that modulate the expression and/or activity of Emi1 have a therapeutic effect in the treatment of cancer, leukemia, solid tumors, chronic or acute inflammatory disease, restenosis, diabetes, neurological disorders, arthritis and osteoporosis, among other indications.

4 Claims, 21 Drawing Sheets

FIG. 1A

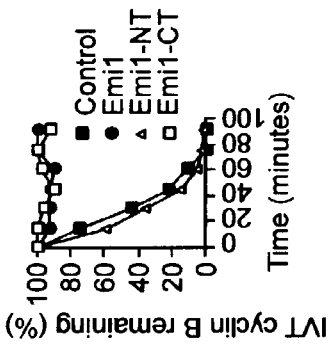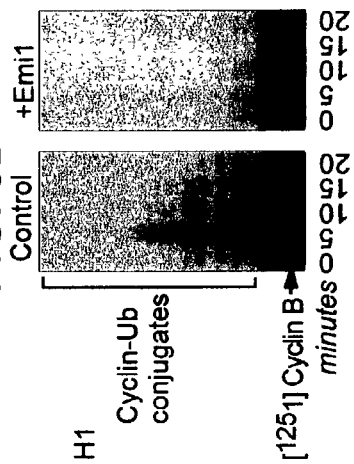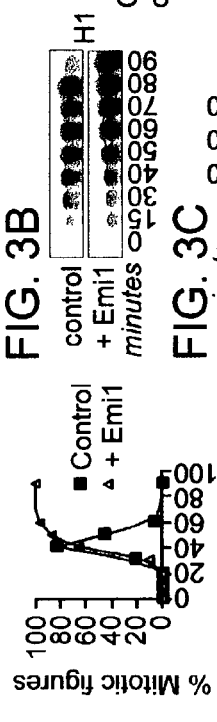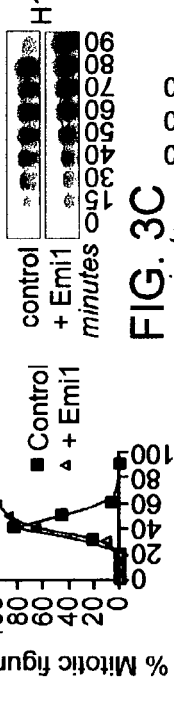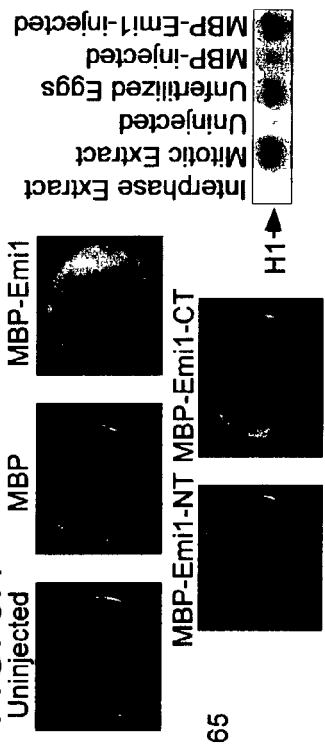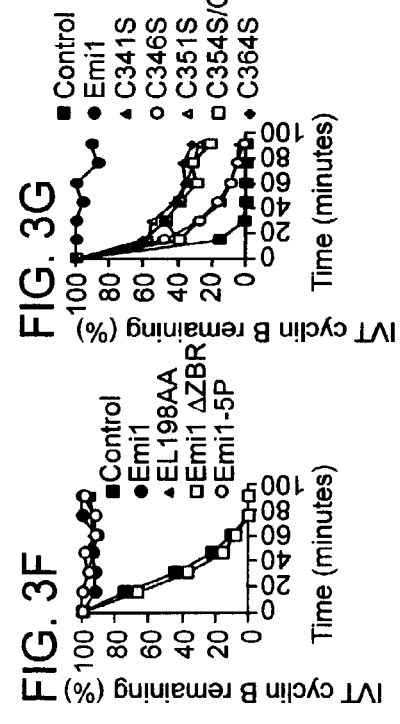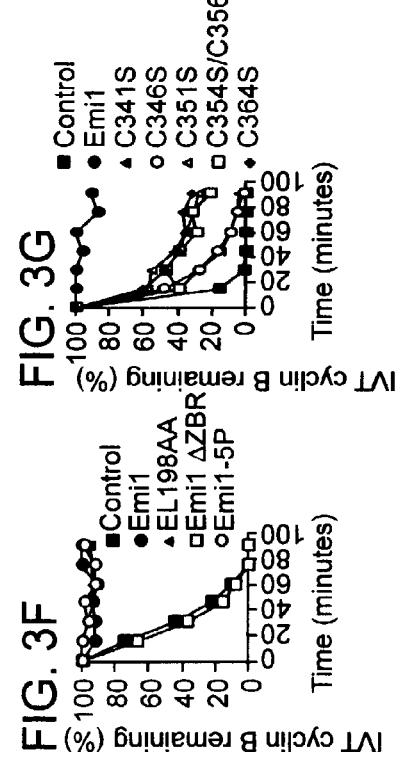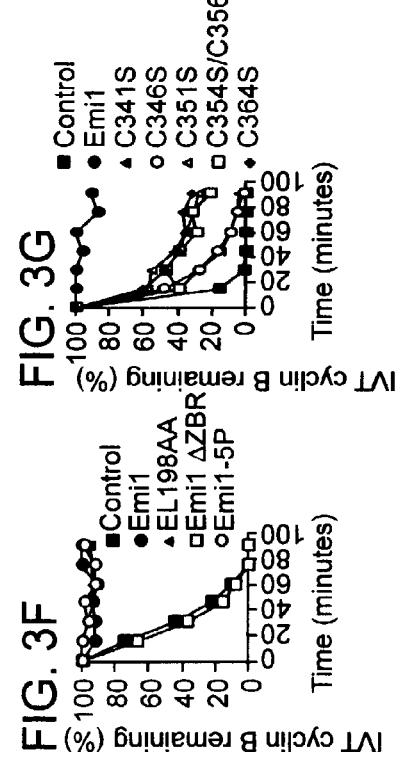

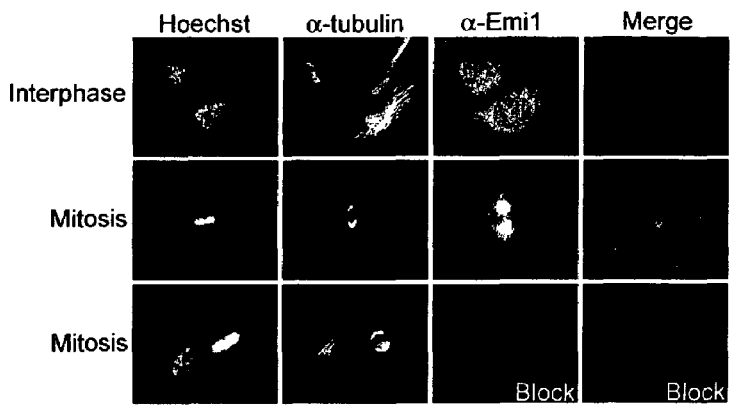
FIG. 4A
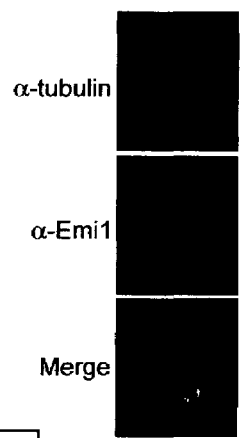
FIG. 4B
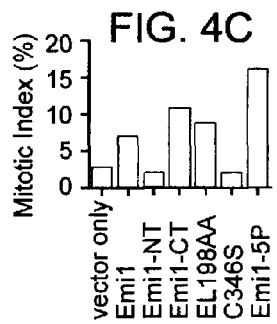
FIG. 4C
| Protein | G₀/G₁ | S | G₂/M |
|---|---|---|---|
| vector | 68.3 | 26.5 | 5.2 |
| Emi1 | 56 | 30.7 | 13.3 |
| Emi1-NT | 67.6 | 23.8 | 8.6 |
| Emi1-CT | 45.9 | 31.6 | 22.5 |
| Emi1ΔZBR | 63.1 | 27.2 | 9.7 |
| C346S | 54.4 | 33.2 | 12.4 |
| EL198AA | 48.8 | 26.9 | 24.3 |
| Emi1-5P | 52.2 | 31 | *16.8 |
FIG. 4D
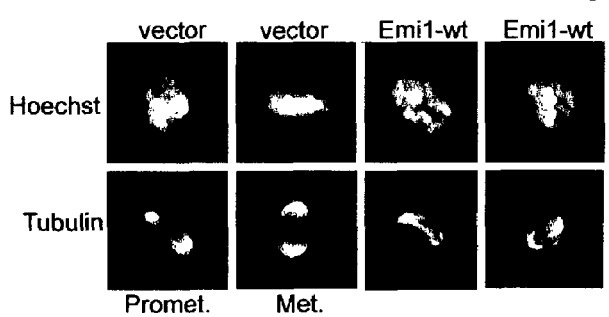
FIG. 4E
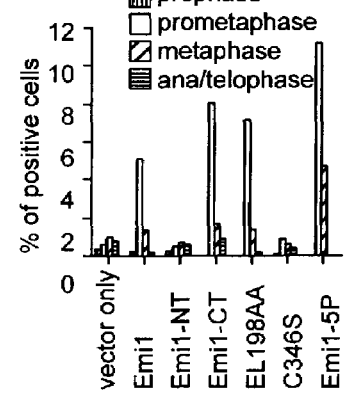
FIG. 4F

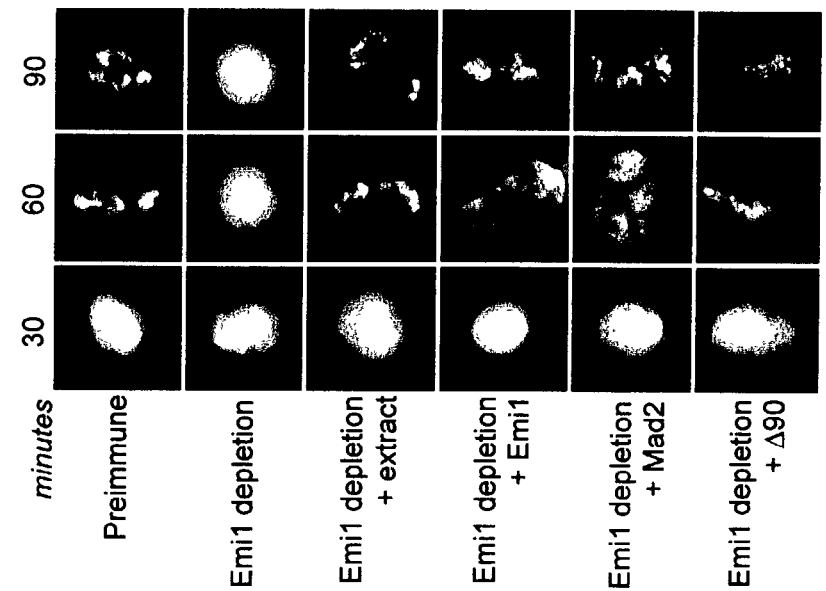
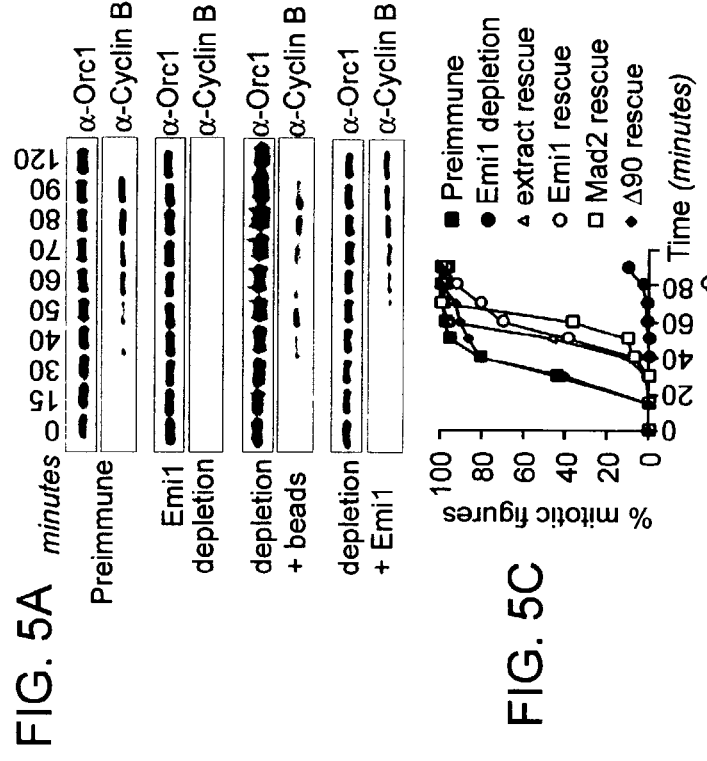

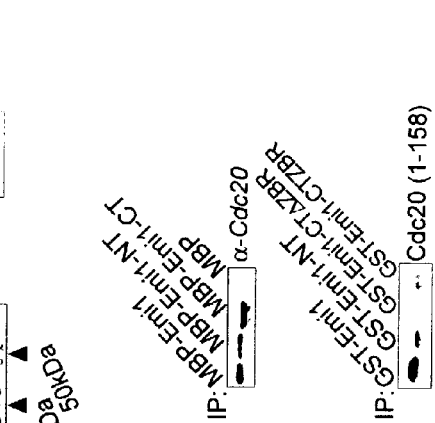
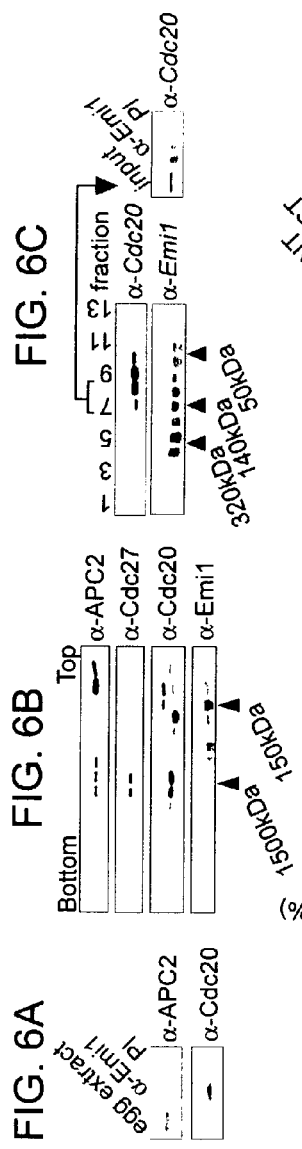
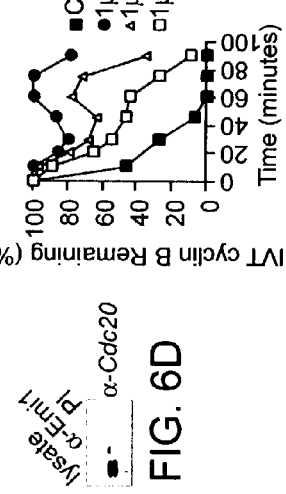
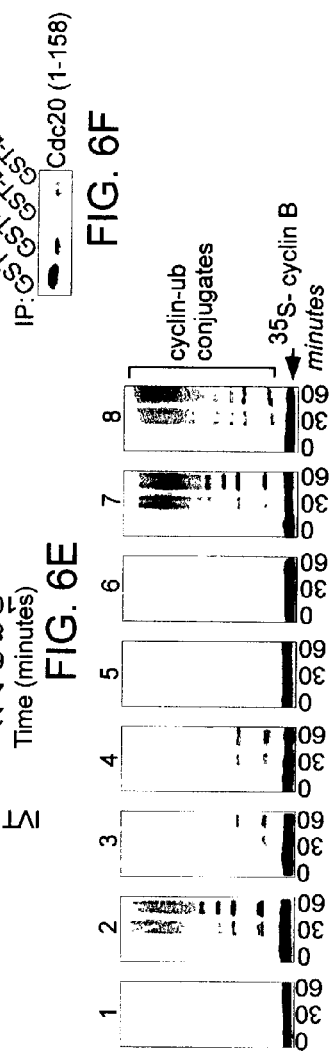
FIG. 6A  FIG. 6B  FIG. 6C  FIG. 6D  FIG. 6E  FIG. 6F  FIG. 6G

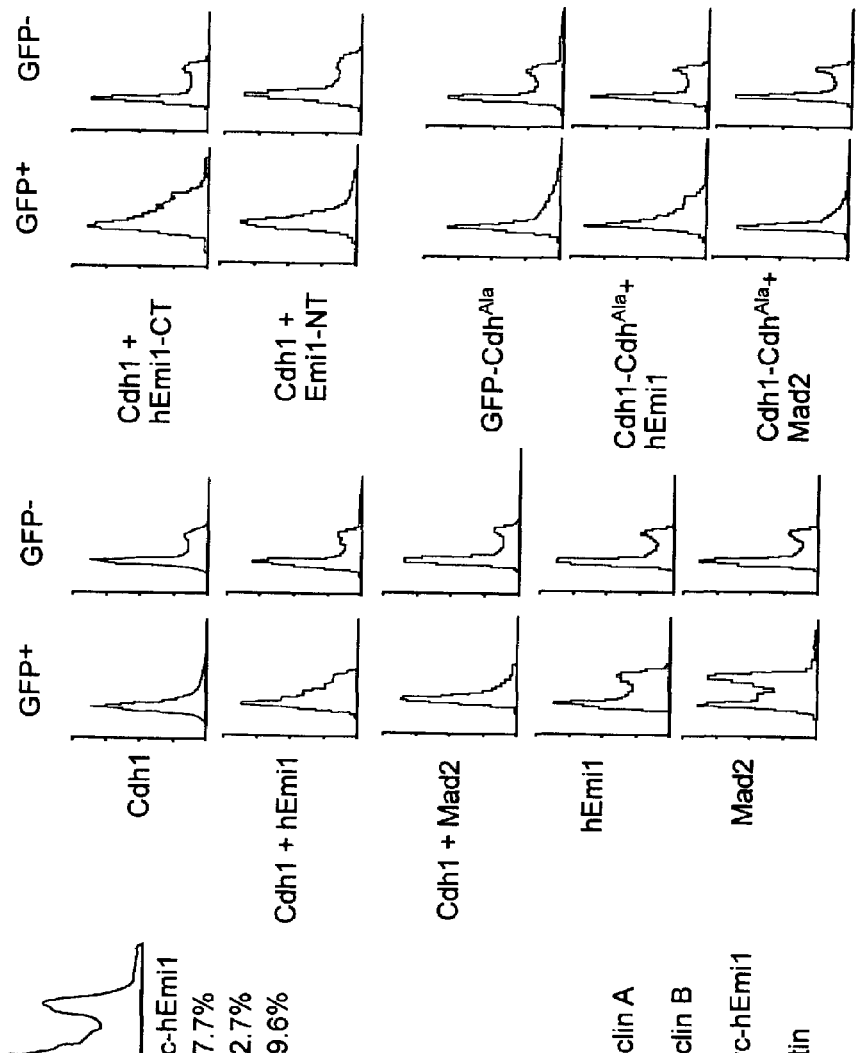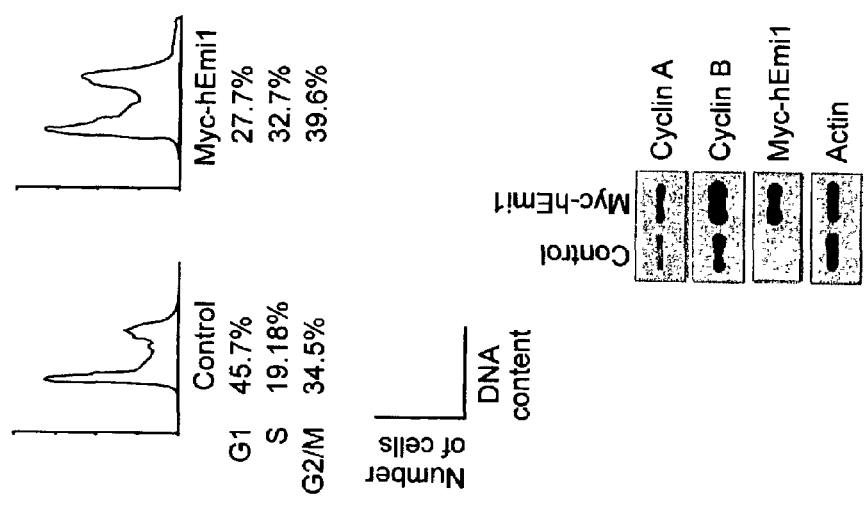

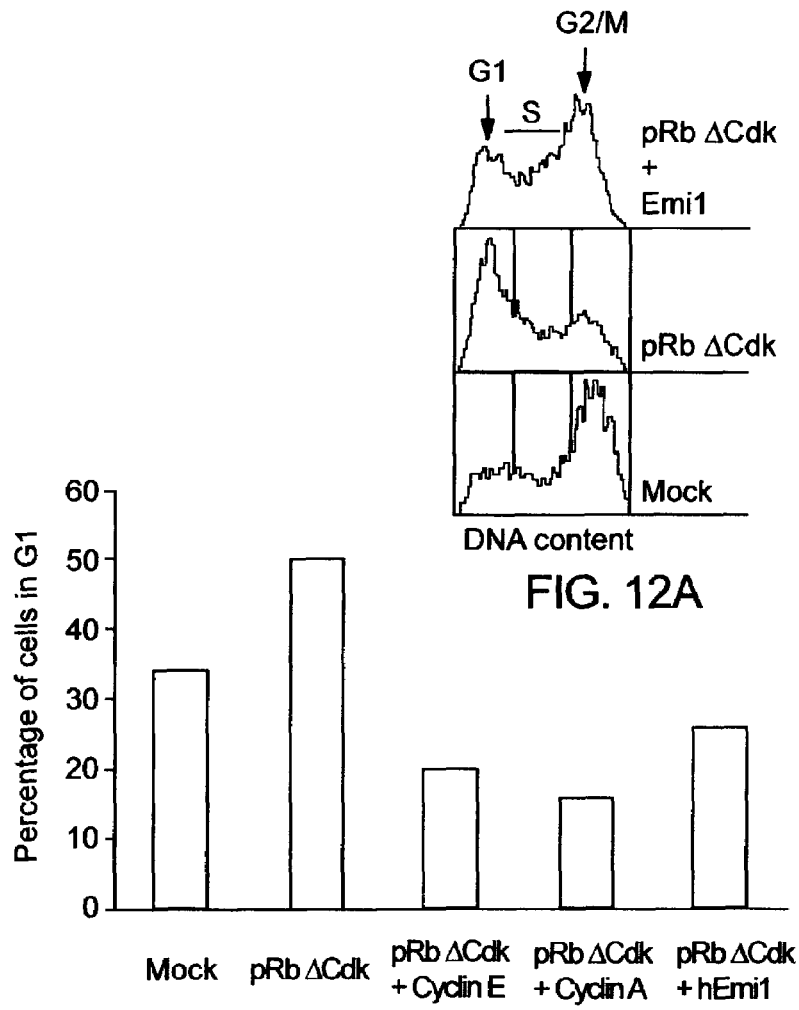
FIG. 12A
FIG. 12B
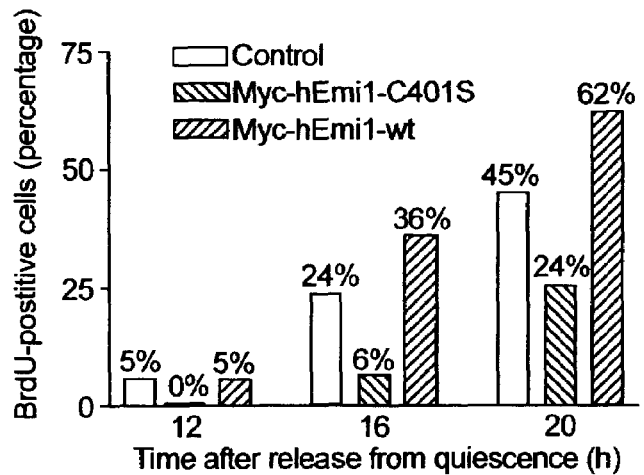
FIG. 12C

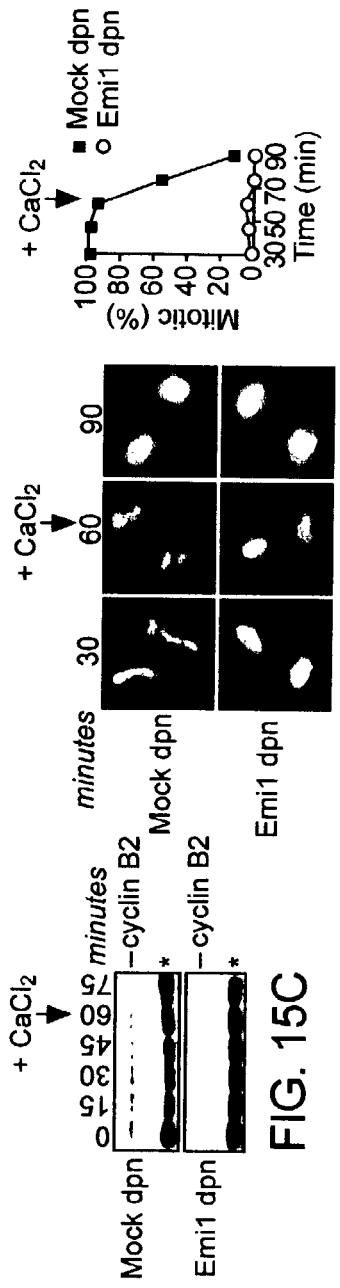

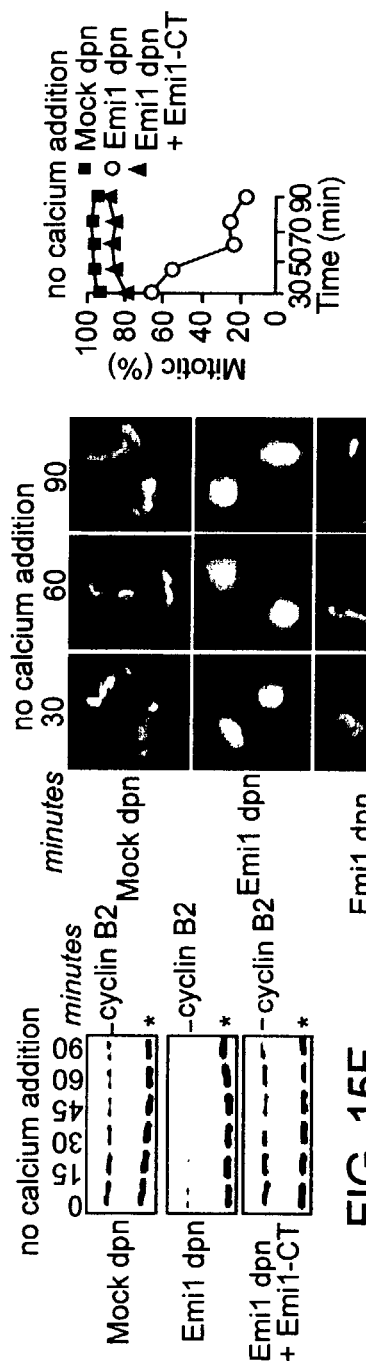

FIG. 16A
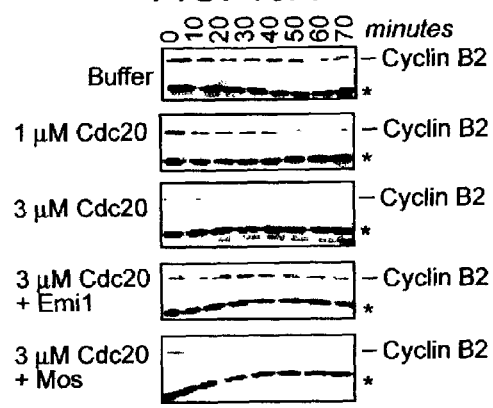
FIG. 16B
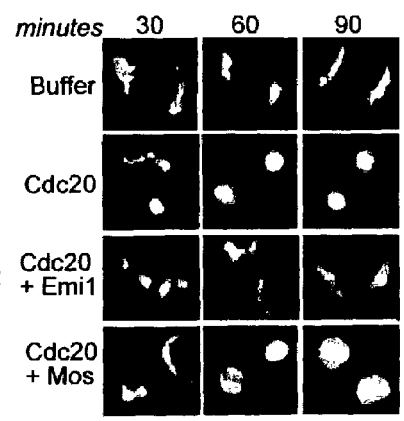
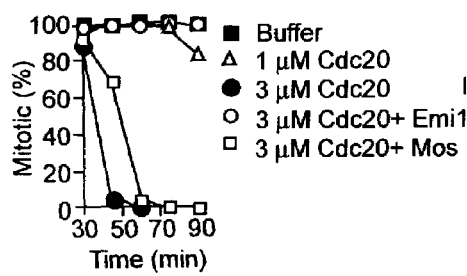
FIG. 16C
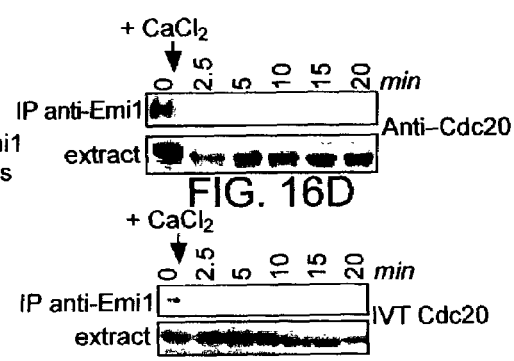
FIG. 16D
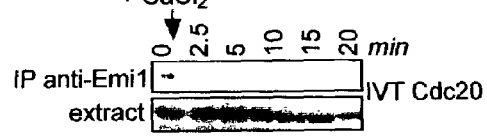
FIG. 16E

SEQUENCE LISTING

<160> NUMBER OF SEQ ID NOS: 18

<210> SEQ ID NO 1
<211> LENGTH: 1883
<212> TYPE: DNA
<213> ORGANISM: Xenopus laevis

<400> SEQUENCE: 1

```
tgagattgtg ggtgttttta acaggctagg gggaataacg aaagcgggag ctatgcggga      60
ggagtgttat ggaaaaatca gatcgctttt aaacaccgta ttcttttttt aatttttttg     120
gtaaatgatc ttgagaagtg ggcgcttcgg aaaagcgtga tattttatcc agaatacagg     180
tttcagccta tcgggtcctg acctacctat caatatgatg tgcggatttg caagtaacca     240
gtctccaaaa aagctatctt caaaaaaatc aagtgcaact aatgttcact tagaaattag     300
tccagtgaag catcaccctc catgcaaagt ctatgaaaat gtgcaaggct cctgcttgga     360
```

```
tagtgcaatc tgcacaacag ttgcaaagtg tgcagacctt acagatgatc tgcctgtaca        420
caacaaggag aatcttttgc atagacttaa tgatttagaa acaaacagtt atgaagaata        480
tagtgcattg caagatagtg gttattcgtc aatactgcaa aatgactctc catgtcaaga        540
tgaaacagac cggaaagttt cagatattca agtacgtgaa acaccaaaga atttcatgtc        600
ataccaaaga cccttccata ctttatctaa aataaatttg ccgatccttc gttttgaaga        660
agctgtttgt tctacgctga agaaaatgag aaaaacaaac aaaaaaattg actggaatgc        720
tgttgatgtc gtttgtggtg gaaactatgg acttgagcat ctgattggca aaagtatggg        780
actggaaaga ttcgatatac ttgcagaact ttttccatcga gatttcaagc atttgctgac        840
taaaatttta aggcacctta gtgcaatgga tttaataaat gtcatcagtg tgagcacaac        900
atggagaaaa ctgctgcaga aagataactg ggcctacaat gcttataaat taggatgcaa        960
ggagctttgt gaaagagag ccaaagtatc cagccacact gcaacccgtg atgagtctct       1020
ctgccgtgtg cctttagcat ctgttcaaaa agtagcagcg tcctctctct gcacatcaaa       1080
aaaacagagc aagaataaaa atggaggcct gtcttgtaac agacttgcag aatttattga       1140
ggttgctcaa actttaaaga atgaccaaag ccttaaggtt tgtgtagact gtggctcccc       1200
agctaaacat gacccttgcc ttcatcgagc catctgcaca agagagagct gtaaattgga       1260
cttttgcacc cgttgctctt gtaaatatca cttttcaaaa agctgcctga tgagtaagcc       1320
agggagttat cgaattcctt cagagccatt gcccgggagc aaaaaaagca acagaatttt       1380
acggaggtta tagtttaaaa ttaatttaaa tcctgttttg ggtatattca aaagtgtcta       1440
tacgtatttt aatatatgtg tatgtgtgtg tgtgtgcgcc atcatctacg ttttagtatt       1500
ttaatggagc atttgtttta ttaattttct tactcttaat gttaaaatag gagtcttgtt       1560
taaaaatcaa attgtttctt cgtaggtaca atatatttta tatttccaaa acaagatttg       1620
gcatttatca tgtatatcta tatgaaatat atatatatat atatatatat atatatatat       1680
atttgatctc ttataaggga tcactgcttt tctaattggg gaaaaatgta ttttctaaat       1740
actgtatata tttgcatttt tgcgcaaagt tttgtaaata tgttcattta tatgtgctct       1800
atggttcgct ctgtgtgcag tatatttttc tgtgctaaat aaattattgc aatttcatag       1860
ctgtaaaaaa aaaaaaaaaa aaa                                               1883
```

<210> SEQ ID NO 2
<211> LENGTH: 392
<212> TYPE: PRT
<213> ORGANISM: Xenopus laevis

<400> SEQUENCE: 2

```
Met Met Cys Gly Phe Ala Ser Asn Gln Ser Pro Lys Lys Leu Ser Ser
  1               5                  10                  15

Lys Lys Ser Ser Ala Thr Asn Val His Leu Glu Ile Ser Pro Val Lys
             20                  25                  30

His His Pro Pro Cys Lys Val Tyr Glu Asn Val Gln Gly Ser Cys Leu
         35                  40                  45

Asp Ser Ala Ile Cys Thr Thr Val Ala Lys Cys Ala Asp Leu Thr Asp
     50                  55                  60

Asp Leu Pro Val His Asn Lys Glu Asn Leu Leu His Arg Leu Asn Asp
 65                  70                  75                  80

Leu Glu Thr Asn Ser Tyr Glu Glu Tyr Ser Ala Leu Gln Asp Ser Gly
                 85                  90                  95

Tyr Ser Ser Ile Leu Gln Asn Asp Ser Pro Cys Gln Asp Glu Thr Asp
```

-continued

```
                100                 105                 110
Arg Lys Val Ser Asp Ile Gln Val Arg Glu Thr Pro Lys Asn Phe Met
            115                 120                 125
Ser Tyr Gln Arg Pro Phe His Thr Leu Ser Lys Ile Asn Leu Pro Ile
        130                 135                 140
Leu Arg Phe Glu Glu Ala Val Cys Ser Thr Leu Lys Lys Met Arg Lys
145                 150                 155                 160
Thr Asn Lys Lys Ile Asp Trp Asn Ala Val Asp Val Cys Gly Gly
                165                 170                 175
Asn Tyr Gly Leu Glu His Leu Ile Gly Lys Ser Met Gly Leu Glu Arg
            180                 185                 190
Phe Asp Ile Leu Ala Glu Leu Phe His Arg Asp Phe Lys His Leu Leu
        195                 200                 205
Thr Lys Ile Leu Arg His Leu Ser Ala Met Asp Leu Ile Asn Val Ile
    210                 215                 220
Ser Val Ser Thr Thr Trp Arg Lys Leu Leu Gln Lys Asp Asn Trp Ala
225                 230                 235                 240
Tyr Asn Ala Tyr Lys Leu Gly Cys Lys Glu Leu Cys Glu Lys Arg Ala
                245                 250                 255
Lys Val Ser Ser His Thr Ala Thr Arg Asp Glu Ser Leu Cys Arg Val
            260                 265                 270
Pro Leu Ala Ser Val Gln Lys Val Ala Ala Ser Ser Leu Cys Thr Ser
        275                 280                 285
Lys Lys Gln Ser Lys Asn Lys Asn Gly Gly Leu Ser Cys Asn Arg Leu
    290                 295                 300
Ala Glu Phe Ile Glu Val Ala Gln Thr Leu Lys Asn Asp Gln Ser Leu
305                 310                 315                 320
Lys Val Cys Val Asp Cys Gly Ser Pro Ala Lys His Asp Pro Cys Leu
                325                 330                 335
His Arg Ala Ile Cys Thr Arg Glu Ser Cys Lys Leu Asp Phe Cys Thr
            340                 345                 350
Arg Cys Ser Cys Lys Tyr His Phe Ser Lys Ser Cys Leu Met Ser Lys
        355                 360                 365
Pro Gly Ser Tyr Arg Ile Pro Ser Glu Pro Leu Pro Gly Ser Lys Lys
    370                 375                 380
Ser Lys Gln Asn Leu Arg Arg Leu
385                 390

<210> SEQ ID NO 3
<211> LENGTH: 2045
<212> TYPE: DNA
<213> ORGANISM: Homo sapiens

<400> SEQUENCE: 3
aggttgctca gctgccccg gagcggttcc tccacctgag gcagactcca cgtcggctgg    60
catgagccgg cgcccctgca gctgcgccct acggccaccc cgctgctcct gcagcgccag   120
ccccagcgca gtgacagccg ccgggcgccc tcgaccctcg gatagttgta aagaagaaag   180
ttctacccct tctgtcaaaa tgaagtgtga ttttaattgt aaccatgttc attccggact   240
taaactggta aaacctgatg acattggaag actagtttcc tacacccctg catatttgga   300
aggttcctgt aaagactgca ttaaagacta tgaaaggctg tcatgtattg ggtcaccgat   360
tgtgagccct aggattgtac aacttgaaac tgaaagcaag cgcttgcata caaggaaaa   420 tcaacatgtg caacagacac ttaatagtac aaatgaaata gaagcactag agaccagtag   480
```

-continued

```
actttatgaa gacagtggct attcctcatt ttctctacaa agtggcctca gtgaacatga    540
agaaggtagc ctcctggagg agaatttcgg tgacagtcta caatcctgcc tgctacaaat    600
acaaagccca gaccaatatc ccaacaaaaa cttgctgcca gttcttcatt ttgaaaaagt    660
ggtttgttca acattaaaaa agaatgcaaa acgaaatcct aaagtagatc gggagatgct    720
gaaggaaatt atagccagag gaatttttag actgcagaat ataattggca gaaaaatggg    780
cctagaatgt gtagatattc tcagcgaact ctttcgaagg ggactcagac atgtcttagc    840
aactatttta gcacaactca gtgacatgga cttaatcaat gtgtctaaag tgagcacaac    900
ttggaagaag atcctagaag atgataaggg ggcattccag ttgtacagta aagcaataca    960
aagagttacc gaaacaacaa taaattttc acctcatgct tcaaccagag aatatgttat    1020
gttcagaacc ccactggctt ctgttcagaa atcagcagcc cagacttctc tcaaaaaaga   1080
tgctcaaacc aagttatcca atcaaggtga tcagaaaggt tctacttata gtcgacacaa   1140
tgaattctct gaggttgcca agacattgaa aaagaacgaa agcctcaaag cctgtattcg   1200
ctgtaattca cctgcaaaat atgattgcta tttacaacgg gcaacctgca acgagaagg    1260 ctgtggattt gattattgta cgaagtgtct ctgtaattat catactacta aagactgttc   1320
agatggcaag ctcctcaaag ccagttgtaa aataggtccc ctgcctggta caaagaaaag   1380
caaaaagaat ttacgaagat gtgatctct tattaaatca attgttactg atcatgaatg    1440
ttagttagaa aatgttaggt tttaacttaa aaaaaattgt attgtgattt tcaattttat   1500
gttgaaatcg gtgtagtatc ctgaggtttt ttccccccca gaagataaag aggatagaca   1560
acctcttaaa atatttttac aatttaatga gaaaagttt aaaattctca atacaaatca    1620
aacaatttaa atattttaag aaaaaaggaa agtagatag tgatactgag ggtaaaaaaa    1680
aattgattca atttatggt aaaggaaacc catgcaattt tacctagaca gtcttaaata    1740
tgtctggttt tccatctgtt agcatttcag acatttatg ttcctcttac tcaattgata   1800
ccaacagaaa tatcaacttc tggagtctat taaatgtgtt gtcaccttc taaagctttt    1860 tttcattgtg tgtatttccc aagaaagtat cctttgtaaa aacttgcttg ttttccttat   1920
ttctgaaatc tgttttaata tttttgtata catgtaaata tttctgtatt ttttatatgt   1980
caaagaatat gtctcttgta tgtacatata aaataaaatt ttgctcaata aaattgtaag   2040
cttaa                                                              2045
```

<210> SEQ ID NO 4
<211> LENGTH: 447
<212> TYPE: PRT
<213> ORGANISM: Homo sapiens

<400> SEQUENCE: 4

```
Met Ser Arg Arg Pro Cys Ser Cys Ala Leu Arg Pro Pro Arg Cys Ser
 1               5                  10                  15

Cys Ser Ala Ser Pro Ser Ala Val Thr Ala Ala Gly Arg Pro Arg Pro
                20                  25                  30

Ser Asp Ser Cys Lys Glu Glu Ser Thr Leu Ser Val Lys Met Lys
            35                  40                  45

Cys Asp Phe Asn Cys Asn His Val His Ser Gly Leu Lys Leu Val Lys
        50                  55                  60

Pro Asp Asp Ile Gly Arg Leu Val Ser Tyr Thr Pro Ala Tyr Leu Glu
    65                  70                  75                  80

Gly Ser Cys Lys Asp Cys Ile Lys Asp Tyr Glu Arg Leu Ser Cys Ile
```

-continued

```
                85                  90                  95
Gly Ser Pro Ile Val Ser Pro Arg Ile Val Gln Leu Glu Thr Glu Ser
            100                 105                 110
Lys Arg Leu His Asn Lys Glu Asn Gln His Val Gln Gln Thr Leu Asn
        115                 120                 125
Ser Thr Asn Glu Ile Glu Ala Leu Glu Thr Ser Arg Leu Tyr Glu Asp
    130                 135                 140
Ser Gly Tyr Ser Ser Phe Ser Leu Gln Ser Gly Leu Ser Glu His Glu
145                 150                 155                 160
Glu Gly Ser Leu Leu Glu Glu Asn Phe Gly Asp Ser Leu Gln Ser Cys
                165                 170                 175
Leu Leu Gln Ile Gln Ser Pro Asp Gln Tyr Pro Asn Lys Asn Leu Leu
            180                 185                 190
Pro Val Leu His Phe Glu Lys Val Val Cys Ser Thr Leu Lys Lys Asn
        195                 200                 205
Ala Lys Arg Asn Pro Lys Val Asp Arg Glu Met Leu Lys Glu Ile Ile
    210                 215                 220
Ala Arg Gly Asn Phe Arg Leu Gln Asn Ile Ile Gly Arg Lys Met Gly
225                 230                 235                 240
Leu Glu Cys Val Asp Ile Leu Ser Glu Leu Phe Arg Arg Gly Leu Arg
                245                 250                 255
His Val Leu Ala Thr Ile Leu Ala Gln Leu Ser Asp Met Asp Leu Ile
            260                 265                 270
Asn Val Ser Lys Val Ser Thr Thr Trp Lys Lys Ile Leu Glu Asp Asp
        275                 280                 285
Lys Gly Ala Phe Gln Leu Tyr Ser Lys Ala Ile Gln Arg Val Thr Glu
    290                 295                 300
Asn Asn Asn Lys Phe Ser Pro His Ala Ser Thr Arg Glu Tyr Val Met
305                 310                 315                 320
Phe Arg Thr Pro Leu Ala Ser Val Gln Lys Ser Ala Ala Gln Thr Ser
                325                 330                 335
Leu Lys Lys Asp Ala Gln Thr Lys Leu Ser Asn Gln Gly Asp Gln Lys
            340                 345                 350
Gly Ser Thr Tyr Ser Arg His Asn Glu Phe Ser Glu Val Ala Lys Thr
        355                 360                 365
Leu Lys Lys Asn Glu Ser Leu Lys Ala Cys Ile Arg Cys Asn Ser Pro
    370                 375                 380
Ala Lys Tyr Asp Cys Tyr Leu Gln Arg Ala Thr Cys Lys Arg Glu Gly
385                 390                 395                 400
Cys Gly Phe Asp Tyr Cys Thr Lys Cys Leu Cys Asn Tyr His Thr Thr
                405                 410                 415
Lys Asp Cys Ser Asp Gly Lys Leu Leu Lys Ala Ser Cys Lys Ile Gly
            420                 425                 430
Pro Leu Pro Gly Thr Lys Lys Ser Lys Lys Asn Leu Arg Arg Leu
        435                 440                 445
```

<210> SEQ ID NO 5
<211> LENGTH: 1421
<212> TYPE: DNA
<213> ORGANISM: Mus musculus
<220> FEATURE:
<221> NAME/KEY: misc_feature
<222> LOCATION: (1)...(1421)
<223> OTHER INFORMATION: n = A,T,C or G

<400> SEQUENCE: 5

```
gaaaatcaaa gatttaaaag tcacgntggc gccttttaag agctgcggct cggcgcctcg      60
tctggccggc caccttttc ctgtcgtcgc cgccacctcc ccagcattgg agcccgagtt     120
ttgcggcatg agccggcgca cctgcagtga cctgcgccgg ccgtcctcct gtccctgccg     180
tcttggcgcg cggactaccg tggacggttg taaagaagaa agccctgttc tttctgttac     240
aatgaagtgt tttaattgca accctgatct ttccgagctt gaagtggtga agcctgagga     300
cagtgggata gaagcttcct acagtcccgt gtgtttggaa ccttcctgta atgactgtgt     360
tagaaaccat gagaggttgt ctttcatcga ctcaccaatt gtgggacatg ataacaagga     420
aaatcaacgc gtacaaaaca cactagatag ttcaaacgaa acagaagagc tagaggccag     480
tagactgtat gaggacagtg gctactcatc tttcacacaa agtgaccgtg acgatggcat     540
ccttatcctg gagaatttca gaaacagtcc ccaggcccgt ctgctgccat cacagagccc     600
ggaccagcat cccaacaaaa ccttgctgcc tgtcctgcat tttgaaagag tggtttgctc     660
aacactaaaa aagaatggca agcgaaaccc taaagtggat cgagaaatgc tgaaggaagt     720
tattgccagc gagaacttta gactgcaaaa tataattggc aagaaaatgg gcctggagca     780
cctagacatc ctggctgagc tctcccgcag gggattcgtg cacctgttgg ctaacatttt     840
gactaagctc agcggcatgg acttagtaaa tctgtctaaa gtgagcagaa tttggaagaa     900
gatactggaa aacaataagg gggcgttcca gctctacagc aaaaccatgc agcgagtcat     960
tgaaagcagt aagttgtcac tacatgctac aacgagagga tatgttgtgg gcagagctgc    1020
actaacttgt gttcaaaagt catcgacctg ggcacctccc aaaaaagatg ttcaaatcaa    1080
gtcctccagt cagcgtggtc agagagtttc tacctacagc cggcacaatg agttcgtgga    1140
ggtggcaaag acattgaaga caacgaaag cctcaaagcc tgtgttcgct gtaatttccc    1200
tgcaaaatat gaccactatt tagagcgagc agtctgcaaa cgggaaagct gtcaatttga    1260
atattgtaca aagtgtctgt gtgcttacca taacaacaaa gactgtttga atggcaagat    1320
cctaaaagcc agctgtaaag tgggtccttt gcctggaact aaaaagagta aaagaacttt    1380
acaaagattg tgatagatca actgtagatc ttggctactt t                        1421
```

<210> SEQ ID NO 6
<211> LENGTH: 421
<212> TYPE: PRT
<213> ORGANISM: Mus musculus

<400> SEQUENCE: 6

```
Met Ser Arg Arg Thr Cys Ser Asp Leu Arg Arg Pro Ser Ser Cys Pro
  1               5                  10                  15

Cys Arg Leu Gly Ala Arg Thr Thr Val Asp Gly Cys Lys Glu Glu Ser
             20                  25                  30

Pro Val Leu Ser Val Thr Met Lys Cys Phe Asn Cys Asn Pro Asp Leu
         35                  40                  45

Ser Glu Leu Glu Val Val Lys Pro Glu Asp Ser Gly Ile Glu Ala Ser
     50                  55                  60

Tyr Ser Pro Val Cys Leu Glu Pro Ser Cys Asn Asp Cys Val Arg Asn
 65                  70                  75                  80

His Glu Arg Leu Ser Phe Ile Asp Ser Pro Ile Val Gly His Asp Asn
                 85                  90                  95

Lys Glu Asn Gln Arg Val Gln Asn Thr Leu Asp Ser Ser Asn Glu Thr
            100                 105                 110

Glu Glu Leu Glu Ala Ser Arg Leu Tyr Glu Asp Ser Gly Tyr Ser Ser
```

```
                115                 120                 125
Phe Thr Gln Ser Asp Arg Asp Gly Ile Leu Ile Leu Glu Asn Phe
        130                 135                 140
Arg Asn Ser Pro Gln Ala Arg Leu Leu Pro Ser Gln Ser Pro Asp Gln
145                 150                 155                 160
His Pro Asn Lys Thr Leu Leu Pro Val Leu His Phe Glu Arg Val Val
                165                 170                 175
Cys Ser Thr Leu Lys Lys Asn Gly Lys Arg Asn Pro Lys Val Asp Arg
                180                 185                 190
Glu Met Leu Lys Glu Val Ile Ala Ser Gly Asn Phe Arg Leu Gln Asn
                195                 200                 205
Ile Ile Gly Lys Lys Met Gly Leu Glu His Leu Asp Ile Leu Ala Glu
        210                 215                 220
Leu Ser Arg Arg Gly Phe Val His Leu Leu Ala Asn Ile Leu Thr Lys
225                 230                 235                 240
Leu Ser Gly Met Asp Leu Val Asn Leu Ser Lys Val Ser Arg Ile Trp
                245                 250                 255
Lys Lys Ile Leu Glu Asn Asn Lys Gly Ala Phe Gln Leu Tyr Ser Lys
        260                 265                 270
Thr Met Gln Arg Val Ile Glu Ser Ser Lys Leu Ser Leu His Ala Thr
        275                 280                 285
Thr Arg Gly Tyr Val Val Gly Arg Ala Ala Leu Thr Cys Val Gln Lys
        290                 295                 300
Ser Ser Thr Trp Ala Pro Pro Lys Lys Asp Val Gln Ile Lys Ser Ser
305                 310                 315                 320
Ser Gln Arg Gly Gln Arg Val Ser Thr Tyr Ser Arg His Asn Glu Phe
                325                 330                 335
Val Glu Val Ala Lys Thr Leu Lys Asn Asn Glu Ser Leu Lys Ala Cys
                340                 345                 350
Val Arg Cys Asn Phe Pro Ala Lys Tyr Asp His Tyr Leu Glu Arg Ala
        355                 360                 365
Val Cys Lys Arg Glu Ser Cys Gln Phe Glu Tyr Cys Thr Lys Cys Leu
        370                 375                 380
Cys Ala Tyr His Asn Asn Lys Asp Cys Leu Asn Gly Lys Ile Leu Lys
385                 390                 395                 400
Ala Ser Cys Lys Val Gly Pro Leu Pro Gly Thr Lys Lys Ser Lys Lys
                405                 410                 415
Asn Leu Gln Arg Leu
        420

<210> SEQ ID NO 7
<211> LENGTH: 1577
<212> TYPE: DNA
<213> ORGANISM: Drosophila melanogaster

<400> SEQUENCE: 7
agttagtatt ttatagggc ggtcacactg atccgtaccc aaaaacaatc aaccgatgcg      60
aaaagcataa caattcgaaa gtttaaaatt cggtcaagat gagcgcctat tatcggcgcg     120
cggcgttgcg gaagaagagc ccaagccgag ggtcatcctt cgagttggag atgaacgagt     180
ctggctacac atccttcctg gcgctgcaca attccaccgc ggagacgcca tttttattgg     240
aggacgctga gggcgaaaac tgtcgcaatg catcgaatac cacaacattc tttcgggggc     300
tgaacacgcc cagtggccac caggagcagg acctttactg gggcaagccc tatcccagaa     360
```

-continued

```
cacagcccca aaagaaattt tccgcggagg aggagccttt ctctatgact ccgcgtctgc      420
aggatgagca tagtctgccc aagcgacgca agaaacactt tcaatcgcca cacagtagcc      480
ccaagaagtc caaaaagctg ctctttcccc acatagaaga accgcccaag aatcgcttct      540
acggcggtgt cgaaaagctg gacatcgtgg ccaagctggc gcaatggcaa ccggcactgc      600
agtgcatact gcgtcatgtg ggcgcccaca cgctggacgt gatgaccaag gtatcgccgg      660
cctggaagca ggctgtttat cgcagccaac gcgacttgga gcgcctacag aaccaccgac      720
tcaaattgaa tctaaccaaa gagaatcctc acgtgcccaa gcggtgcagc catgtgccca      780
aggcaaacca cacagtgcca ttgcagacct cgaaccatag cagcctggcc aacagcgtcc      840
gcctcgctaa tggactcggg caactcgagc atccacctga tggacgtgga tgccggaagg      900
gtgctgcgcg acgagacgca tgctgcgtca agtgtccgcg atgcggtcga ggcagccggg      960
ttttcataag cgaggcggcc aagtgtggcg aaaacctatt gtcgcaaact ctgcctattg     1020
gacgtacaac cagcacattc ccctgcatga cgggtccgcc cctcaaacgc ttcctgtccc     1080
tggatcttga cgaggtcagg acttcaccgc aaggaccgcc atataacttc gccgaatgca     1140
ccagtgtcat ctgccagttt cggttctgcg tcaactgtct gtgcaagtcg catcccggcg     1200
agcgttgcct ggtcaccgaa ctggacacac catccaaatt gatgatgcca cgggagcgac     1260
tgacgccgcc acaacgtgcc cagaaccgtg atccgaaaat cacaaggaag aactcgctca     1320
agcggctctg tttttagctt tatcataggc ttttaactat tacgattagt attcgatttt     1380
ttcaaatctc attaatttcg tattatgtcc atcgcattaa gttccatttc atcacgtaca     1440
ttcatatata tgtttttaaa tcgttctatg taaggtttgt cggaattctg tacctctgcg     1500
agattaagta ttttttacac atgcaaaata tataaatcat ttttagaact ataaaaaaaa     1560
aaaaaaaaaa aaaaaa                                                     1577
```

<210> SEQ ID NO 8
<211> LENGTH: 412
<212> TYPE: PRT
<213> ORGANISM: Drosophila melanogaster

<400> SEQUENCE: 8

```
Met Ser Ala Tyr Tyr Arg Arg Ala Ala Leu Arg Lys Lys Ser Pro Ser
  1               5                  10                  15

Arg Gly Ser Ser Phe Glu Leu Glu Met Asn Glu Ser Gly Tyr Thr Ser
                 20                  25                  30

Phe Leu Ala Leu His Asn Ser Thr Ala Glu Thr Pro Phe Leu Leu Glu
             35                  40                  45

Asp Ala Glu Gly Glu Asn Cys Arg Asn Ala Ser Asn Thr Thr Thr Phe
         50                  55                  60

Phe Arg Gly Leu Asn Thr Pro Ser Gly His Gln Glu Gln Asp Leu Tyr
     65                  70                  75                  80

Trp Gly Lys Pro Tyr Pro Arg Thr Gln Pro Gln Lys Lys Phe Ser Ala
                 85                  90                  95

Glu Glu Glu Pro Phe Ser Met Thr Pro Arg Leu Gln Asp Glu His Ser
                100                 105                 110

Leu Pro Lys Arg Arg Lys Lys His Phe Gln Ser Pro His Ser Ser Pro
            115                 120                 125

Lys Lys Ser Lys Lys Leu Leu Phe Pro His Ile Glu Glu Pro Pro Lys
        130                 135                 140

Asn Arg Phe Tyr Gly Gly Val Glu Lys Leu Asp Ile Val Ala Lys Leu
    145                 150                 155                 160
```

```
Ala Gln Trp Gln Pro Ala Leu Gln Cys Ile Leu Arg His Val Gly Ala
            165                 170                 175

His Thr Leu Asp Val Met Thr Lys Val Ser Pro Ala Trp Lys Gln Ala
            180                 185                 190

Val Tyr Arg Ser Gln Arg Asp Leu Glu Arg Leu Gln Asn His Arg Leu
            195                 200                 205

Lys Leu Asn Leu Thr Lys Glu Asn Pro His Val Pro Lys Arg Cys Ser
            210                 215                 220

His Val Pro Lys Ala Asn His Thr Val Pro Leu Gln Thr Ser Asn His
225                 230                 235                 240

Ser Ser Leu Ala Asn Ser Val Arg Leu Ala Asn Gly Leu Gly Gln Leu
            245                 250                 255

Glu His Pro Pro Asp Gly Arg Gly Cys Arg Lys Gly Ala Ala Arg Arg
            260                 265                 270

Asp Ala Cys Cys Val Lys Cys Pro Arg Cys Gly Arg Gly Ser Arg Val
            275                 280                 285

Phe Ile Ser Glu Ala Ala Lys Cys Gly Glu Asn Leu Leu Ser Gln Thr
            290                 295                 300

Leu Pro Ile Gly Arg Thr Thr Ser Thr Phe Pro Cys Met Thr Gly Pro
305                 310                 315                 320

Pro Leu Lys Arg Phe Leu Ser Leu Asp Leu Asp Glu Val Arg Thr Ser
            325                 330                 335

Pro Gln Gly Pro Pro Tyr Asn Phe Ala Glu Cys Thr Ser Val Ile Cys
            340                 345                 350

Gln Phe Arg Phe Cys Val Asn Cys Leu Cys Lys Ser His Pro Gly Glu
            355                 360                 365

Arg Cys Leu Val Thr Glu Leu Asp Thr Pro Ser Lys Leu Met Met Pro
            370                 375                 380

Arg Glu Arg Leu Thr Pro Pro Gln Arg Ala Gln Asn Arg Asp Pro Lys
385                 390                 395                 400

Ile Thr Arg Lys Asn Ser Leu Lys Arg Leu Cys Phe
            405                 410
```

<210> SEQ ID NO 9
<211> LENGTH: 514
<212> TYPE: DNA
<213> ORGANISM: Danio rerio
<220> FEATURE:
<221> NAME/KEY: misc_feature
<222> LOCATION: (1)...(514)
<223> OTHER INFORMATION: n = A,T,C or G

<400> SEQUENCE: 9

| | | |
|---|---|---|
| aatcgattaa gaacccaaca ggtagttttt ttttaagttc ttgtaacatt gcttttttt | 60 |
| cctcttatgt ggcgctcaga ggcgacggat gctcctcttg cttcgagcgg agccggcaac | 120 |
| cagtgttttt tgtgtggagg aaaaactccg gacggtgttt cggcacggag ttgagtcatg | 180 |
| gaaagcagat tgcacaatg tgcaaaactc aaggcgcag ctgatgcgtg tgcaaacagc | 240 |
| cctctgcatt actgcatcaa agcgtgccgg agaactgcag cgggagcagc gccgcaggga | 300 |
| ttcatgctgt tcagagact gtgctgcctc tacatactgt tgaaaccggc ttgatttagt | 360 |
| cgcatttgc gctccaccca tatggcatgg cggcttctta acagccttgt gagcgggtgg | 420 |
| agaggaaacg gtctgcatgc angagaacac caccctgtcc aaggtgaagt ctcgagataa | 480 |
| agatcccata gaccggcccg agtccctgcg tgtt | 514 |

<210> SEQ ID NO 10
<211> LENGTH: 145
<212> TYPE: PRT
<213> ORGANISM: Danio rerio

<400> SEQUENCE: 10

```
Thr Arg Arg Asp Ser Gly Arg Ser Met Gly Ser Leu Ser Arg Asp Phe
  1               5                  10                  15

Thr Leu Asp Arg Val Val Phe Ser Cys Met Gln Thr Val Ser Ser Pro
             20                  25                  30

Pro Ala His Lys Ala Val Lys Lys Pro Pro Cys His Met Gly Gly Ala
         35                  40                  45

Gln Asn Ala Thr Lys Ser Ser Arg Phe Gln Gln Tyr Val Glu Ala Ala
     50                  55                  60

Gln Ser Leu Lys Gln His Glu Ser Leu Arg Arg Cys Ser Arg Cys Ser
 65                  70                  75                  80

Ser Pro Ala Arg Phe Asp Ala Val Met Gln Arg Ala Val Cys Thr Arg
                 85                  90                  95

Ile Ser Cys Ala Phe Glu Phe Cys Thr Leu Cys Gln Ser Ala Phe His
            100                 105                 110

Asp Ser Thr Pro Cys Arg Asn Thr Val Arg Ser Phe Ser Ser Thr Gln
        115                 120                 125

Lys Thr Leu Val Ala Gly Ser Ala Arg Ser Lys Ser Arg Ser Ile Arg Arg
    130                 135                 140

Leu
145
```

<210> SEQ ID NO 11
<211> LENGTH: 553
<212> TYPE: DNA
<213> ORGANISM: Rattus norveticus

<400> SEQUENCE: 11

```
cggccgcaaa ggttttttgt cgaatcacca attgtgggac atgataacaa ggaaaatcaa      60
cgtgtacaaa atatactaga tagttcaaag gaagtggaag agctggaggc cagcagactg     120
tatgaggaca gcggctactc ctcattcata cagagtgaca gtgacgatgg catccttatc     180
ctggagaatt tcagaaacag ttcccaggcc catctgctgc tgtcatcgca gagcccagac     240
cagcatccca acaaaaacct gctgcctgcc ctgcattttg aaagagtggt ttgctcaaca     300
ttaaaaaaga atggcaagcg aaactctaaa gtggatcaag aaatgctgaa ggaagttatc     360
gccagcggaa acattacact gcaaaatata attggcaaga aaatgggcct ggaacaccta     420
gatatcctgg ctgagctctc ccggagggga tgtatgcacc tgttagctaa tattttcatg     480
aagctcagcg gcatggactt aataaatttg tctaaagtga gcagaatttg gaagaagata     540
ctagaaagcg ata                                                        553
```

<210> SEQ ID NO 12
<211> LENGTH: 184
<212> TYPE: PRT
<213> ORGANISM: Rattus norveticus

<400> SEQUENCE: 12

```
Arg Pro Gln Arg Phe Phe Val Glu Ser Pro Ile Val Gly His Asp Asn
  1               5                  10                  15

Lys Glu Asn Gln Arg Val Gln Asn Ile Leu Asp Ser Ser Lys Glu Val
             20                  25                  30
```

Glu Glu Leu Glu Ala Ser Arg Leu Tyr Glu Asp Ser Gly Tyr Ser Ser
            35                  40                  45

Phe Ile Gln Ser Asp Ser Asp Gly Ile Leu Ile Leu Glu Asn Phe
    50                  55                  60

Arg Asn Ser Ser Gln Ala His Leu Leu Leu Ser Ser Gln Ser Pro Asp
65                  70                  75                  80

Gln His Pro Asn Lys Asn Leu Leu Pro Ala Leu His Phe Glu Arg Val
                85                  90                  95

Val Cys Ser Thr Leu Lys Lys Asn Gly Lys Arg Asn Ser Lys Val Asp
                100                 105                 110

Gln Glu Met Leu Lys Glu Val Ile Ala Ser Gly Asn Ile Thr Leu Gln
            115                 120                 125

Asn Ile Ile Gly Lys Lys Met Gly Leu Glu His Leu Asp Ile Leu Ala
    130                 135                 140

Glu Leu Ser Arg Arg Gly Cys Met His Leu Leu Ala Asn Ile Phe Met
145                 150                 155                 160

Lys Leu Ser Gly Met Asp Leu Ile Asn Leu Ser Lys Val Ser Arg Ile
                165                 170                 175

Trp Lys Lys Ile Leu Glu Ser Asp
                180

<210> SEQ ID NO 13
<211> LENGTH: 545
<212> TYPE: DNA
<213> ORGANISM: Bos taurus

<400> SEQUENCE: 13
gccgcttgct ctcctcctgc ggcagcagct ctctcacctg aggccgactc ctctcttacc      60
cctggcatga gccggcggcc ctgcagctgc tccctacggc cgctctccgg ttcctgccgc     120
tgcagctacg gcaccctgac agccgccggg cgcccttgcc cctcggacgg ttgtaaagaa     180
gaaagttcca ctctctctgt caaaatgaag tgtgatttta actataacca tgttcattct     240
ggaattaaac cagtaaagcc tgatgacagt agaagaaaag gttcctacac tactgcatat     300
ttggaaggtt cttataaaga ctgcattaaa gactacgaca gggtatcaga tgttgggtcc     360
cccgttgtga gccccaggat gtagaacttg aacctgaaag caagccatt gcataacaag     420
gaaaatcaac acatacaaca aacacttgat agttccaata acatacaaga actagagacc     480
agcggatgtt atgaagacag tggctactct tcattttccc aacgaagtgg cctcagtgaa     540
catga                                                                 545

<210> SEQ ID NO 14
<211> LENGTH: 159
<212> TYPE: PRT
<213> ORGANISM: Bos taurus

<400> SEQUENCE: 14

Met Ser Arg Arg Pro Cys Ser Cys Ser Leu Arg Pro Leu Ser Gly Ser
1               5                   10                  15

Cys Arg Cys Ser Tyr Gly Thr Leu Thr Ala Ala Gly Arg Pro Cys Pro
            20                  25                  30

Ser Asp Gly Cys Lys Glu Glu Ser Ser Thr Leu Ser Val Lys Met Lys
            35                  40                  45

Cys Asp Phe Asn Tyr Asn His Val His Ser Gly Ile Lys Pro Val Lys
    50                  55                  60

```
Pro Asp Asp Ser Arg Arg Lys Gly Ser Tyr Thr Thr Ala Tyr Leu Glu
 65                  70                  75                  80

Gly Ser Tyr Lys Asp Cys Ile Lys Asp Tyr Asp Arg Val Ser Asp Val
                 85                  90                  95

Gly Ser Pro Val Val Ser Pro Arg Ile Val Glu Leu Glu Pro Glu Ser
            100                 105                 110

Lys Pro Leu His Asn Lys Glu Asn Gln His Ile Gln Gln Thr Leu Asp
        115                 120                 125

Ser Ser Asn Asn Ile Gln Glu Leu Gly Thr Ser Gly Cys Tyr Glu Asp
    130                 135                 140

Ser Gly Tyr Ser Ser Phe Ser Gln Arg Ser Gly Leu Ser Glu His
145                 150                 155

<210> SEQ ID NO 15
<211> LENGTH: 42
<212> TYPE: PRT
<213> ORGANISM: Danio rerio
<220> FEATURE:
<221> NAME/KEY: DOMAIN
<222> LOCATION: (1)...(42)
<223> OTHER INFORMATION: Zinc-binding region

<400> SEQUENCE: 15

Cys Ser Arg Cys Ser Ser Pro Ala Arg Phe Asp Ala Val Met Gln Arg
 1               5                  10                  15

Ala Val Cys Thr Arg Ile Ser Cys Ala Phe Glu Phe Cys Thr Leu Cys
                20                  25                  30

Gln Ser Ala Phe His Asp Ser Thr Pro Cys
            35                  40

<210> SEQ ID NO 16
<211> LENGTH: 1341
<212> TYPE: DNA
<213> ORGANISM: Homo sapiens

<400> SEQUENCE: 16
atgagccggc gcccctgcag ctgcgcccta cggccacccc gctgctcctg cagcgccgcc    60
cccagcgcag tgacagccgc cgggcgccct cgaccctcgg atagttgtaa agaagaaagt   120
tctacccttt ctgtcaaaat gaagtgtgat tttaattgta accatgttca ttccggactt   180
aaactggtaa aacctgatga cattggaaga ctagtttcct acgcccctgc atatttggaa   240
ggttcctgta aagactgcat taagactatg aaaggctgtc atgtattggg gcaccgatt    300 gtggccccta ggattgtaca acttgaaact gaaagcaagc gcttgcataa caaggaaaat   360
caacatgtgc aacagacact taatagtaca aatgaaatag aagcactaga gaccagtaga   420
ctttatgaag acagtggcta ttcctcattt tctctacaaa gtggcctcag tgaacatgaa   480
gaaggtagcc tcctggagga gaatttcggt gacagtctac aatcctgcct gctacaaata   540
caagccccag accaatatcc aacaaaaac ttgctgccag ttcttcattt tgaaaaagtg   600
gtttgttcaa cattaaaaaa gaatgcaaaa cgaaatccta agtagatcg ggagatgctg    660 aaggaaatta tagccagagg aaattttaga ctgcagaata taattggcag aaaaatgggc   720
ctagaatgtg tagatattct cagcgaactc tttcgaaggg gactcagaca tgtcttagca   780 actatttag cacaactcag tgacatggac ttaatcaatg tgtctaaagt gagcacaact   840
tggaagaaga tcctagaaga tgataagggg gcattccagt tgtacagtaa agcaatacaa   900
agagttaccg aaaacaacaa taatttgca cctcatgctt caaccagaga atatgttatg   960
```

-continued

```
ttcagagccc cactggcttc tgttcagaaa tcagcagccc agacttctct caaaaaagat    1020
gctcaaacca agttatccaa tcaaggtgat cagaaaggtt ctacttatag tcgacacaat    1080
gaattctctg aggttgccaa gacattgaaa agaacgaaa gcctcaaagc ctgtattcgc     1140
tgtaatgcac ctgcaaaata tgattgctat ttacaacggg caacctgcaa acgagaaggc    1200
tgtggatttg attattgtac gaagtgtctc tgtaattatc atactactaa agactgttca    1260
gatggcaagc tcctcaaagc cagttgtaaa ataggtcccc tgcctggtac aagaaaagc     1320 aaaaagaatt tacgaagatt g                                              1341
```

<210> SEQ ID NO 17
<211> LENGTH: 447
<212> TYPE: PRT
<213> ORGANISM: Homo sapiens

<400> SEQUENCE: 17

```
Met Ser Arg Arg Pro Cys Ser Cys Ala Leu Arg Pro Pro Arg Cys Ser
 1               5                  10                  15

Cys Ser Ala Ala Pro Ser Ala Val Thr Ala Ala Gly Arg Pro Arg Pro
            20                  25                  30

Ser Asp Ser Cys Lys Glu Glu Ser Thr Leu Ser Val Lys Met Lys
        35                  40                  45

Cys Asp Phe Asn Cys Asn His Val His Ser Gly Leu Lys Leu Val Lys
    50                  55                  60

Pro Asp Asp Ile Gly Arg Leu Val Ser Tyr Ala Pro Ala Tyr Leu Glu
65                  70                  75                  80

Gly Ser Cys Lys Asp Cys Ile Lys Asp Tyr Glu Arg Leu Ser Cys Ile
                85                  90                  95

Gly Ala Pro Ile Val Ala Pro Arg Ile Val Gln Leu Glu Thr Glu Ser
            100                 105                 110

Lys Arg Leu His Asn Lys Glu Asn Gln His Val Gln Gln Thr Leu Asn
        115                 120                 125

Ser Thr Asn Glu Ile Glu Ala Leu Glu Thr Ser Arg Leu Tyr Glu Asp
    130                 135                 140

Ser Gly Tyr Ser Ser Phe Ser Leu Gln Ser Gly Leu Ser Glu His Glu
145                 150                 155                 160

Glu Gly Ser Leu Leu Glu Glu Asn Phe Gly Asp Ser Leu Gln Ser Cys
                165                 170                 175

Leu Leu Gln Ile Gln Ala Pro Asp Gln Tyr Pro Asn Lys Asn Leu Leu
            180                 185                 190

Pro Val Leu His Phe Glu Lys Val Val Cys Ser Thr Leu Lys Lys Asn
        195                 200                 205

Ala Lys Arg Asn Pro Lys Val Asp Arg Glu Met Leu Lys Glu Ile Ile
    210                 215                 220

Ala Arg Gly Asn Phe Arg Leu Gln Asn Ile Ile Gly Arg Lys Met Gly
225                 230                 235                 240

Leu Glu Cys Val Asp Ile Leu Ser Glu Leu Phe Arg Arg Gly Leu Arg
                245                 250                 255

His Val Leu Ala Thr Ile Leu Ala Gln Leu Ser Asp Met Asp Leu Ile
            260                 265                 270

Asn Val Ser Lys Val Ser Thr Thr Trp Lys Lys Ile Leu Glu Asp Asp
        275                 280                 285

Lys Gly Ala Phe Gln Leu Tyr Ser Lys Ala Ile Gln Arg Val Thr Glu
    290                 295                 300
```

```
Asn Asn Asn Lys Phe Ala Pro His Ala Ser Thr Arg Glu Tyr Val Met
305                 310                 315                 320

Phe Arg Ala Pro Leu Ala Ser Val Gln Lys Ser Ala Ala Gln Thr Ser
                325                 330                 335

Leu Lys Lys Asp Ala Gln Thr Lys Leu Ser Asn Gln Gly Asp Gln Lys
            340                 345                 350

Gly Ser Thr Tyr Ser Arg His Asn Glu Phe Ser Glu Val Ala Lys Thr
        355                 360                 365

Leu Lys Lys Asn Glu Ser Leu Lys Ala Cys Ile Arg Cys Asn Ala Pro
    370                 375                 380

Ala Lys Tyr Asp Cys Tyr Leu Gln Arg Ala Thr Cys Lys Arg Glu Gly
385                 390                 395                 400

Cys Gly Phe Asp Tyr Cys Thr Lys Cys Leu Cys Asn Tyr His Thr Thr
                405                 410                 415

Lys Asp Cys Ser Asp Gly Lys Leu Leu Lys Ala Ser Cys Lys Ile Gly
            420                 425                 430

Pro Leu Pro Gly Thr Lys Lys Ser Lys Lys Asn Leu Arg Arg Leu
        435                 440                 445
```

```
<210> SEQ ID NO 18
<211> LENGTH: 700
<212> TYPE: DNA
<213> ORGANISM: Homo sapiens
<220> FEATURE:
<221> NAME/KEY: promoter
<222> LOCATION: (1)...(581)
<223> OTHER INFORMATION: DNA binding consensus sequences for E2F
<220> FEATURE:
<221> NAME/KEY: misc_feature
<222> LOCATION: (581)...(581)
<223> OTHER INFORMATION: Start of transcription

<400> SEQUENCE: 18
ggagggagag cagagcgcgc gcgtaaatcc tagagaggcg ggctaagctg gactgggggg      60
agggtccgtc ttccggaaag tctggattcc cggacgagcc gagttgctgc tcaccgaact    120
cccgttcgag agatgatcga agaaagtcgg ctaccatttg tacccatcaa agatctccag    180
atggaagcca gcgctgaatt tgggctgaga ttaggacttg caggaggccg gtccagaaga    240
cggcggaagg aatcttggcg ggcgcacgca tgcgtgatag accctccaca cgtgtggccg    300
ggccgcggcc tccccgtgct cggaggtccc gcccccggcc gtagcatctt tccggacgtg    360
gggagccggt aagctggaag ggggctgggc ttcgcggctc ggccccgcct ggcagcctc     420 caattgggcg cggacgaggg cgcccccacc cactgccctc ctattggtgc gcgcatgcaa    480
gcgacgcgtc tcattggacc gcgcggattt aggcaccaaa ttcaaagatt ttaaaagtac    540
cagctggcgc cttttaagag atacaggtct gtgaagcagg caggttgctc agctgccccc    600
ggagcggttc ctccacctga ggcagactcc acgtcggctg gcatgagccg gcgcccctgc    660
agctgcgccc tacggccacc ccgctgctcc tgcagcgcca                          700
```

MODULATION OF CELL DIVISION BY AN EARLY MITOTIC INHIBITOR PROTEIN

STATEMENT REGARDING GOVERNMENT RIGHTS

This invention was supported at least in part by grant number RO1 GM54811 from the National Institutes of Health. The U.S. Government may have certain rights in the invention.

BACKGROUND OF THE INVENTION

The cell division cycle is a set of fundamental processes in biology, which ensure the controlled proliferation of cells. Under normal growth conditions, cell proliferation is tightly regulated in response to intra- and extracellular signals. This is achieved by a complex network of proteins that are components of signal transduction pathways. Activation of a stimulatory component or a loss of an inhibitory component can lead to the unregulated cell cycle activity, which may result in the development of cancer. Progression through mitosis is controlled by cyclin-dependent kinases, which drive cells into metaphase, and by the anaphase-promoting complex/cyclosome, a ubiquitin ligase that triggers sister chromatid separation and exit from mitosis.

To ensure proper mitosis, chromosome cohesion must be maintained until all chromosomes are attached to opposite poles of the mitotic spindle and aligned at the metaphase plate. At the onset of anaphase, the activity of separins contributes to the release of cohesins from chromosomes, allowing for the segregation of bivalents to opposite spindle poles. Separin activity is blocked by binding to a class of proteins known as securins, whose turnover at the metaphase-to-anaphase transition is triggered by the Anaphase Promoting Complex (APC). The mitotic spindle cell cycle checkpoint coordinates the timing of these events and acts as an input mechanism for DNA damage/stress pathways. Failure of this precise network leads to genomic instability and/or cell death.

Ubiquitylation enzymes provide critical signaling in a number of physiological pathways. The ubiquitin ligases provide crucial elements of specificity that direct the formation of polyubiquitin chains on protein targets, thereby marking the target for proteolytic destruction. Specificity in protein ubiquitylation derives from the substrate protein recognition by the ubiquitin ligase complex. Analysis of the SCF ubiquitin ligase has shown the utilization of substrate-specific adaptor subunits called F-box proteins to recruit various substrates to a core ubiquitylation complex.

A particularly interesting and complex ubiquitin ligase is the APC, which targets proteins containing a recognition sequence for ubiquitylation and subsequent proteolysis, and is required for mitotic progression and for exit from mitosis. This ubiquitylation reaction catalyzes the destruction of a number of mitotic substrates, including the mitotic cyclins, cyclin A and B, as well as the cell cycle regulators securin and geminin. APC activation is achieved by binding Cdc20 or Cdh1, but this and APC interactions with mitotic kinases are not sufficient to explain the timing of APC activity.

The critical role of the APC in controlling cell cycle and growth makes the further investigation of its regulation of great interest.

Relevant Literature

The Anaphase Promoting Complex and its role in cell division is reviewed by Page and Hieter (1999) *Annu Rev Biochem.* 68:583–609; and Zachariae and Nasmyth (1999) *Genes Dev.* 13(16):2039–58. A review of substrate recognition and catalysis by ubiquitin ligases may be found in Jackson et al. (2000) *Trends Cell Biol.* 10(10):429–39.

International patent application WO00/12679 discusses novel ubiquitin ligases.

SUMMARY OF THE INVENTION

Compositions and methods are provided for the control of cell division, through a protein inhibitor of the Anaphase Promoting Complex (APC). The Early Mitotic Inhibitor (Emi1) prevents activation of the APC during the cell cycle. The Emi1 protein is thus an APC ubiquitin ligase inhibitor. Emi1 finds use where it is desirable to modulate the cycling of cells, e.g. in the treatment of hyperproliferative conditions, in diseases involving tissues where there is a high rate of cell turnover, and in modulating oocyte activation. In addition to therapeutic use, Emi1 proteins are utilized in screening and research methods for the determination of specific analogs, agonists, antagonists and mimetics. The zinc-binding region of the protein is of particular interest for its biological activity as a ubiquitin ligase inhibitor, and as a substrate for drug screening and design.

The invention also provides diagnostics and therapeutics comprising Emi1 nucleic acids, their corresponding genes and gene products, proteins and fragments thereof, antisense nucleotides, and antibodies specific for one or more epitopes of the Emi1 polypeptide. The nucleic acid compositions find use in identifying homologous or related genes; for production of the encoded protein; in producing compositions that modulate the expression or function of its encoded protein; for gene therapy; mapping functional regions of the protein; and in studying associated physiological pathways. In addition, modulation of the gene activity in vivo is used for prophylactic and therapeutic purposes.

BRIEF DESCRIPTION OF THE DRAWINGS

FIG. 1A shows the alignment of *Xenopus laevis* (SEQ ID NO: 2), *Homo sapiens* (SEQ ID NO: 4), *Mus musculus* (SEQ ID NO: 6), and *Drosophila melanogaster* Emi1 homologs (SEQ ID NO: 8).

FIGS. 3A to 3H show that Emi1 prevents the ubiquitin- mediated destruction of APC substrates and inhibits mitotic exit. A. Emi1 prevents cyclin A and B destruction and mitotic exit in cycling egg extracts. Activated $Xenopus$ cycling egg extracts were incubated with either buffer (■) or 1 μM purified MBP-Emi1 (Δ). Aliquots were removed at the indicated times and assayed for DNA morphology (graph) or $Xenopus$ cyclins A and B by immunoblotting (lower panels). B. Excess Emi1 does not affect the kinetics of cyclin B/Cdc2 activation in egg extracts. Activated $Xenopus$ cycling egg extracts were incubated with buffer or 1 μM purified MBP- Emi1. Aliquots were removed at the indicated times and processed for the histone H1 kinase activity of immunopre- cipitated cyclin B1. C. Emi1 stabilizes Securin and Geminin. $^{35}$S-labeled IVT $Xenopus$ securin or geminin pro- tein was incubated in Δ90 extracts treated with buffer (control) or 1 μM purified MBP-Emi1. Aliquots were removed at the indicated times and analyzed by SDS-PAGE and autoradiography. D. Emi1 inhibits cyclin B ubiquityla- tion in mitotic extracts. An $^{125}$I-labeled cyclin B N-terminal fragment was incubated in Δ90 extracts treated with 2.5 μM purified MBP (left) or MBP-Emi1 (right). Aliquots were removed at the indicated times and analyzed as in C. E, F, G. $^{35}$S-labeled IVT cyclin B N-terminal fragment was added to Δ90 extracts treated with Emi1 variants. Aliquots were removed at indicated times, resolved by SDS-PAGE and quantitated by Phosphorimager. E. The Emi1 C-terminus is sufficient to block cyclin B destruction. Additions: buffer (■) or 1 μM purified MBP-Emi1 (●), MBP-Emi1-NT (Δ), MBP-Emi1-CT (□). F. The Emi1 ZBR but not the F-box domain is required to block cyclin B destruction. Additions: buffer (■), 1 μM purified MBP-Emi1 (●), MBP-EL198AA (▲), MBP-Emi1ΔZBR (□), MBP-Emi1-5P (○). G. ZBR mutations fail to inhibit cyclin B destruction. Additions: buffer (■), 1 μM purified MBP-Emi1 (●), MBP-C341S (▲), MBP-C346S (○), MBP-C351S (Δ), MBP-C354S/C356S (□), MBP-C364S (♦). H. Injection of Emi1 blocks $Xenopus$ embryos in mitosis with high Cdk kinase activity. 1 pmol purified MBP-Emi1, MBP-Emi1-NT, MBP-Emi1-CT, or MBP was injected into one blastomere (right side) of two- cell stage $Xenopus$ embryos. Embryos were photographed 2.5 h after injection (left panel). For kinase assays, both blastomeres of two-cell stage embryos were injected and extracts from injected embryos assayed for histone H1 kinase activity 2.5 h post-injection (right panel). Unfertilized eggs and equivalent aliquots of interphase and Δ90 extracts were assayed as controls.

FIGS. 4A to 4F show that transfection of Emi1 into XTC cells causes a mitotic block. A. Emi1 localization. XTC cells were labeled with affinity-purified antibodies to Emi1, anti- α-tubulin, and Hoechst 33258 dye. Anti-Emi1 antibodies were blocked with MBP-Emi1 protein ("Block"). The Emi1 staining (red) and α-tubulin (green) images were merged (Merge) to show Emi1 spindle localization. B. Deconvolu- tion image of Emi1 spindle localization. XTC cells were labeled as in A, and the Emi1 staining (red) and α-tubulin (green) images were merged (Merge) to show the Emi1 spindle localization. C. Emi1 overexpression causes a mitotic index increase. XTC cells were co-transfected with GFP and myc-tagged constructs expressing Emi1 variants. Cells were fixed and stained with anti-α-tubulin antibody and Hoechst 33258 dye. The number of GFP positive mitotic cells was quantitated based on DNA and spindle morphol- ogy. D. Flow cytometric analysis of Emi1-transfected XTC cells. Cells were fixed, labeled with propidium iodide, and analyzed by flow cytometry. The table lists the % GFP positive cells in each cell cycle stage for each transfection. *The percentage mitotic for the Emi1-5P mutant is likely an underestimate because many cells expressing this mutant undergo apoptosis. E, F. Emi1 overexpression blocks cells in prometaphase. XTC cells were transfected with either myc- vector or myc-tagged Emi1 and processed for immunofluo- rescence to visualize α-tubulin and DNA. Promet.=normal prometaphase cell, met.=normal metaphase cell (E). The number of GFP positive cells in each mitotic phase was quantitated as in C (F).

FIGS. 5A to 5D show that Emi1 depletion prevents mitotic entry in egg extracts. A. Emi1 depletion prevents cyclin B accumulation in $Xenopus$ cycling extracts. Equal aliquots were removed at the indicated times from preim- mune sera-depleted, Emi1-depleted, or Emi1-depleted cycling extracts pre-incubated with either 300 nM MBP- Emi1, 0.13 volumes extract, or beads from the Emi1 deple- tion. Samples were processed for immunoblotting with anti-cyclin B2 and anti-Orc1 antibodies (as a loading con- trol). Exposure time is the same for all blots. B, C. Emi1- depleted cycling extracts fail to enter mitosis. Sperm DNA was added to preimmune sera-depleted, Emi1-depleted, or Emi1-depleted cycling extracts pre-incubated with either 300 nM MBP-Emi1, 0.2 volumes extract, 6 μM GST-Mad2, or 60 μg/ml GST-Δ90 cyclin B. Aliquots were removed at the indicated times, fixed onto slides, and DNA visualized by Hoechst 33258 staining (B). The number of interphase and mitotic figures was quantitated (C). D. Equal amounts of undepleted, preimmune sera-depleted and Emi1-depleted extracts were resolved by SDS-PAGE and processed for immunoblotting with anti-Emi1 antibodies. Emi1 depletion removes >80% of the protein.

FIGS. 6A to 6G show that Emi1p interacts with Cdc20 and inhibits APC activation by Cdc20. A. Emi1 co-immunoprecipitates with Cdc20 but not APC2. Preimmune (PI) or anti-Emi1 immunoprecipitates from interphase egg extract were assayed by immunoblotting for APC2 (upper panel) and Cdc20 (lower panel). B. Sucrose gradient co-sedimentation of Emi1 and Cdc20. Interphase egg extract was fractionated on a 10–40% sucrose gradient, and fractions analyzed by immunoblotting with antibodies to the indicated proteins. C. Emi1 and Cdc20 co-fractionate during gel filtration chromatography. Interphase egg extract was resolved on a Resource Q anion exchange column and fractions containing Emi1 chromatographed on an S-300 gel filtration column and immunoblotted for Emi1 and Cdc20 (left panel). Preimmune (PI) or anti-Emi1 immunoprecipitates from a 100 kDa-200 kDa fraction were assayed by immunoblotting for Cdc20 (right panel). D. Emi1 and Cdc20 associate in baculovirus co-infection. SF9 cells were co-infected with baculovirus-expressed Emi1 and Cdc20, precipitated with preimmune (PI) or anti-Emi1 antisera, and analyzed for Cdc20 by immunoblotting. E. Cdc20 rescues cyclin B destruction. $^{35}$S-labeled IVT N-terminal cyclin B was added to mitotic Xenopus egg extracts treated with buffer (■), 1 µM purified MBP-Emi1 (●), 1 µM MBP-Emi1 plus 1 µM His-Cdc20 (△), or 1 µM MBP-Emi1 plus 3 µM His-Cdc20 (□). Aliquots were removed at the indicated times, resolved by SDS-PAGE and quantitated on a Phosphorimager. F. Cdc20 interacts with both the N-terminus and the ZBR of Emi1 in vitro. Purified MBP-Emi1 fusion protein variants and purified baculovirus-expressed Cdc20 were incubated together in binding buffer, bound to amylose beads, washed, and assayed for Cdc20 by immunoblotting (upper panel). Purified GST-Emi1, GST-Emi1-NT, GST-Emi1-CTΔZBR (residues 248–334), or GST-Emi1-CTZBR (residues 335–364) was incubated with $^{35}$S-labeled in vitro translated (IVT) Cdc20(1–158), bound to glutathione agarose, and analyzed by SDS-PAGE and autoradiography (lower panel). G. Inhibition of Cdc20-mediated activation of the APC by Emi1. IVT Cdc20 (2–8) or rabbit reticulocyte lysate (1) was incubated for 30 min with buffer (1 and 2) or purified bacterially expressed 1 µM MBP-Emi1 (3), 3 µM MBP-Emi1 (4), 6 µM MBP-Emi1 (5), 3 µM MBP-Emi1-CT (6), 6 µM MBP (7), or 20 µM GST-Emi1-CTΔZBR (8). APC was immunopurified from mitotic egg extracts with anti-Cdc27 beads, then incubated with the Cdc20/protein mixtures for 1 hr. APC beads were washed, and assayed for cyclin ubiquitylation activity using an $^{35}$S-labeled IVT N-terminal Xenopus cyclin B substrate.

FIGS. 11a–11d. hEmi1 overcomes a Cdh1-induced G1 block and prevents destruction of APC$^{Cdh1}$ substrates in vivo. a, Overexpression of hEmi1 increases S and G2-M phase fraction and cyclin A expression. hEmi1 was cotransfected with GFP (10:1 ratio) into 293T cells. Cells were harvested for DNA analysis and cell sorting 24 hours post-transfection. Transfected 293T cells were fixed and stained with propidium iodide to analyze the DNA content of GFP-positive cells (top). GFP-positive cells were immunoblotted for cyclin A, cyclin B, Myc-hEmi1, and actin (bottom). b, hEmi1 but not Mad2 rescues a Cdh1-induced G1 arrest. Transfected 293T cells were fixed and stained with propidium iodide to analyze the DNA content of GFP-positive and GFP-negative cells harvested 24 hours post-transfection. c, APC$^{Cdh1}$ substrates are stabilized by hEmi1 in vivo. Western blots of cyclin A, cyclin B, securin, HA-Cdh1, Myc-tagged proteins, actin, and GFP-tagged proteins from 293T cells sorted 24 hours post-transfection into GFP Positive (GFP POS) and GFP negative (GFP NEG) populations. d, hEmi1, but not Mad2B, rescues a Cdh1-induced G1 arrest and stabilizes APC$^{Cdh1}$ substrates in vivo. GFP positive cells were analyzed for DNA content as in FIG. 5b. Lysates from GFP positive cells were immunoblotted as in FIG. 5c.

FIGS. 12a–12c. hEmi1 promotes S phase entry. a, Overexpression of hEmi1 can overcome a pRBΔCdk-induced G1 block. U2OS cells were transfected with the indicated expression plasmids. 36 hours post-transfection, cells were treated with nocodazole. cells were fixed and analyzed for DNA content 48 hours post-transfection. b, hEmi1 is one of three known genes to rescue a pRBΔCdk-induced G1 block. A bar graph quantitates the percentage of cells in G1 after transfection of the indicated plasmids as described in FIG.

6a. c, Microinjection of plasmid encoding wild-type hEmi1 accelerates S phase, while microinjection of catalytically inactive hEmi1 delays S phase.

Figure 13:
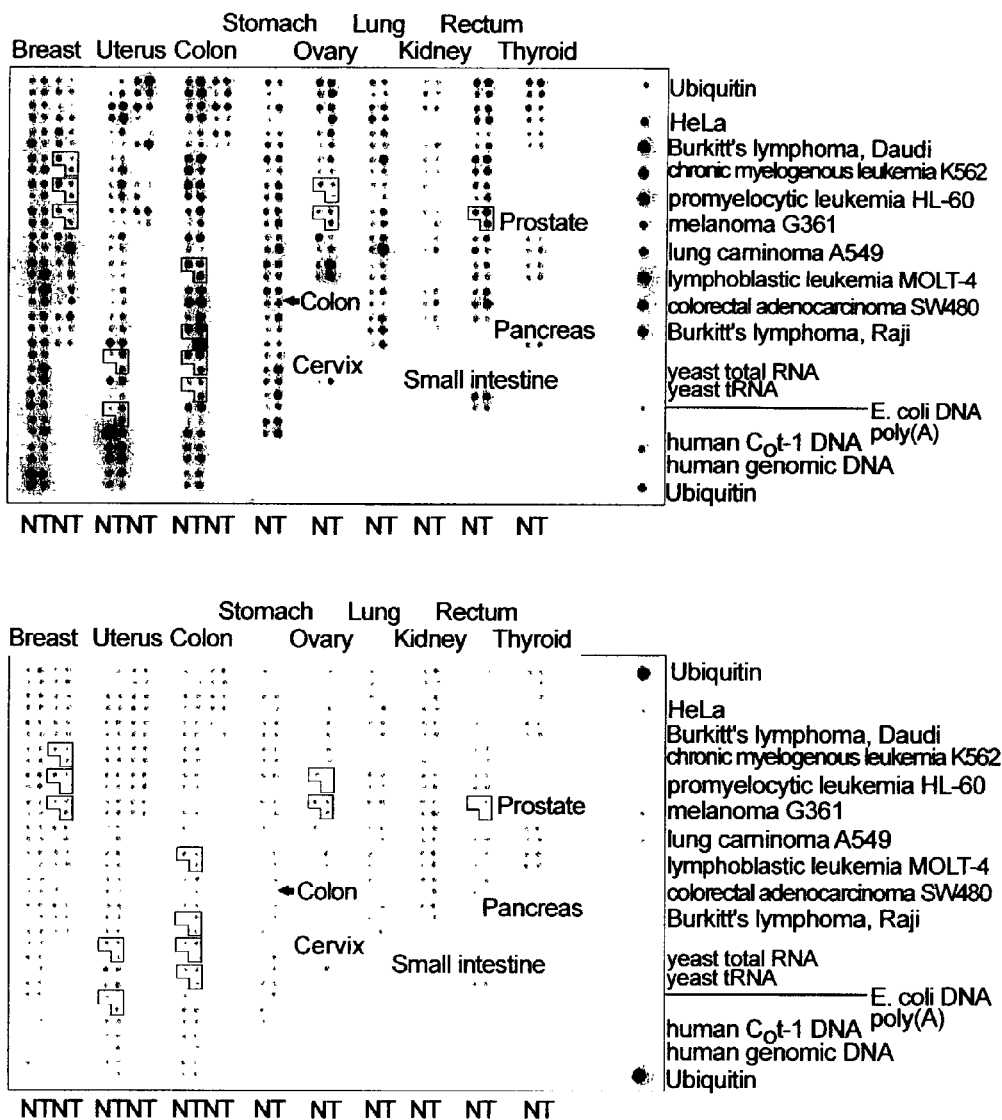

FIG. 13. hEmi1 transcripts are upregulated in various tumors. A radioactive probe was generated from hEmi1 cDNA for Northern blotting an array of matched normal (N) and tumor (T) tissues (top). A control probe was generated from ubiquitin cDNA to measure the mRNA expression of a housekeeping gene (bottom).

FIGS. 14a–d. Emi1 is sufficient to prevent release from CSF block in the presence of $Ca^{2+}$ a,b. Addition of Emi1 or a destruction box (D-box) peptide stabilizes cyclin B, Mos, and blocks MAP kinase inactivation in the presence of calcium. CSF extracts were preincubated with MBP-Emi1 (1 μM) or MBP (1 μM, control), destruction box (D-box) peptide (675 μM) or control peptide (675 μM), and released with calcium. Samples were immunoblotted with antibodies to Cyclin B2, Mos (Santa Cruz Biotechnology), and active MAP kinase (NEB). Times after calcium addition are indicated. c. Emi1 block to CSF release does not require the MAP kinase pathway. CSF extracts were preincubated with MBP-Mos (1 μM), U0126 (50 μM) (Promega), or U0126 (50 μM) and then MBP-Emi1 (1 μM). Extracts were released with calcium (except where indicated) and analyzed as in a. Control extracts in a, b, and c reentered mitosis by ~75 min. d. Constitutively active CaMKII cannot trigger calcium-independent cyclin B destruction and mitotic exit in the presence of Emi1. Extracts were analyzed as in a. Times after CaMKII addition are indicated.

FIGS. 15a–h. Emi1 is required for CSF arrest. a. Emi1 accumulates in the maturing oocyte. Samples from a maturation time course following progesterone addition (at t=0) and equal aliquots of stage I–V oocytes were analyzed for Emi1, Cdc20, and active MAP kinase by immunoblotting and cyclin B associated kinase activity by H1 kinase assay. GVBD=time at which 100% germinal vesicle breakdown had occurred. b. Specificity of Emi1 immunodepletion. Extracts were assayed by immunoblotting for Orc1 as a loading control (top), Emi1 (middle), and Cdc20 (bottom). Beads from Emi1- and mock-depleted extracts (from the equivalent of 1 μl of extract) and CSF extract (1 μl) were assayed for cyclin B by immunoblotting (right). c–h. Emi1 depletion causes cyclin B destruction and mitotic exit in the absence of calcium. c–e. Emi1-depleted and mock-depleted extracts plus (d and e) or minus (c) sperm DNA were warmed to 23 C. Calcium was added at 60 minutes. Samples were taken at the indicated time after warming, and immunoblotted for cyclin B (c) or assayed for DNA morphology (d). Mitotic figures were quantitated (e). f–h.—Similar to c,d, and e, except one sample was preincubated with active non-degradable MBP-Emi1-CT domain during the immunodepletion, and no calcium was added. A background band (*) served as a loading control and exposure time is the same for all blots.

FIGS. 16a–e. Addition of Exogenous Cdc20 to CSF extracts activates cyclin B destruction and mitotic exit in the absence of calcium a. CSF extracts were preincubated with buffer, 1 or 3 μM Cdc20, 3 μM Cdc20 preincubated with 3 μM Emi1, or 3 μM Cdc20 preincubated with 1 μM Mos. Extracts were warmed to 23 C and aliquots analyzed for cyclin B levels by immunoblotting. A background band (*) served as a loading control and exposure time is the same for all blots. b, c. Sperm DNA was added to extracts treated as in A, and morphology was assessed and quantitated. d, e. Emi1 and Cdc20 dissociate following release from CSF arrest. Calcium was added at time 0 to CSF extracts (d) or CSF extracts preincubated with $^{35}S$-labeled in vitro translated Cdc20 (e), and Emi1-Cdc20 coimmunoprecipitation was assayed by immunoblotting or autoradiography. Unprecipitated extracts from specific time points were resolved by SDS-PAGE and analyzed as loading controls (lower panels).

Figure 17A:
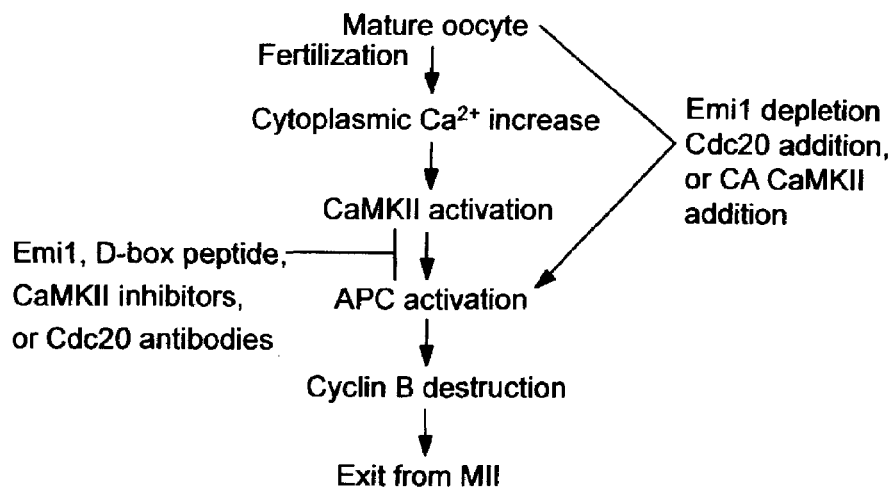
Figure 17B:
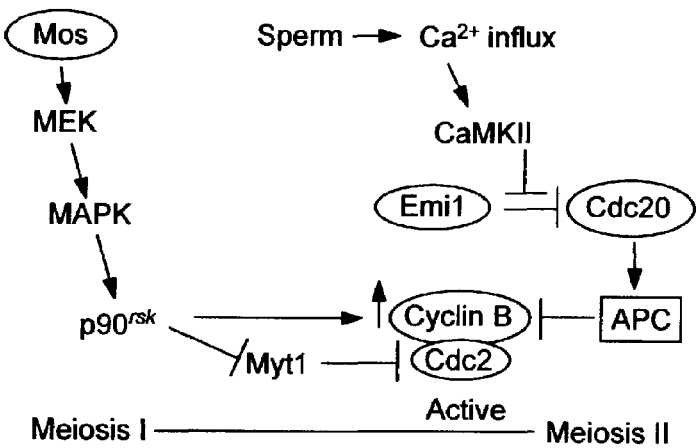

FIGS. 17a–b. Model a. Perturbations that bypass the calcium requirement for APC activation in the mature CSF-arrested oocyte: 1) Emi1 depletion; 2) excess Cdc20 protein; 3) constitutively active (CA) CaMKII addition. Calcium-triggered APC activation is blocked by Emi1 protein addition, Cdc20 neutralizing antibodies, or CaMKII inhibitors. b. Model of how Emi1 and the Mos/MAPK pathway act to prevent release from metaphase of MII by stabilizing cyclin B/Cdc2 activity. Mos promotes cyclin B/Cdc2 activity by negatively regulating the Myt1 kinase and by increasing cyclin B synthesis during the MI-MII transition. Emi1 inhibits APC-dependent cyclin B destruction in MII, thereby stabilizing cyclin B/Cdc2 activity.

DESCRIPTION OF THE SPECIFIC EMBODIMENTS

Nucleic acid compositions encoding Early Mitotic Inhibitor protein (Emi1) are provided. They are used in identifying homologous or related genes; in producing compositions that modulate the expression or function of its encoded protein; for gene therapy; mapping functional regions of the protein; and in studying associated physiological pathways. The Emi1 gene product is a ubiquitin ligase inhibitor having an F-box domain, zinc-binding region, and sequence motifs for phosphorylation. The wild-type Emi1 proteins have the ability to specifically bind to Cdc20 protein; to bind to Cdh1 protein; to block the destruction of cyclins A and B, securin and geminin during the normal cell cycle; and to block cellular exit from mitosis. Fragments and mutations of Emi1 protein are also provided.

Modulation of Emi1 gene activity in vivo is used for prophylactic and therapeutic purposes, such as treatment of cancer, regulation of oocyte activation, investigation of mitosis signaling pathways, identification of cell type, and the like. The protein is useful as an immunogen for producing specific antibodies, in screening for biologically active agents that act in the regulation of mitosis, and for therapeutic and prophylactic purposes.

The present invention demonstrates that Emi1 regulates progression through cell division by preventing premature APC activation. Emi1 is also strong S phase promoter, and prevents activation of unfertilized eggs. Emi1 binds the APC activators Cdc20 and Cdh1 and Emi1 prevents activation of the APC by either Cdc20 or Cdh1. Hence, products that modulate the expression and/or activity of Emi1 have a therapeutic effect in the treatment of cancer, leukemia, solid tumors, chronic or acute inflammatory disease, restenosis, diabetes, neurological disorders, arthritis and osteoporosis, among other indications.

Characterization of Emi1

The genetic sequences of Emi1 are provided in the sequence listing. The *Xenopus laevis* gene is provided as SEQ ID NO:1, the encoded polypeptide product as SEQ ID NO:2. The human nucleotide and amino acid sequences are provided as SEQ ID NO:3 and 4, and the promoter region of the human gene is provided as SEQ ID NO:18; the *Mus musculus* as SEQ ID NO:5 and 6; and the *Drosophila melanogaster* sequences as SEQ ID NO:7 and 8, respectively. A partial sequence from *Danio rerio* and it's translation are provided as SEQ ID NO:9 and 10; *Rattus norveticus* is provided as SEQ ID NO:11 and 12; and *Bos Taurus* as SEQ ID NO:13 and 14.

APC inhibition assays and rescue experiments described herein indicate that Emi1 is a direct Cdc20/Cdh1 inhibitor. The Emi1 zinc-binding region (ZBR) binds to Cdc20 in vitro, and is required to inhibit the APC. The ZBR cooperates with the Emi1 N-terminus to bind Cdc20 and may prevent the interaction of Cdc20 with APC substrates. Importantly, Emi1 does not inhibit the substrate and Cdc20/Cdh1-independent ubiquitylation activity of the APC2/APC11 core complex, further indicating that Emi1 inhibits APC activity through Cdc20/Cdh1 and not at the level of the APC enzymatic machinery. Further indicating its specificity, Emi1 does not inhibit SCF ubiquitin-ligase activity in vitro, or SCF-dependent events.

In somatic cells, hEmi1 is a strong S phase promoting factor. Microinjection of Emi1 caused an acceleration of S phase entry, and that loss of function of Emi1 through treatment of cells with siRNA or microinjection of a dominant-negative hEmi1 mutant causes a decrease in cyclin A levels and a delay in S phase entry. Emi1 overexpression can cause aberrancies in chromosome segregation, and may contribute to genomic instability by subverting early mitotic events as well as the balance of the S-phase promoting transcriptional program. Emi1 transcript levels are elevated in highly proliferative tissues including the thymus, testis, and ovary, and are also upregulated in a variety of tumors. 30–40% of tumors of the breast, ovary, uterus, colon, and lung show a substantial increase in expression relative to matched normal tissue. Emi1 overexpression correlates with estrogen-receptor negative breast tumors and with a poor clinical outcome in breast cancer.

Emi1 is also active in oocytes. Vertebrate eggs are arrested at metaphase of meiosis II (MII), and the ability of APC to trigger metaphase exit is blocked cytostatic factor (CSF). Fertilization causes a transient increase in cytoplasmic calcium leading to CSF inactivation, APC activation, cyclin B destruction, and mitotic exit. Emi1 is required and sufficient to inhibit the APC and prevent mitotic exit in CSF-arrested eggs. Emi1 is required to arrest unfertilized eggs at metaphase of meiosis II and is the mediator of CSF activity.

Specific mutations introduced into Emi1 include amino acid substitutions introduced into conserved F-box residues; truncations of the carboxy or the amino terminus of the protein, deletions of the zinc-binding region, substitutions of alanine for serine or threonine in one or more of the SP/TP phosphorylation sites; and substitution of cysteine 341 or 346 with serine.

A polypeptide fragment of particular interest is the ZBR of Emi1, which is sufficient in itself to inhibit the APC, and which is sufficient for binding to Cdh1, and to Cdc20. It is believed that the ZBR inhibits the APC through these binding events. This region is useful as a regulator of mitosis, as a chemotherapeutic agent, and for drug screening and design. Because of the biological activity, size of the region, and defined structure, it is of particular value in rational drug design for mimetics, agonists, inhibitors, and the like.

For the purposes of this invention, the ZBR may be defined as the contiguous amino acid sequence set forth in SEQ ID NO:2, residues 323–392, i.e. the carboxy terminal region of the protein; of which the region from residues 323–364 is sufficient for activity. The corresponding sequence in the human Emi1 is SEQ ID NO:4, residues 378–447, more particularly residues 378–419. The corresponding sequence in the mouse gene is SEQ ID NO:6, residues 352–421, more particularly residues 352–393. The *Drosophila* homolog contains an insertion in this region, and the zinc-binding region extends from SEQ ID NO:8, residues 313–370. The *Danio rerio* ZBR is provided as SEQ ID NO:15. The zinc-binding region can be identified by alignment of the characteristic cysteine residues, to determine the corresponding region in other homologs of Emi1.

The biologically active ZBR peptide may be produced in conjunction with the naturally occurring Emi1 protein, fused to other functional peptide sequence at its carboxy or amino terminus, or as an isolated peptide lacking other Emi1 sequences. The free ZBR is derived from the native form by deletion of the amino terminal sequence, and optionally by further deletion of the carboxy terminus. The protein may be truncated by proteolytic cleavage, or by expressing a genetically engineered truncated form. Not more than about 10, usually not more than about 5, preferably none of the amino acids outside of the ZBR at either terminus will be included.

One may wish to introduce a small number of amino acids at the polypeptide termini, usually not more than 20, more usually not more than 15. In addition, one may wish to substitute or delete one or more amino acids with a different amino acid for similar reasons, usually not substituting or deleting more than about ten amino acids, more usually not more than about five amino acids. The deletion or insertion of amino acids will usually be as a result of the needs of the construction, providing for convenient restriction sites, addition of processing signals, ease of manipulation, improvement in levels of expression, or the like.

Another polypeptide fragment of interest is the portion of Emi1 that is amino terminal of the F-box. This region confers instability on the protein, and may be used as a dominant negative to stabilize wild type Emi1 or in determining the degradation pathway for the protein, etc. This amino terminal fragment may be defined for the purposes of this invention, for example, as the region extending from SEQ ID NO:2, residues 1–193; or SEQ ID NO:4, residues 1–243; or SEQ ID NO:6, residues 1–218; or SEQ ID NO:8, residues 1–153.

Other Emi1 mutations of interest include a degradation-stabilized mutant. The *Xenopus* Emi1 protein contains 4 phosphorylation motifs in the amino terminal portion of the protein, as shown in FIG. 1 (SEQ ID NO:2, residues 10/11; 29/30; 105/106; and 123/124. The human protein (SEQ ID NO:4) comprises these motifs at residues 20/21; 75/76; 98/99, 102/103 and 182/183. A degradation stable variant of the human sequence is provided as SEQ ID NO:16, the amino acid translation as SEQ ID NO:17. The presence of any one of these motifs is sufficient for phosphorylation, and subsequent degradation of Emi1. Degradation resistant forms of the protein are produced by amino acid substitution of the serine or threonine resides, usually substitution with any one of alanine, glycine, leucine, isoleucine, or valine. The degradation stabilized mutant proteins are useful in determining the activity of Emi1, in comparison studies with the wild-type protein, in determining the degradation pathway for the protein, etc.

A domain of the Emi1 protein that is also of particular interest is the F-box. F-box regions act as adaptors, and are involved in recruiting SCF ubiquitin ligase activity. Emi1 forms a complex with Skp1 and Cul1, comprising a part of an SCF ubiquitin ligase. As such, Emi1 can be used to identify new SCF ubiquitylation targets. The Emi1 F-box may also be used to provide binding specificity for the active inhibitor defined by the ZBR.

Polypeptides comprising the F-box region are useful in determining binding specificities, in targeting molecules to the APC, in drug screening and design, and the like. The F-box region may be defined for the purposes of this invention, for example, as the region extending from SEQ ID NO:2, residues 193–246; or SEQ ID NO:4, residues 244–297; or SEQ ID NO:6, residues 219–272; or SEQ ID NO:8, residues 154–203. The F-box may be produced as a free peptide or fused to other sequences, as described for the ZBR region.

Substitution of glutamate 198 with alanine and leucine 199 with alanine abrogates binding of Emi1 to Skp1. Skp1 binding resistant forms of Emi1 are produced by amino acid substition of glutamate 198 and leucine 199, usually with any one of alanine, glycine, leucine, isoleucine, or valine. The Skp1 binding resistant forms of Emi1 are useful in determining the activity of Emi1, in comparison studies with the wild type protein, as a dominant negative protein in Emi1 F-box dependent assays, etc.

Emi1 Nucleic Acids

The sequence of a Emi1 gene, including flanking promoter regions and coding regions, may be mutated in various ways known in the art to generate targeted changes in promoter strength, sequence of the encoded protein, etc. Novel mutated forms of Emi1 are provided, as described above. The nucleic acids encoding these peptides may be produced by any convenient method, as is known in the art. The DNA sequence or protein product of such a mutation will usually be substantially similar to the sequences provided herein, i.e. will differ by at least one nucleotide or amino acid, respectively, and may differ by at least two but not more than about ten nucleotides or amino acids. The sequence changes may be substitutions, insertions or deletions. Deletions may further include larger changes, such as deletions of a domain or exon. Other modifications of interest include epitope tagging, e.g. with the FLAG system, HA, etc. For studies of subcellular localization, fusion proteins with green fluorescent proteins (GFP) may be used. Fusions of Emi1 with tags, including maltose binding protein (MBP), Glutathione S-transferase (GST) protein, etc, may be used for synthesis in prokaryotic systems.

Techniques for in vitro mutagenesis of cloned genes are known. Examples of protocols for site specific mutagenesis may be found in Gustin et al. (1993) Biotechniques 14:22; Barany (1985) Gene 37:111–23; Colicelli et al. (1985) Mol Gen Genet 199:537; and Prentki et al. (1984) Gene 29:303–13. Methods for site specific mutagenesis can be found in Sambrook et al., Molecular Cloning: A Laboratory Manual, CSH Press 1989, pp. 15.3–15.108; Weiner et al., Gene 126:35–41 (1993); Sayers et al. Biotechniques 13:592–6 (1992); Jones and Winistorfer, Biotechniques 12:528–30 (1992); Barton et al., Nucleic Acids Res 18:7349–55 (1990); Marotti and Tomich, Gene Anal Tech 6:67–70 (1989); and Zhu, Anal Biochem 177:1204 (1989). Such mutated genes may be used to study structure-function relationships of Emi1, or to alter properties of the protein that affect its function or regulation.

For use in the methods of the invention, nucleic acids encoding Emi1 may be cDNA or genomic DNA or a fragment thereof. The term Emi1 gene shall be intended to mean the open reading frame, encoding specific Emi1 polypeptides, introns, as well as adjacent 5 and 3 non-coding nucleotide sequences involved in the regulation of expression, up to about 20 kb beyond the coding region, but possibly further in either direction. The gene may be introduced into an appropriate vector for extrachromosomal maintenance or for integration into a host genome. The term cDNA as used herein is intended to include all nucleic acids that share the arrangement of sequence elements found in native mature mRNA species, where sequence elements are exons and 3 and 5 non-coding regions, e.g. SEQ ID NO:18. Normally mRNA species have contiguous exons, with the intervening introns, when present, removed by nuclear RNA splicing, to create a continuous open reading frame encoding a Emi1 protein.

The Emi1 genetic sequence are isolated and obtained in substantial purity, generally as other than an intact chromosome. Usually, the DNA will be obtained substantially free of other nucleic acid sequences that do not include an Emi1 gene sequence or fragment thereof, generally being at least about 50%, usually at least about 90% pure and is typically "recombinant", i.e. flanked by one or more nucleotides with which it is not normally associated on a naturally occurring chromosome.

For use as a hybridization probe or for heteroduplex analysis, the coding sequence or fragments thereof may be used, e.g. sequences that encompass the introduced mutations, that correspond to the *Xenopus* sequence, etc. may be used. Fragments may be obtained of the DNA sequence by chemically synthesizing oligonucleotides in accordance with conventional methods, by restriction enzyme digestion, by PCR amplification, etc. For the most part, DNA fragments will be at least about 25 nt in length, usually at least about 30 nt, more usually at least about 50 nt.

Homologs of Emi1 are identified by any of a number of methods. A fragment of the provided cDNA may be used as a hybridization probe against a cDNA library from the target organism of interest, where low stringency conditions are used. The probe may be a large fragment, or one or more short degenerate primers. Nucleic acids having sequence similarity are detected by hybridization under low stringency conditions, for example, at 50° C. and 10×SSC (0.9 M NaCl/0.09 M sodium citrate) and remain bound when subjected to washing at 55° C. in 1×SSC. Sequence identity may be determined by hybridization under stringent conditions, for example, at 50° C. or higher and 0.1×SSC (9 mM NaCl/0.9 mM sodium citrate). Nucleic acids that are substantially identical to the provided Emi1 sequences, e.g. allelic variants, genetically altered versions of the gene, etc., bind to the provided Emi1 sequences under stringent hybridization conditions. By using probes, particularly labeled probes of DNA sequences, one can isolate homologous or related genes.

genomic sequence of interest comprises the nucleic acid present between the initiation codon and the stop codon, as defined in the listed sequences, including all of the introns that are normally present in a native chromosome. It may further include the 3 and 5 untranslated regions found in the mature mRNA. It may further include specific transcriptional and translational regulatory sequences, such as promoters, enhancers, etc., including about 1 kb, but possibly more, of flanking genomic DNA at either the 5 or 3 end of the transcribed region. The genomic DNA may be isolated as a fragment of 100 kbp or smaller; and substantially free of flanking chromosomal sequence. The genomic DNA flanking the coding region, either 3' or 5', or internal regulatory sequences as sometimes found in introns, contains sequences required for proper tissue and stage specific expression.

The nucleic acid compositions of the subject invention may encode all or a part of the subject polypeptides. Double or single stranded fragments may be obtained of the DNA sequence by chemically synthesizing oligonucleotides in accordance with conventional methods, by restriction enzyme digestion, by PCR amplification, etc. For the most part, DNA fragments will be of at least 15 nt, usually at least 18 nt or 25 nt, and may be at least about 50 nt. Such small DNA fragments are useful as primers for PCR, hybridization screening probes, etc. Larger DNA fragments, i.e. greater than 100 nt are useful for production of the encoded polypeptide.

For use in amplification reactions, such as PCR, a pair of primers will be used. The exact composition of the primer sequences is not critical to the invention, but for most applications the primers will hybridize to the subject sequence under stringent conditions, as known in the art. It is preferable to choose a pair of primers that will generate an amplification product of at least about 50 nt, preferably at least about 100 nt. Algorithms for the selection of primer sequences are generally known, and are available in commercial software packages. Amplification primers hybridize to complementary strands of DNA, and will prime towards each other.

The DNA may also be used to identify expression of the gene in a biological specimen. The manner in which one probes cells for the presence of particular nucleotide sequences, as genomic DNA or RNA, is well established in the literature and does not require elaboration here. DNA or mRNA is isolated from a cell sample. The mRNA may be amplified by RT-PCR, using reverse transcriptase to form a complementary DNA strand, followed by polymerase chain reaction amplification using primers specific for the subject DNA sequences. Alternatively, the mRNA sample is separated by gel electrophoresis, transferred to a suitable support, e.g. nitrocellulose, nylon, etc., and then probed with a fragment of the subject DNA as a probe. Other techniques, such as oligonucleotide ligation assays, in situ hybridizations, and hybridization to DNA probes arrayed on a solid chip may also find use. Detection of mRNA hybridizing to the subject sequence is indicative of Emi1 gene expression in the sample.

DNA-based reagents derived from the sequence of Emi1, e.g. PCR primers, oligonucleotide or cDNA probes, as well as antibodies against human p50 Emi1, are used to screen patient samples, e.g. biopsy-derived tumors, inflammatory samples such as arthritic synovium, etc., for amplified Emi1 DNA, or increased expression of Emi1 mRNA or protein. DNA-based reagents are designed for evaluation of chromosomal loci implicated in certain diseases e.g. for use in loss-of-heterozygosity (LOH) studies, or design of primers based on Emi1 coding sequence.

The subject nucleic acid and/or polypeptide compositions may be used to analyze a patient sample for the presence of polymorphisms associated with a disease state or genetic predisposition to a disease state. Biochemical studies may be performed to determine whether a sequence polymorphism in an Emi1 coding region or control regions is associated with disease, particularly cancers and other growth abnormalities. Diseases of interest may also include restenosis, diabetes, neurological disorders, etc. Disease associated polymorphisms may include deletion or truncation of the gene, mutations that alter expression level, that affect the binding activity of the protein to Cdc20, Cdh1, that affect the ZBR, etc.

Changes in the promoter or enhancer sequence that may affect expression levels of Emi1 can be compared to expression levels of the normal allele by various methods known in the art. Methods for determining promoter or enhancer strength include quantitation of the expressed natural protein; insertion of the variant control element into a vector with a reporter gene such as β-galactosidase, luciferase, chloramphenicol acetyltransferase, etc. that provides for convenient quantitation; and the like.

Emi1 Polypeptides

The subject gene may be employed for producing all or portions of Emi1 polypeptides. For expression, an expression cassette may be employed. The expression vector will provide a transcriptional and translational initiation region, which may be inducible or constitutive, where the coding region is operably linked under the transcriptional control of the transcriptional initiation region, and a transcriptional and translational termination region. These control regions may be native to an Emi1 gene, or may be derived from exogenous sources.

The peptide may be expressed in prokaryotes or eukaryotes in accordance with conventional ways, depending upon the purpose for expression. For large scale production of the protein, a unicellular organism, such as *E. coli, B. subtilis, S. cerevisiae*, insect cells in combination with baculovirus vectors, or cells of a higher organism such as vertebrates, particularly mammals, e.g. COS 7 cells, may be used as the expression host cells. In some situations, it is desirable to express the Emi1 gene in eukaryotic cells, where the Emi1 protein will benefit from native folding and post-translational modifications. Small peptides can also be synthesized in the laboratory. Peptides that are subsets of the complete Emi1 sequence may be used to identify and investigate parts of the protein important for function, such as the zinc-binding domain, the F-box, or to raise antibodies directed against these regions. Peptides may be from about 8 amino acids in length, usually at least about 12 amino acids in length, or 20 amino acids in length, and up to complete domains, or a substantially complete protein, i.e. 90 to 95% of the mature polypeptide.

With the availability of the protein or fragments thereof in large amounts, by employing an expression host, the protein may be isolated and purified in accordance with conventional ways. A lysate may be prepared of the expression host and the lysate purified using HPLC, exclusion chromatography, gel electrophoresis, affinity chromatography, or other purification technique. The purified protein will generally be at least about 80% pure, preferably at least about 90% pure, and may be up to and including 100% pure. Pure is intended to mean free of other proteins, as well as cellular debris.

The expressed Emi1 polypeptides are useful for the production of antibodies, where short fragments provide for antibodies specific for the particular polypeptide, and larger fragments or the entire protein allow for the production of antibodies over the surface of the polypeptide. Antibodies may be raised to the wild-type or variant forms of Emi1. Antibodies may be raised to isolated peptides corresponding to these domains, or to the native protein.

Antibodies are prepared in accordance with conventional ways, where the expressed polypeptide or protein is used as an immunogen, by itself or conjugated to known immunogenic carriers, e.g. KLH, pre-S HBsAg, other viral or eukaryotic proteins, or the like. Various adjuvants may be employed, with a series of injections, as appropriate. For monoclonal antibodies, after one or more booster injections, the spleen is isolated, the lymphocytes immortalized by cell fusion, and then screened for high affinity antibody binding. The immortalized cells, i.e. hybridomas, producing the desired antibodies may then be expanded. For further description, see Antibodies: A Laboratory Manual, Harlow and Lane eds., Cold Spring Harbor Laboratories, Cold Spring Harbor, N.Y., 1988. If desired, the mRNA encoding the heavy and light chains may be isolated and mutagenized by cloning in *E. coli*, and the heavy and light chains mixed to further enhance the affinity of the antibody. Alternatives to in vivo immunization as a method of raising antibodies include binding to phage display libraries, usually in conjunction with in vitro affinity maturation.

Compound Screening and Drug Design

The availability of a number of components in the APC pathway allows in vitro reconstruction of the physiological events. Two or more of the components may be combined in vitro, and the behavior assessed in terms of activation of the ubiquitin ligase; modification of protein components, e.g. proteolytic processing, phosphorylation, ubiquitylation, etc.; ability of different protein components to bind to each other; the destruction of cyclins A and B, securin and geminin during normal cell cycle; to block cellular exit from mitosis; to block oocyte activation, to regulate entry into S phase, etc. The components may be modified by sequence deletion, substitution, etc. to determine the functional role of specific domains.

Drug screening may be performed using an in vitro model, a genetically altered cell or animal, or purified Emi1 protein, including the mutations and isolated domains previously described. One can identify ligands or substrates that bind to, modulate or mimic the action of Emi1. Areas of investigation include the development of treatments for hyper-proliferative disorders, e.g. cancer, restenosis, osteoarthritis, metastasis, etc.; for development of agents that modulate fertilization and oocyte activation, and the like. Of particular interest are compounds that affect microtubule assembly and spindle formation during mitosis, e.g. taxanes, vinca alkaloids, cytochalasin, and the like.

BJ fibroblasts and U2OS tetracycline-inducible cell lines were passaged and harvested for Northern and Western blots as described (Lukas et al. (1999) *Nature* 401:815–818). U2OS cells stably expressed fusion proteins of the estrogen receptor (ER) with the transcription factors E2F-1 or E2F-3. Experiments involving quantitative reverse-transcriptase polymerase chain reaction (RT-PCR) were performed as described (Muller et al. (2001) *Genes Dev.* 15:267–285). The primer sequences for hEmi1 were as follows: (SEQ ID NO:19) 5'-GTA GAT CGG GAG GAG AGG-3' (forward) and (SEQ ID NO:20) 5'-CAA CTG GCT TTG AGG-3' (reverse).

Regarding the Emi1 zinc-binding region in particular, the specific geometry of zinc coordination offers a high degree of structure predictability. The possibility of the rational design of compounds directed toward this zinc binding center permits the directed design of Emi1 inhibitors. The possibility of using zinc coordinating scaffolds also allows for the rational design of Emi1 mimetic compounds.

The term "agent" as used herein describes any molecule, e.g. protein or pharmaceutical, with the capability of altering or mimicking the physiological function of Emi1. Generally a plurality of assay mixtures are run in parallel with different agent concentrations to obtain a differential response to the various concentrations. Typically one of these concentrations serves as a negative control, i.e. at zero concentration or below the level of detection.

Candidate agents encompass numerous chemical classes, though typically they are organic molecules, preferably small organic compounds having a molecular weight of more than 50 and less than about 2,500 daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof.

Candidate agents are obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

Assays of interest may combine or compare the effect of an agent on one or more variants of Emi1, for example the isolated ZBR, the F-box region, the degradation resistant variants, etc. to determine the specificity of action on one or more of these domains and functional motifs. For example, expression constructs comprising Emi1 sequences and variants may be introduced into cell lines under conditions that allow expression. The level of Emi1 activity is determined by a functional assay, immunoassay, etc. and the effect on mitosis, binding of Cdh1 or Cdc20, etc. is determined. A functional assay of interest detects destruction of cyclins A and B, securin and geminin during normal cell cycle. Alternatively, candidate agents are added to a cell that lacks functional Emi1, and screened for the ability to reproduce Emi1 in a functional assay.

The compounds having the desired pharmacological activity may be administered in a physiologically acceptable carrier to a host for treatment of cancer, etc. The inhibitory agents may be administered in a variety of ways, orally, topically, parenterally e.g. subcutaneously, intraperitoneally, by viral infection, intravascularly, etc. Depending upon the manner of introduction, the compounds may be formulated in a variety of ways. The concentration of therapeutically active compound in the formulation may vary from about 0.1–10 wt %.

The compounds of this invention can be incorporated into a variety of formulations for therapeutic administration. Particularly, agents that modulate Emi1 activity, or Emi1 polypeptides and analogs thereof are formulated for administration to patients for the treatment of hyperproliferative disorders. More particularly, the compounds of the present invention can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments, solutions, suppositories, injections, inhalants, gels, microspheres, and aerosols. As such, administration of the compounds can be achieved in various ways, including oral, buccal, rectal, parenteral, intraperitoneal, intradermal, transdermal, intracheal, etc., administration. The Emi1 may be systemic after administration or may be localized by the use of an implant that acts to retain the active dose at the site of implantation.

The compounds of the present invention can be administered alone, in combination with each other, or they can be used in combination with other known compounds. In pharmaceutical dosage forms, the compounds may be administered in the form of their pharmaceutically acceptable salts, or they may also be used alone or in appropriate association, as well as in combination with other pharmaceutically active compounds.

Modulation of Gene Expression

From a therapeutic point of view, affecting Emi1 activity has a therapeutic effect on a number of proliferative disorders, including inflammation, restenosis, and cancer. Inhibition of Emi1 delays cyclin B accumulation and mitotic entry, while stabilization of Emi1 promotes mitotic entry, S phase entry, and prevents oocyte activation. Antisense Emi1 sequences may be administered to inhibit expression. Pseudo-substrate inhibitors, for example, a peptide that mimics a substrate for Emi1 may be used to inhibit activity. Other inhibitors are identified by screening for biological activity in an Emi1-based functional assay, e.g. in vitro or in vivo ubiquitin ligase inhibition activity.

Expression vectors may be used to introduce the Emi1 gene into a cell. Such vectors generally have convenient restriction sites located near the promoter sequence to provide for the insertion of nucleic acid sequences. Transcription cassettes may be prepared comprising a transcription initiation region, the target gene or fragment thereof, and a transcriptional termination region. The transcription cassettes may be introduced into a variety of vectors, e.g. plasmid; retrovirus, e.g. lentivirus; adenovirus; and the like, where the vectors are able to transiently or stably be maintained in the cells, usually for a period of at least about one day, more usually for a period of at least about several days to indefinitely.

The gene or Emi1 protein may be introduced into tissues or host cells by any number of routes, including viral infection, microinjection, or fusion of vesicles. Jet injection may also be used for intramuscular administration, as described by Furth et al. (1992) Anal Biochem 205:365–368. The DNA may be coated onto gold microparticles, and delivered intradermally by a particle bombardment device, or "gene gun" as described in the literature (see, for example, Tang et al. (1992) Nature 356:152–154), where gold microprojectiles are coated with the Emi1 or DNA, then bombarded into skin cells.

Antisense molecules can be used to down-regulate expression of Emi1 in cells. The anti-sense reagent may be antisense oligonucleotides (ODN), particularly synthetic ODN having chemical modifications from native nucleic acids, or nucleic acid constructs that express such anti-sense molecules as RNA. The antisense sequence is complementary to the mRNA of the targeted gene, and inhibits expression of the targeted gene products. Antisense molecules inhibit gene expression through various mechanisms, e.g. by reducing the amount of mRNA available for translation, through activation of RNAse H, or steric hindrance. One or a combination of antisense molecules may be administered, where a combination may comprise multiple different sequences.

Antisense molecules may be produced by expression of all or a part of the target gene sequence in an appropriate vector, where the transcriptional initiation is oriented such that an antisense strand is produced as an RNA molecule. Alternatively, the antisense molecule is a synthetic oligonucleotide. Antisense oligonucleotides will generally be at least about 7, usually at least about 12, more usually at least about 20 nucleotides in length, and not more than about 500, usually not more than about 50, more usually not more than about 35 nucleotides in length, where the length is governed by efficiency of inhibition, specificity, including absence of cross-reactivity, and the like. It has been found that short oligonucleotides, of from 7 to 8 bases in length, can be strong and selective inhibitors of gene expression (see Wagner et al. (1996) Nature Biotechnology 14:840–844).

A specific region or regions of the endogenous sense strand mRNA sequence is chosen to be complemented by the antisense sequence. Selection of a specific sequence for the oligonucleotide may use an empirical method, where several candidate sequences are assayed for inhibition of expression of the target gene in vitro or in an animal model. A combination of sequences may also be used, where several regions of the mRNA sequence are selected for antisense complementation.

Antisense oligonucleotides may be chemically synthesized by methods known in the art (see Wagner et al. (1993) supra. and Milligan et al., supra.) Preferred oligonucleotides are chemically modified from the native phosphodiester structure, in order to increase their intracellular stability and binding affinity. A number of such modifications have been described in the literature, which alter the chemistry of the backbone, sugars or heterocyclic bases.

Among useful changes in the backbone chemistry are phosphorothioates; phosphorodithioates, where both of the non-bridging oxygens are substituted with sulfur; phosphoroamidites; alkyl phosphotriesters and boranophosphates. Achiral phosphate derivatives include 3'-O-5'-S-phosphorothioate, 3'-S'-5-O-phosphorothioate, 3'-CH$_2$-5'-O-phosphonate and 3'-NH-5'-O-phosphoroamidate, and morpholinos. Peptide nucleic acids replace the entire ribose phosphodiester backbone with a peptide linkage. Sugar modifications are also used to enhance stability and affinity. The ($\alpha$-anomer of deoxyribose may be used, where the base is inverted with respect to the natural $\beta$-anomer. The 2'-OH of the ribose sugar may be altered to form 2'-O-methyl or 2'-O-allyl sugars, which provides resistance to degradation without comprising affinity. Modification of the heterocyclic bases must maintain proper base pairing. Some useful substitutions include deoxyuridine for deoxythymidine; 5'-methyl-2'-deoxycytidine and 5'-bromo-2'-deoxycytidine for deoxycytidine. 5'-propynyl-2'-deoxyuridine and 5'-propynyl-2'-deoxycytidine have been shown to increase affinity and biological activity when substituted for deoxythymidine and deoxycytidine, respectively.

Genetically Altered Cell or Animal Models for Emi1 Function

The subject nucleic acids can be used to generate transgenic animals or site specific gene modifications in cell lines. Transgenic animals may be made through homologous recombination, where the normal Emi1 locus is altered. Alternatively, a nucleic acid construct is randomly integrated into the genome. Vectors for stable integration include plasmids, retroviruses and other animal viruses, YACs, and the like.

The modified cells or animals are useful in the study of Emi1 function and regulation. For example, a series of small deletions and/or substitutions may be made in the Emi1 gene to determine the role of different exons in specific binding to Cdc20 and Cdh1 proteins, to block the destruction of cyclins A and B, securin and geminin during normal cell cycle; and to block cellular exit from mitosis. Emi1 binds the APC activators Cdc20 and Cdh1 and Emi1 blocks APC activation by Cdc20 or Cdh1, etc. Of interest are the uses of Emi1 to construct transgenic animal models for cancer and/or other hyperproliferative disorders, where expression of Emi1 is specifically reduced or absent. Specific constructs of interest include anti-sense Emi1, which will block Emi1 expression and expression of dominant negative Emi1 mutations. A detectable marker, such as lac Z may be introduced into the Emi1 locus, where upregulation of Emi1 expression will result in an easily detected change in phenotype.

One may also provide for expression of the Emi1 gene or variants thereof in cells or tissues where it is not normally expressed or at abnormal times of development. By providing expression of Emi1 protein in cells in which it is not normally produced, one can induce changes in cell behavior, e.g. through Emi1 mediated LEK-1 activity.

DNA constructs for homologous recombination will comprise at least a portion of the Emi1 gene with the desired genetic modification, and will include regions of homology to the target locus. The regions of homology may include coding regions, or may utilize intron and/or genomic sequence. DNA constructs for random integration need not include regions of homology to mediate recombination. Conveniently, markers for positive and negative selection are included. Methods for generating cells having targeted gene modifications through homologous recombination are known in the art. For various techniques for transfecting mammalian cells, see Keown et al. (1990) Methods in Enzymology 185:527–537.

For embryonic stem (ES) cells, an ES cell line may be employed, or embryonic cells may be obtained freshly from a host, e.g. mouse, rat, guinea pig, etc. Such cells are grown on an appropriate fibroblast-feeder layer or grown in the presence of leukemia inhibiting factor (LIF). When ES or embryonic cells have been transformed, they may be used to produce transgenic animals. After transformation, the cells are plated onto a feeder layer in an appropriate medium. Cells containing the construct may be detected by employing a selective medium. After sufficient time for colonies to grow, they are picked and analyzed for the occurrence of homologous recombination or integration of the construct. Those colonies that are positive may then be used for embryo manipulation and blastocyst injection. Blastocysts are obtained from 4 to 6 week old superovulated females. The ES cells are trypsinized, and the modified cells are injected into the blastocoel of the blastocyst. After injection, the blastocysts are returned to each uterine horn of pseudopregnant females. Females are then allowed to go to term and the resulting offspring screened for the construct. By providing for a different phenotype of the blastocyst and the genetically modified cells, chimeric progeny can be readily detected.

The chimeric animals are screened for the presence of the modified gene and males and females having the modification are mated to produce homozygous progeny. If the gene alterations cause lethality at some point in development, tissues or organs can be maintained as allogeneic or congenic grafts or transplants, or in culture. The transgenic animals may be any non-human mammal, such as laboratory animals, domestic animals, etc. The transgenic animals may be used in functional studies, drug screening, etc., e.g. to determine the effect of a candidate drug on oncogenesis, down regulation of E-cadherin, up regulation of LEF-1, etc.

Experimental

The following examples are put forth so as to provide those of ordinary skill in the art with a complete disclosure and description of how to make and use the subject invention, and are not intended to limit the scope of what is regarded as the invention. Efforts have been made to ensure accuracy with respect to the numbers used (e.g. amounts, temperature, concentrations, etc.) but some experimental errors and deviations should be allowed for. Unless otherwise indicated, parts are parts by weight, molecular weight is average molecular weight, temperature is in degrees centigrade; and pressure is at or near atmospheric.

EXAMPLE 1

Figure 1A:
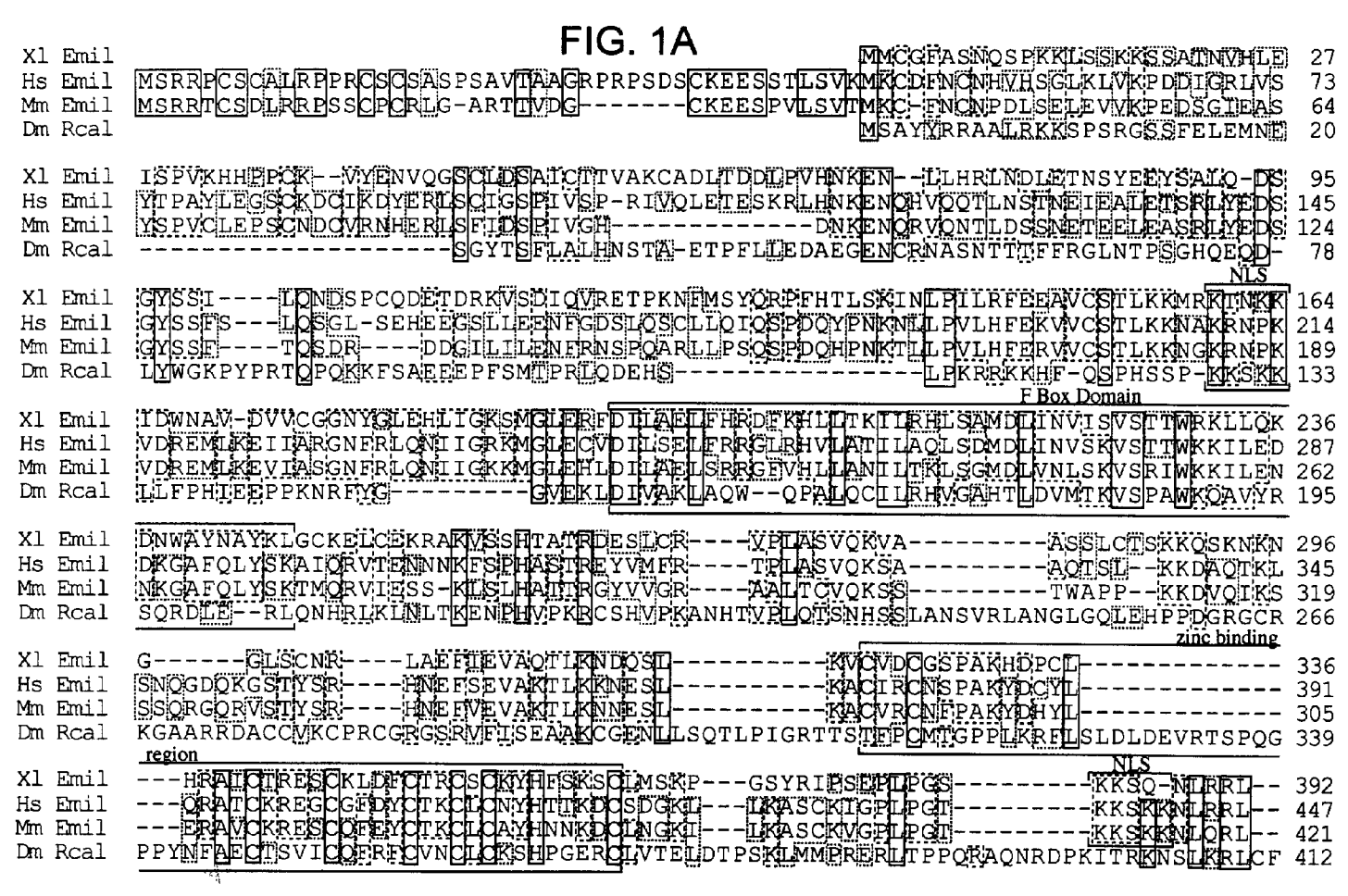
Figure 1B:
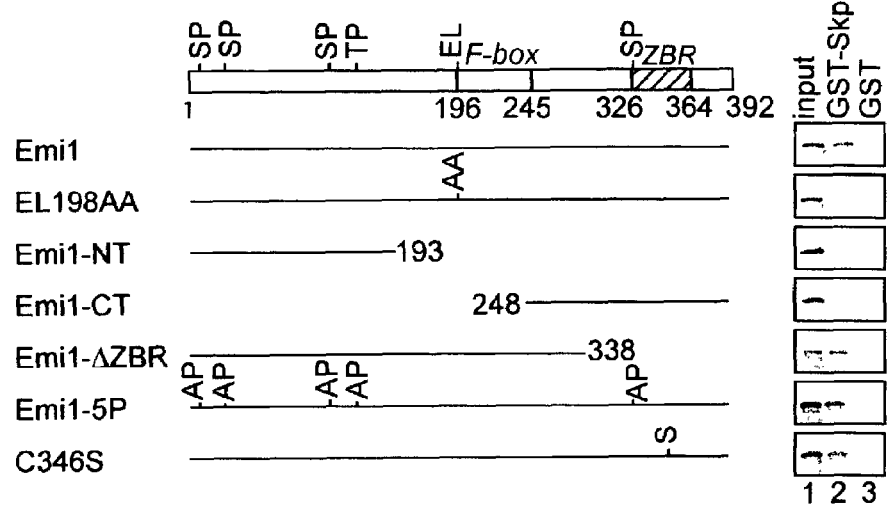
FIGS. 1B to 1C show the schematic genetic structure of wild-type and mutated Emi1, and the specificity of anti-Emi1 antibodies. A. Clustal W alignment of Emi1 and homologs. Xl, *Xenopus laevis*; Dm, *Drosophila melanogaster*; Hs, *Homo sapiens*; Mm, *Mus musculus*. Black=identity, dark gray=highly conserved, light gray=less highly conserved. The F-box, zinc-binding region (ZBR), and possible NLS sequences are boxed. B. Emi1 protein (accession # AF319594) schematic, key features, and variant proteins. Emi1=wild type; EL198AA=mutated in 2 conserved F-box residues; Emi1-N-terminus (NT)=amino acids 1–193; Emi1-C-terminus (CT)=amino acids 248–392; Emi1-ΔZBR=amino acids 1–338; Emi1-5P=substitution of alanine for serine or threonine in all five SP/TP sites; C346S=substitution of cysteine 346 with serine. GST-Skp1 or GST was incubated with $^{35}$S-labeled in vitro translated (IVT) proteins, bound to glutathione agarose, and analyzed by SDS-PAGE and autoradiography (right). C. Characterization of Emi1 antibodies. Rabbit reticulocyte lysate (RRL) programmed with Emi1 (lane 1), unprogrammed RRL (lane 2), *Xenopus* XTC cell lysate (lane 3), and interphase *Xenopus* egg extract (lane 4) were resolved by SDS-PAGE and immunoblotted with affinity purified anti-Emi1 or MBP-Emi1 blocked antibodies.

*Xenopus* Emi1 is a cell cycle regulated protein related to *Drosophila* Regulator of cyclin A (Rca1). Emi1 was initially isolated in a yeast two-hybrid screen for Skp1 binding proteins. The full-length *Xenopus* Emi1 oocyte cDNA was cloned. The predicted Emi1 protein is 392 residues long with an F-box, a zinc-binding region (ZBR), and five possible Cdk phosphorylation sites (FIGS. 1A and 1B). There are two potential nuclear localization sequences. BLAST search revealed that Emi1 has homology to the *Drosophila* protein Rca1 (FIG. 1A). Emi1 and Rca1 are similar in size, placement of functional domains, and share 25% similarity (16% identity). Emi1 is 43% similar (35% identical) to human Fbx5, a recently identified F-box protein of unknown function Cenciarelli et al. (1999) *Current Biology* 9:1177–9. Mutation or deletion of the Emi1 F-box abrogates binding to Skp1 in vitro (FIG. 1B).

*Xenopus* Emi1 and its homologs contain 8 cysteines and a histidine in the C-terminus that are highly conserved and may comprise two zinc-binding domains (FIG. 4). The spacing of the cysteines and histidine in Emi1/Rca1, C-x(2)-C-x(14-30)-C-x(4)-C-x(4)-C-x(2)-C-x(4)-H-x(4)-C, is similar but not identical to the recently described DRIL (TRIAD) cysteine-rich motif.

Figure 1C:
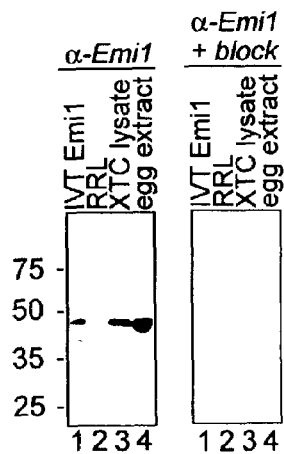

Affinity purified antibodies against *Xenopus* Emi1 recognize a protein of the expected molecular mass (44 kDa) in egg extracts and *Xenopus* XTC lysates, which is blocked by preincubation of the antibodies with Emi1 protein (FIG. 1C). Antibodies also recognize in vitro translated (IVT) Emi1, but fail to detect a protein in unprogrammed reticulocyte lysate.

Figure 2A:
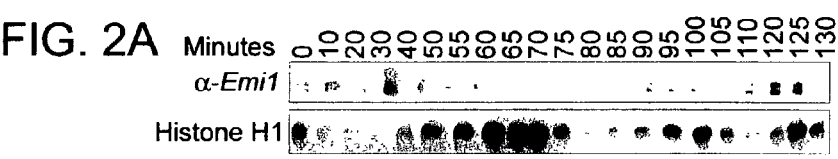
FIG. 2A shows that emi1 levels fluctuate in the embryonic cell cycle; and is ubiquitylated in mitosis in cycling extracts (FIG. 2B). Emi1 destruction is APC independent in the egg (FIG. 2C). In mitotic extracts, Emi1 and its N-terminus are unstable; the C-terminus is stable (FIGS. 2C and 2D). Mutation of the cyclin/Cdk sites stabilizes Emi1 (FIG. 2E). Emi1 is a cyclin B/Cdc2 susbtrate in vitro (FIG. 2E). A. Emi1 levels fluctuate in the embryonic cell cycle. Fertilized eggs were incubated at 23 C, equal numbers of embryos removed at the indicated times, and processed for immuno- blotting with anti-Emi1 antibodies (upper panel) and for histone H1 kinase activity of immunoprecipitated cyclin B1 (lower panel). B. Emi1 is ubiquitylated in cycling extracts. Left panel: Activated $Xenopus$ cycling egg extracts with added $^{35}$S-labeled IVT Emi1 were incubated at 23. Aliquots were removed at the indicated times and analyzed by SDS-PAGE and autoradiography. I=interphase, M=mitosis, as determined by cyclin B ubiquitylation and Histone H1 kinase activity. Right panel: Interphase and mitotic extract with added FLAG-tagged ubiquitin were incubated (23 C, 60 min), immunoprecipitated with anti-Emi1 sera, and ana- lyzed by immunoblotting for FLAG-ubiquitin. *=IgG band. C. Emi1 destruction does not require the APC. $^{35}$S-labeled IVT Emi1 or N-terminal cyclin B fragment was added to Δ90 extracts treated with either destruction box (D-box) peptide, scrambled peptide (control), or depleted of the APC with anti-Cdc27 antibodies. Aliquots were removed at the indicated times and analyzed by SDS-PAGE and autorad- iography. D. In mitotic extracts, Emi1 and its N-terminus are unstable; the C-terminus is stable. $^{35}$S-labeled IVT full- length, N-terminal, or C-terminal Emi1 was added to Δ90 extracts and assayed for stability as in C. E. Mutation of the five possible Cdk phosphorylation sites stabilizes Emi1. $^{35}$S-labeled IVT wild type Emi1 or a mutant in all five SP/TP sites (Emi1-5P) was added to Δ90 extracts and assayed for stability as in C (left). Equimolar amounts of purified MBP-Emi1, MBP-Emi1-NT, MBP-Emi1-CT, or MBP-Emi1-5P were incubated with purified cyclin B/Cdc2 in the presence of [$^{32}$P]-γATP. Proteins were analyzed by SDS-PAGE and autoradiography (right).

Emi1 protein levels oscillate in a cell cycle-dependent manner. We examined the Emi1 protein in the cell cycle of the early embryo. In fertilized eggs, Emi1 levels increase in S phase and decrease in M phase (FIG. 2A). Emi1 is present in CSF arrested eggs and persists after fertilization through the longer first interphase, during pronuclear migration.

Figure 2B:
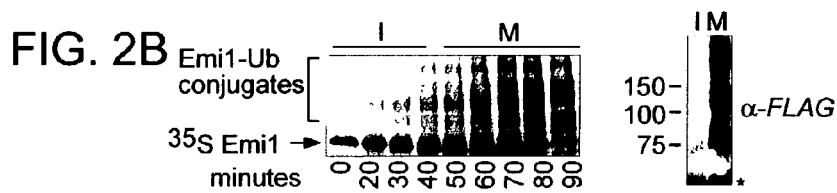

Extracts made from activated eggs reproduce cell cycle events in vitro. Both endogenous Emi1 and exogenous IVT Emi1 added to these extracts are ubiquitylated in mitosis (FIG. 2B). Emi1 destruction requires the proteasome because IVT- Emi1 is stabilized when the proteasome inhibitor MG-132 is added to mitotic egg extracts.

Figure 2C:
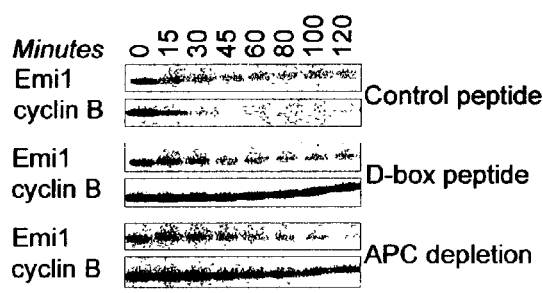

Because Emi1 is mitotically destroyed, we tested whether it is an APC substrate. IVT Emi1 or an N-terminal cyclin B fragment was incubated in *Xenopus* egg extracts stabilized in mitosis by addition of nondestructable cyclin B (Δ90). In these Δ90 extracts, the APC is active and cyclin B is degraded. IVT Emi1 protein is destroyed in Δ90 extracts, but not interphase-arrested extracts. APC immunodepletion or addition of a peptide containing the cyclin B destruction box, known to inhibit APC-mediated proteolysis, prevented cyclin B destruction, whereas a control peptide did not (FIG. 2C). However, Emi1 was destroyed with similar kinetics whether the APC was depleted, blocked by destruction box peptides, or a control peptide (FIG. 2C). Thus, Emi1 does not appear to be an APC substrate in the egg.

Figure 2D:
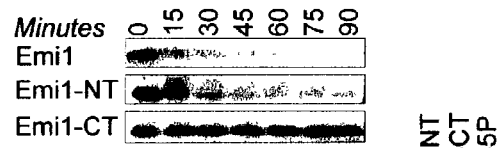
Figure 2E:
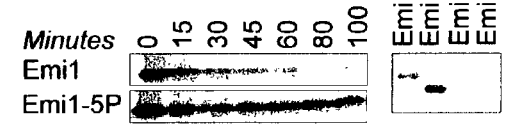

To investigate the sequence requirements for Emi1 destruction, we constructed N or C-terminal Emi1 fragments (FIG. 1B). IVT Emi1 N-terminus (Emi1-NT) was destroyed with kinetics similar to full-length Emi1 in Δ90 extracts ($t_{1/2}$~10 minutes), whereas the C-terminus (Emi1-CT) was stable ($t_{1/2}$>100 minutes; FIG. 2D). Because the N-terminus contains four of five possible Cdk phosphorylation sites in Emi1, we mutated serine or threonine to alanine in all five sites and found that this Emi1-5P mutant was stable in Δ90 extracts compared to wild type (FIG. 2E). Interestingly, the N-terminus of Emi1 identified Xenopus cyclins B1 and B2 as interacting proteins several times in a yeast two-hybrid screen. Full-length Emi1 and Emi1-NT were efficient in vitro cyclin B/Cdc2 substrates, although neither the Emi1-CT nor Emi1-5P mutants were phosphorylated (FIG. 2E). Further, Emi1 binds the mitotic cyclins A and B in vitro and Emi1 is a phosphoprotein in egg extracts. Thus, the data suggests that phosphorylation of Emi1 by mitotically active kinases triggers the APC-independent destruction of Emi1.

Emi1 inhibits APC activity in Xenopus egg extracts. The oscillation of Emi1 in Xenopus embryos and the G2 arrest seen in Rca1-deficient Drosophila embryos, suggested that like cyclin B, Emi1 accumulation may be important for mitotic entry and that Emi1 destruction may be necessary for mitotic exit. To test whether Emi1 destruction is required for mitotic exit, we analyzed the effect of Emi1 addition to Xenopus extracts. Addition of purified MBP-Emi1 protein to cycling extracts prevented the destruction of endogenous cyclins A and B and mitotic exit (FIG. 3A). Addition of equimolar amounts of MBP or another Xenopus F-box protein had no effect on cyclin B stability or mitosis. Excess Emi1 did not affect the timing of mitotic entry or MPF activation in egg extracts, as analyzed by DNA morphology (FIG. 3A) or cyclin B/Cdc2 kinase activity (FIG. 3B). By quantitative immunoblotting, we estimate Emi1 to be ~300 nM in interphase egg extracts. As little as 100 nM additional Emi1 protein stabilizes cyclins A and B. However, we see a stronger delay between cyclin B/Cdc2 activation and cyclin B destruction with 300 nM to 1 μM Emi1 protein concentrations, likely because Emi1 is itself destroyed in mitosis.

We found that Emi1 also inhibits the destruction of two other known APC substrates, securin and geminin, in Δ90 extracts (FIG. 3C). To test whether Emi1 directly affects APC substrate ubiquitylation, we measured cyclin B ubiquitylation in Δ90 extracts treated with purified MBP or MBP-Emi1 protein. Addition of MBP-Emi1 strongly reduced the ubiquitylation of an iodinated amino-terminal fragment of cyclin B containing the destruction box, whereas MBP did not (FIG. 3D).

To determine which domains of Emi1 are required to block cyclin B destruction, we tested several Emi1 mutants (schematic, FIG. 1B). Cyclin B was destroyed in Δ90 extracts treated with buffer (control) or an MBP-Emi1-NT fusion protein, but was stabilized in the presence of MBP fusions to wild type Emi1, Emi1-5P, the F-box mutant (EL198AA), or Emi1-CT (FIGS. 3E and 3F). Therefore, the Cdk sites, the F-box, and the region N-terminal to the F-box are not required for Emi1 to stabilize cyclin B; however, the C-terminus is both necessary and sufficient. An Emi1 truncation mutant missing the C-terminal ZBR (Emi1-ΔZBR) was incapable of stabilizing cyclin B (FIG. 3F). Further, mutation of conserved ZBR residue cysteine 341 (C341S) or cysteine 346 (C346S) to serine greatly reduced the ability of Emi1 to inhibit cyclin B destruction (FIG. 3G). Thus, the ZBR is necessary for Emi1 to inhibit APC activity.

Emi1 inhibits mitotic exit in vivo. To test whether Emi1 affects the cell cycle in vivo, we injected the protein into one blastomere of a two-cell stage Xenopus embryo. Emi1 caused a stable cell cycle arrest in the injected blastomere, whereas the uninjected blastomere continued to divide normally (FIG. 3H). Embryos injected with Emi1 in both blastomeres had a high level of histone H1 kinase activity similar to that detected in Δ90 extracts, whereas uninjected and control-injected embryos had H1 kinase levels similar to interphase extracts (FIG. 3H). As in cycling extracts, the Emi1 C-terminus with an intact ZBR was also necessary and sufficient to mediate the mitotic block in vivo and wild type and N-terminal Emi1 are unstable in vivo (FIG. 3H and data not shown). In summary, Emi1 blocks the cell cycle at mitosis both in vitro and in vivo and prevents the ubiquitin-mediated destruction of known APC substrates in vitro.

Emi1 overexpression in somatic cells causes a mitotic block. To examine Emi1 subcellular localization, we stained Xenopus XTC cells with affinity purified antibodies to Emi1. In interphase, the protein localizes in a punctate pattern in the nucleus and the cytoplasm, with some perinuclear concentration (FIG. 4A). In mitotic cells, Emi1 localized throughout the cell and particularly at the spindle (FIGS. 4A and 4B).

Because Emi1 can stabilize several APC substrates, which are each destroyed at specific times in mitosis, we tested more precisely when in mitosis Emi1 blocks by overexpressing epitope-tagged Emi1 variants in somatic cells. Because Emi1 is unstable in mitotic XTC cells, the myc-tagged Emi1 variants were cotransfected with a GFP expression construct to mark transfected cells. Transfection of wild type Emi1, EL198AA, Emi1-5P, or Emi1-CT caused an increase in mitotic index compared to vector, whereas neither Emi1-NT nor the C346S point mutant had a significant effect (FIG. 4C). The mitotic block was confirmed by flow cytometric analysis of DNA content (FIG. 4D). The stable Emi1 mutants (Emi1-CT and Emi1-5P) caused a stronger mitotic delay than the unstable wild type Emi1. Overexpression of the APC inhibitor Mad2 in XTC cells caused a mitotic index increase similar to Emi1.

DNA and spindle morphology examination revealed that cells transfected with Emi1, EL198AA, Emi1-5P, or Emi1-CT accumulated predominantly in prometaphase (FIGS. 4E and 4F). Cyclin A destruction (which is blocked by Emi1), occurs in prometaphase and cyclin A overexpression causes a prometaphase delay in human cells and in XTC cells. In contrast, Mad2 does not stabilize cyclin A and blocks predominantly in metaphase when transfected into XTC cells.

Emi1 depletion prevents cyclin B accumulation and mitotic entry. If Emi1 normally inhibits APC activity in interphase, then Emi1 depletion from cycling egg extracts might block cyclin B accumulation and prevent mitotic entry. Following Emi1 immunodepletion (FIG. 5D), we examined cyclin B accumulation and DNA morphology as markers of mitotic entry. In cycling extracts, cyclin B normally peaks by 80 minutes and is destroyed by 120 minutes. In Emi1-depleted extracts, cyclin B levels fail to accumulate (FIG. 5A). Addition of beads from the Emi1 immunodepletion rescued the accumulation and subsequent destruction of cyclin B. Addition of 300 nM purified Emi1 protein rescued cyclin B accumulation but blocked its destruction (FIG. 5A). This is likely because excess Emi1 is not completely destroyed, thus inhibiting the APC and stabilizing cyclin B.

The effect of Emi1 depletion on mitosis was verified by examining DNA morphology in cycling extracts. In control extracts, demembranated sperm DNA was highly condensed by 60 minutes, indicating onset of mitosis, and typically displayed anaphase or telophase morphology by 90 minutes (FIGS. 5B and 5C). In Emi1-depleted extracts, nuclei remained intact with DNA decondensed (FIGS. 5B and 5C). Addition of undepleted extract or purified Emi1 to Emi1-depleted extracts rescued mitotic entry. Although Emi1-depleted extracts rescued with undepleted extract progressed past metaphase, extracts rescued with Emi1 protein did not, presumably because Emi1 blocks APC-dependent securin destruction and thus sister chromatid separation.

If Emi1 depletion prematurely activates the APC, then addition of the APC inhibitor Mad2 should also rescue mitotic entry. Mad2 addition to Emi1-depleted extracts did rescue mitotic entry (FIGS. 5B and 5C) although much like rescue with Emi1 protein, the extracts did not progress beyond metaphase. To test whether the inability of Emi1-depleted extracts to enter mitosis was primarily due to their failure to accumulate cyclin B, we also tested whether nondestructable Δ90 cyclin B addition rescued mitotic entry. Δ90 addition to depleted extracts rescued nuclear envelope breakdown and mitotic DNA condensation, indicating that nondestructable cyclin B can overcome the requirement for Emi1 in mitotic entry (FIGS. 5B and 5C).

Emi1 interacts with the APC activator Cdc20. To better understand how Emi1 controls APC activity, we looked for interacting proteins by yeast two-hybrid screens of a *Xenopus* oocyte library using Emi1 as the bait. Screening with full-length Emi1 identified only Skp1, therefore we tested Emi1-NT and Emi1-CT for interacting proteins as well (see Experimental Procedures). As previously mentioned, the Emi1-NT bait identified cyclin B.

Importantly, Emi1-NT also identified the APC activator Cdc20. To validate this interaction, we took several approaches. First, Emi1 and Cdc20 co-immunoprecipitate from egg extracts (FIG. 6A). This interaction appears to be APC independent, since we were unable to detect the APC subunit APC2 in the precipitate. Second, interphase extracts separated on a sucrose gradient or gel filtration column showed that Emi1 and Cdc20 cofractionate (FIGS. 6B and 6C). Emi1 is found in two higher molecular weight pools, ~100–200 kDa and ~300–500 kDa. Cdc20 cofractionates in the ~100–200 kDa complex and Cdc20 co-immunoprecipitates with Emi1 from these fractions (FIG. 6C). The Cdc20 protein that does not co-fractionate with Emi1 co-fractionates with the ~1.5 MDa APC complex (FIG. 6B); however, Cdc20 binds weakly to the inactive interphase APC. Interestingly, a slower migrating form of Cdc20 is consistently seen in some of the fractions containing Emi1. We can also reconstitute the interaction between Emi1 and Cdc20 with baculovirus or using purified proteins (FIGS. 6D and 6F), further supporting a direct interaction.

Emi1 can block Cdc20-dependent APC activation in vitro. If Emi1 inhibits Cdc20 activation of the APC, then Cdc20 protein should rescue the Emi1 block to cyclin B destruction. Baculovirus-expressed Cdc20 addition to mitotic extracts rescued the Emi1-induced block to cyclin B destruction in a dose-dependent manner (FIG. 6E), supporting the hypothesis that Emi1 prevents Cdc20 from activating the APC. This result also indicates that the APC is competent for activation by Cdc20 even when Emi1 is present, reinforcing our other observations that Emi1 does not directly inhibit the APC enzymatic complex.

We knew that the Emi1 N-terminus interacts with Cdc20 from our two-hybrid screen, but the C-terminus of Emi1 (Emi1-CT) also bound Cdc20 in vitro (FIG. 6F). We confirmed the Cdc20-Emi1-CT interaction in the yeast two-hybrid system. Interestingly, we also observed both in yeast two-hybrid and in vitro binding assays, that the Cdc20 N-terminus from residues 1–158, but not the WD repeat domain, is sufficient for binding to Emi1. Because the C-terminal ZBR is required for Emi1 to inhibit APC activity, we tested the ability of C-terminal Emi1 fragments to bind the Cdc20 N-terminus. A C-terminal subfragment containing the most conserved region of the ZBR, GST-Emi1-CTZBR (residues 335–364), interacts with the Cdc20-NT, whereas the C-terminal fragment without the ZBR, GST-Emi1-CTΔZBR (residues 248–334), does not (FIG. 6F).

We utilized this binding information to test whether the interaction between Emi1 and Cdc20 is required for Emi1 to inhibit Cdc20 from activating the APC in a reconstituted system. Addition of full-length Emi1 protein prevented Cdc20 from activating APC immunopurified from mitotic egg extract in a dose-dependent fashion (FIG. 6G). The Emi1 C-terminus, which contains the ZBR, is sufficient to inhibit cyclin B ubiquitylation in this purified system whereas the Emi1-CTΔZBR, which fails to bind Cdc20, does not inhibit.

Figures 7A, 7B:
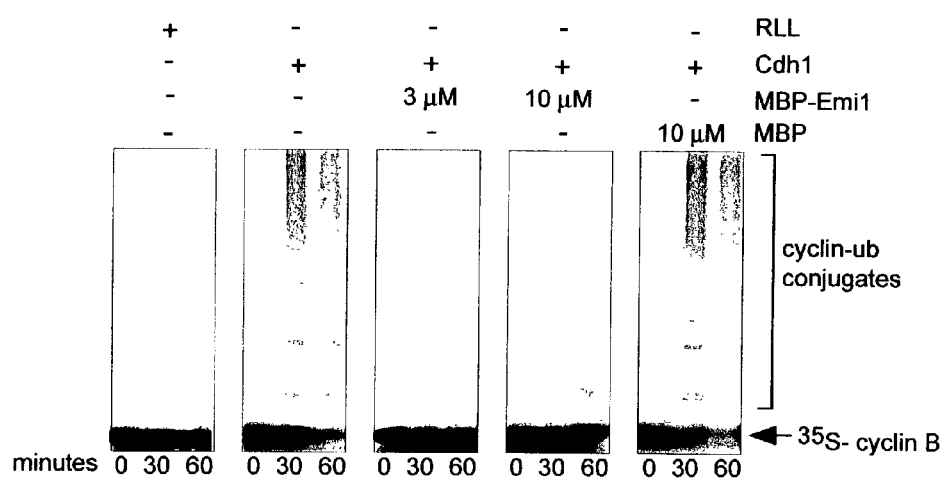
FIG. 7A to 7B show that Emi1p interacts with Cdh1 and inhibits APC activation by Cdh1. A. Emi1 interacts with Cdh1 in vitro. Purified GST-Emi1 or GST protein was incubated with $^{35}$S-labeled in vitro translated (IVT) Cdh1, bound to glutathione agarose, and analyzed by SDS-PAGE and autoradiography. B. Inhibition of Cdh1-mediated activation of the APC by Emi1. IVT Cdh1 or rabbit reticulocyte lysate (RLL) was incubated for 30 min with buffer or purified bacterially expressed 3 µM MBP-Emi1, 10 µM MBP-Emi1, or 10 µM MBP. APC was immunopurified from interphase egg extracts with anti-Cdc27 beads, then incubated with the Cdh1/protein mixtures for 1 hr. APC beads were washed, and assayed for cyclin ubiquitylation activity using an $^{35}$S-labeled IVT N-terminal Xenopus cyclin B substrate.

Emi1 interacts with Cdh1 and can block Cdh1-dependent APC activation in vitro. Cdh1 is not present in the early embryo but is present in somatic cells, where it is required to keep the APC active in late mitosis and G1. Interestingly, we found that Emi1 and Cdh1 proteins also interact, both in in vitro binding assays (FIG. 7A) and in the yeast two hybrid system (data not shown). Addition of full-length Emi1 protein prevented Cdh1 from activating APC immunopurified from mitotic egg extract in a dose-dependent fashion in a dose dependent fashion, indicating that Emi1 is able to inhibit both the APC$^{Cdc20}$ and the APC$^{Cdh1}$ (FIG. 7B).

Figure 8A:
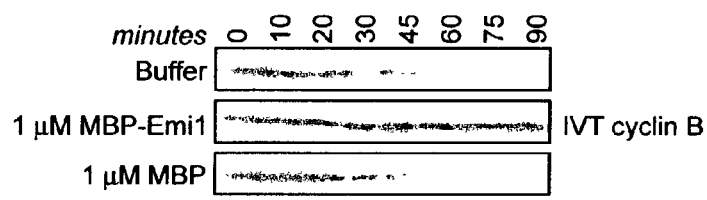
FIG. 8A to 8B shows that human Emi1 is an APC inhibitor and behaves like the Xenopus Emi1 protein. A. Human Emi1 inhibits cyclin B destruction in mitotic extract. $^{35}$S-labeled IVT cyclin B was incubated in Δ90 extracts treated with buffer or 1 µM purified MBP or MBP-Emi1. Aliquots were removed at the indicated times and analyzed by SDS-PAGE and autoradiography. B. Inhibition of Cdh1-mediated activation of the APC by human Emi1. IVT human Cdh1 or rabbit reticulocyte lysate (RLL) was incubated for 30 min with buffer or purified bacterially expressed 1 µM MBP-Emi1, 3 µM MBP-Emi1, 10 µM MBP-Emi1, or 10 µM MBP. APC was immunopurified from interphase egg extracts with anti-Cdc27 beads, then incubated with the Cdh1/protein mixtures for 1 hr. APC beads were washed, and assayed for cyclin ubiquitylation activity using an $^{35}$S-labeled IVT N-terminal Xenopus cyclin B substrate.
Figure 8B:
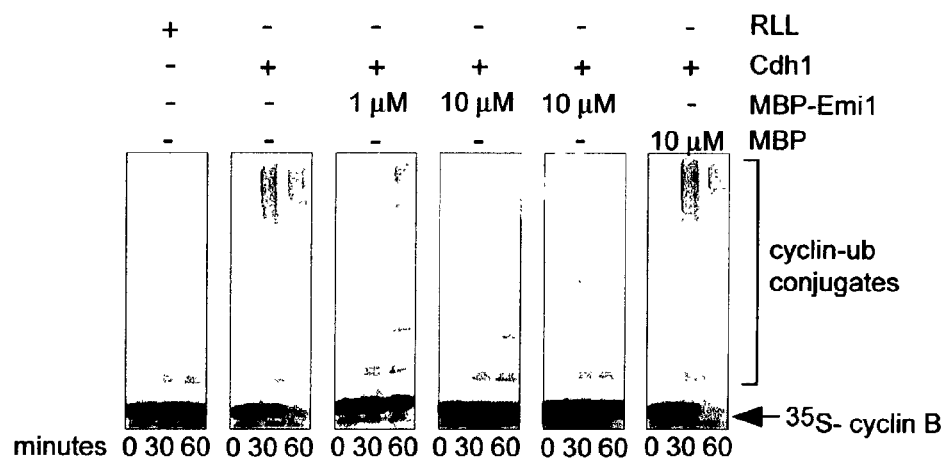

Human Emi1 is an APC inhibitor and behaves similarly to *Xenopus* Emi1. To verify that Human Emi1 protein has the same functions as *Xenopus* Emi1, we tested its activity in several assays. Like the *Xenopus* protein, we found that human Emi1 binds to both Cdc20and Cdh1 and is unstable in mitosis (data not shown). Addtion of human Emi1 protein to mitotic egg extracts prevents destruction of cyclin B (FIG. 8A), and inhibits APC activation by Cdc20 or Cdh1 (FIG. 8B and data not shown.)

Discussion

We have identified a new APC inhibitor called Emi1, which is required for mitotic entry. Emi1 is normally degraded in mitosis and expression of nondestructable versions of the protein or overexpression of the wild type protein causes a mitotic block in embryos and somatic cells. Emi1 destruction is APC-independent in the egg and requires phosphorylation by mitotically active Cdks. Emi1 binds the APC activators Cdc20 and Cdh1; and Emi1 prevents APC activation by Cdc20 or Cdh1, indicating that Cdc20/Cdh1 is the target of Emi1-APC regulation.

Identification of an independent cell cycle oscillator that controls APC activity. Like cyclin B, Emi1 must accumulate for mitotic entry and be destroyed for mitotic exit. Emi1 is destroyed in mitosis by ubiquitin-mediated proteolysis and its destruction apparently requires phosphorylation by mitotic kinases, including cyclin B/Cdc2. Emi1 destruction may be influenced by its association with Cdc20. An interesting possibility is that phosphorylation by cyclin B/Cdc2 triggers the dissociation of Emi1 and Cdc20, thereby promoting Emi1 destruction. Indeed, we found that Cdc20 addition not only rescued the Emi1 block of APC activity, but also stabilized Emi1 in mitotic extracts suggesting that Emi1 is more stable when complexed with Cdc20.

Figure 9:
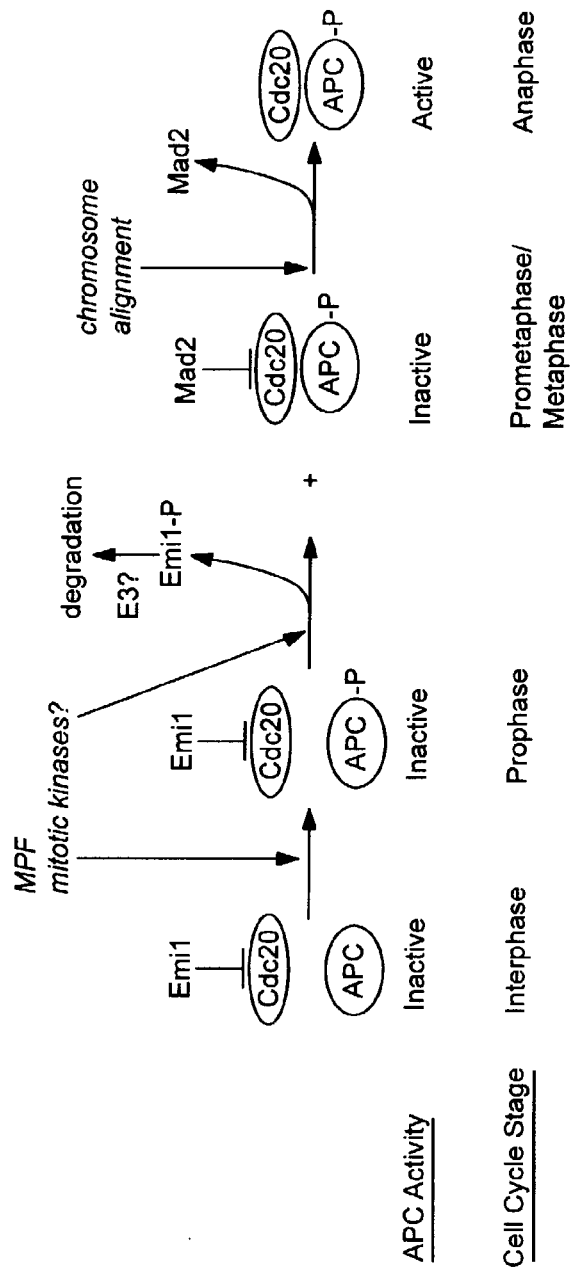
FIG. 9 is a model for Emi1 regulation of the Anaphase Promoting Complex.

Emi1 inhibits the APC$^{Cdc20}$ complex. Cdc20 exists in high molecular weight complexes both with and independent of the APC. Emi1 and Cdc20 co-immunoprecipitate from interphase extracts in a complex independent of the APC, suggesting Emi1 sequesters Cdc20 from the APC (FIG. 9). Our in vitro APC inhibition assays and rescue experiments indicate that Emi1 is a direct Cdc20 inhibitor. The Emi1 zinc-binding region (ZBR) is required to inhibit the APC and binds to Cdc20 in vitro. The ZBR cooperates with the Emi1 N-terminus to bind Cdc20 and may prevent the interaction of Cdc20 with APC substrates. Importantly, Emi1 does not inhibit the substrate and Cdc20-independent ubiquitylation activity of the APC2/APC11 core complex, further indicating that Emi1 inhibits APC activity through Cdc20 and not at the level of the APC enzymatic machinery. Further indicating its specificity, Emi1 does not inhibit SCF ubiquitin-ligase activity in vitro, or SCF-dependent events (DNA replication, mitotic entry) in egg extracts.

Emi1 inhibits the APC$^{Cdh1}$ complex. Emi1 interacts with Cdh1 and our in vitro APC inhibition assay experiments indicate that Emi1 also inhibits APC$^{Cdh1}$. Emi1 thus acts broadly to inhibit the APC, since unlike Mad2, it is able to inhibit both the known APC activators, Cdc20 and Cdh1.

Emi1 as a mitotic timer and potential checkpoint protein for APC activation. Cyclin B ubiquitylation activity of APC immunoprecipitated from synchronized HeLa cells increases significantly before cyclin B levels decrease, and the APC subunit Cdc27 is phosphorylated well before cyclin B levels decrease. This delay in APC activation even when the APC is phosphorylated by MPF suggests the presence of an inhibitor that restrains full APC activation until nuclear envelope breakdown, spindle assembly, and chromatin condensation have occurred. The delay might be explained in part by Mad2, which is required for APC inhibition in prometaphase until chromosomes have been properly aligned at the metaphase plate. However, although anti-Mad2 antibody injection affects progression through metaphase, it does not affect progression through prophase, when MPF is also active and Cdc20 is present.

The observation that Emi1 immunodepletion delays cyclin B accumulation and mitotic entry further indicates that Emi1 inhibits the APC in interphase and in early mitosis, before Mad2 begins to function. Similarly, loss of the likely Emi1 homolog Rca1 prevents mitotic entry in Drosophila embryos. Because APC inhibition by Mad2 or proteasome inhibition by addition of MG132, rescued mitosis in Emi1-depleted extracts, Emi1 most likely affects cyclin B ubiquitylation and destruction, rather than, for example, its translation.

Recent studies indicate APC activation is spatially as well as temporally restricted. Notably, cyclin B proteolysis begins first at the spindle poles and Mad2 activation at kinetochores restrains securin destruction to prevent chromosome segregation. Are there sensing mechanisms other than the SC that regulate the APC? Mitotic events other than kinetochore capture by microtubules, namely chromatin condensation, centrosome separation, nuclear envelope breakdown, and spindle formation must occur sequentially before APC activation. These critical prophase and prometaphase events may be controlled by sensing mechanisms that involve Emi1.

Materials and Methods

Emi1 cloning and yeast two-hybrid screen. A partial cDNA isolated in a Skp1 yeast two-hybrid screen (Regan-Reimann et al., 1999) was used to screen a Xenopus ovary cDNA library (Stratagene). A 1.9 kb clone was sequenced on both strands and contains stop codons upstream of the 5' start codon and a 3' poly-A tail. In vitro translation produces a 44 kDa species in reticulocyte lysate. Emi1-NT (1–193), Emi1-CT (233–392), or Emi1 full-length (fl) were cloned into pAS2 and used to screen (2.5 million clones each) a Xenopus oocyte library (Clontech) in strain Y190. Interacting proteins were verified with fl Emi1 by filter lift β-galactosidase assay.

Preparation of Emi1 full-length and mutant constructs and proteins. Emi1 and variants were cloned into pCS2-5mt (myc-tagged), pMAL or pGEX vectors and Cdc20(1–158) into pCS2 vector. Emi1-pCS2-5mt site-directed mutants [E198A and L199A (EL198AA), S10A, S29A, S105A, T123A, S328A (Emi1-5P), C341S, C346S, C354S and C356S (C354S/C356S), and C364S], were verified by sequencing. Emi1 baculovirus was generated using the BAC-TO-BAC system (Gibco).

Emi1 variants were produced as MBP fusion proteins and purified by standard protocols. Proteins are commonly fused to Escherichia coli maltose-binding protein (MBP) to enhance their yield and facilitate their purification. In addition, the stability and solubility of a passenger protein can often be improved by fusing it to MBP. Human Cdc20 baculovirus protein was as previously described.

Antibody preparation. Bacterially produced MBP-Emi1 was used to raise polyclonal antibodies in rabbits and mice (Josman laboratories). Rabbit antibodies were affinity purified on a GST-Emi1 column.

Binding assays and chromatography. In vitro GST-fusion protein binding reactions were as previously described. In vitro MBP protein binding assays: 100 nM purified MBP-Emi1, MBP-Emi1-NT, MBP-Emi1-CT, or MBP was incubated with 100 nM His-Cdc20 in Buffer 1 (50 mM Tris pH7.5, 100 mM NaCl, 0.1% NP-40), supernatants bound to amylose beads, washed 4× with buffer 2 (50 mM Tris pH7.5, 300 mM NaCl, 1% NP-40), and bound proteins resolved by SDS-PAGE and anti-MBP immunoblots.

Baculovirus reconstitution: SF9 cells co-infected with Emi1 and Cdc20 baculoviruses were lysed in RIPB (100 mM NaCl, 50 mM β-glycerophosphate, 5 mM EDTA, 0.1% triton-X100, 1 mM DTT), and lysates pre-cleared with protein G sepharose. Supernatants were incubated with mouse anti-Emi1 or preimmune (PI) sera, bound to protein G sepharose, washed 4× in RIPB, and analyzed by anti-Cdc20 immunoblots.

Sucrose gradient: Interphase egg extract was diluted 1:5 in buffer (100 mM KOAc, pH7.2; 2.5 mM Mg(OAc)$_2$; 5 mM EGTA; 2 mM DTT; 10 mM Tris pH7.2; 80 mM β-glycerophosphate; 100 mM sucrose), and cleared at 40 k rpm (SW50.1 rotor, 1 hr, 4 C). Lysate was resolved on a 10–40% w/v sucrose gradient, centrifuged in an SW40.1 rotor (30,000 rpm, 18 hr, 4 C), and fractions analyzed by SDS-PAGE and immunoblotting.

High speed interphase Xenopus egg extract supernatants were fractionated on a Resource Q column, and eluted with a 0–0.5 M NaCl gradient. Pooled Emi1-containing fractions were separated on an S-300 gel filtration column. Egg extract or the 100–200 kDa fraction immunoprecipitated with anti-Emi1 or PI sera (as above), were analyzed by anti-Cdc20 or anti-APC2 immunoblot.

Kinase assays. Histone H1 kinase activity and cyclin B kinase activity were analyzed as described. In vitro cyclin B phosphorylation experiments: 1 µM purified MBP-Emi1 or MBP-Emi1 variants were incubated with 2 units cyclin B/Cdc2 (NEB) in kinase buffer plus 66 µM ATP and 0.25 µCi/µl [$^{32}$p]-γATP (15 min, RT), reactions quenched with sample buffer, and resolved by SDS-PAGE.

Xenopus extracts and embryos. Interphase and cycling extracts were made from eggs activated with calcium ionophore A23187. To assay DNA morphology, sperm nuclei were added, fixed at various times, and DNA labeled (Hoechst 33258). Endogenous cyclin A and B levels were assayed by immunoblots with anti-XI cyclin B2 or anti-XI cyclin A1 mouse monoclonal antibodies. Mitotic extracts were made by addition of nondegradable Δ90 sea urchin cyclin B to interphase extracts.

Xenopus eggs were fertilized in vitro, 10 eggs isolated per time point, lysed in RIPB, and assayed for cyclin B-associated kinase activity and Emi1 protein levels by immunoblot. Embryo injection experiments: 9.2 nl of 100 µM protein was injected into one blastomere at the two cell stage. Injected embryos were transferred to 0.1×MMR with 3% Ficoll. H1 kinase activity in injected embryos was assayed as previously described.

Degradation and ubiquitylation assays. Emi1 ubiquitylation: interphase or mitotic extracts were incubated at 23 C for 60 min with 4.6ng/ul FLAG-ubiquitin, 1 µM ubiquitin aldehyde, and 2 mM MG-132. Time points were diluted in RIPB, immunoprecipitated with mouse anti-Emi1 sera or PI sera and analyzed by anti-FLAG (Sigma) immunoblots.

Substrate degradation in Δ90 or cycling extracts: $^{35}$S-labeled IVT protein was added and extracts incubated (23 C). Aliquots were removed, resolved by SDS-PAGE, and quantitated on a Phosphorimager. The cyclin B substrate was an N-terminal sea urchin cyclin B fragment (aa 13-91)-protein A fusion. Extracts were treated with 1 mM Hs cyclin B destruction box peptide or a scrambled version, or depleted of the APC with anti-Cdc27 antisera to assay the effect of APC inhibition on Emi1 stability. To assay Emi1's effect on APC activity, 1 µM MBP fusion protein, 1 µM control protein, or buffer was added.

To assay Emi1's effect on cyclin B ubiquitylation, 2.5 µM MBP-Emi1 or MBP was incubated in Δ90 extracts (20 min), with iodinated sea-urchin cyclin-B fragment as previously described.

In vitro APC assay: Mitotic extract anti-Cdc27 immunoprecipates were incubated (1 hr, 4 C) with IVT hCdc20 preincubated with Emi1, control protein, or buffer, washed in XB-, and assayed for cyclin ubiquitylation, using an $^{35}$S-labeled IVT XI cyclin B1 (aa2-97) fragment as substrate.

Immunodepletions. Anti-Emi1 rabbit polyclonal or PI sera were covalently coupled to protein-A Affiprep beads (Bio-Rad). Beads were washed (20 mM HEPES pH 7.7, 100 mM KCl), incubated with cycling extracts (0.3 ul beads/µl extracts, 45 min, 4 C), and samples cleared (3 min, 3000 rpm, 4 C). The process was repeated 2 more times (30 min, 4 C), and the triple-depleted extracts set to cycle at 23 C. For rescue, depleted extracts were pre-incubated with 0.2 volumes undepleted extract, 300 nM MBP-Emi1, 0.3 µl depletion beads/µl extract, 60 ng/µl Δ90, or 0.3 mg/ml GST-Mad2 (10 min, 4 C) prior to cycling.

Tissue culture, immunofluorescence and flow cytometry. Xenopus XTC cells were maintained as described (Freed et al., 1999). Fugene 6 reagent was used for transfections (Roche Molecular Biochemicals). pEGFP-C1 (Clontech), and myc-Emi1 constructs were co-transfected (1:10). 98% of GFP-positive interphase cells were also myc-labeled. Cells were processed for immunofluorescence or flow cytometry 72 h post-transfection.

Immunofluorescence: cells were grown on cover slips and fixed in methanol (−20° C.) or 2% paraformaldehyde with similar results. Cover slips were washed in Immunofluorescence Wash Buffer (IFWB), and blocked in IFWB with 5% normal donkey serum. 1 Antibodies were: affinity-purified anti-Emi1 (1.5 pg/ml); anti-α-tubulin (Serotec rat anti-α-tubulin mAb, Clone YL1/2 supernatant; 1:1); anti-myc mAb 9E10 (1 µg/ml). Texas Red or fluorescein-conjugated donkey 2 antibodies (Jackson Immunoresearch) were used at 1:150, and Hoechst dye at 5 µg/ml. Fluorescent cells were visualized and digitally imaged or examined by deconvolution microscopy.

Flow cytometric analysis of PI stained cells was performed with a Beckman Coulter ALTRA flow cytometer, using MultiCycle AV software (Phoenix Flow Systems, Inc.)

EXAMPLE 2

The E2F-Dependent Accumulation of hEmi1 Regulates S Phase Entry by Inhibiting APC$^{cdh1}$ It is shown herein that human Emi1 (hEmi1) functions to promote cyclin A accumulation and S phase entry in somatic cells by inhibiting the APC$^{Cdh1}$ complex. At the G1-S transition, hEmi1 is transcriptionally induced by the E2F transcription factor much like cyclin A. hEmi1 overexpression accelerates S phase entry and can override a G1 block caused by overexpression of Cdh1 or the E2F-inhibitor pRb. Depleting cells of hEmi1 through RNA interference prevents accumulation of cyclin A and inhibits S phase entry. These data demonstrate that E2F can activate both transcription of cyclin A and the hEmi1-dependent stabilization of APC$^{Cdh1}$ targets like cyclin A to promote S phase entry.

Figure 10A:
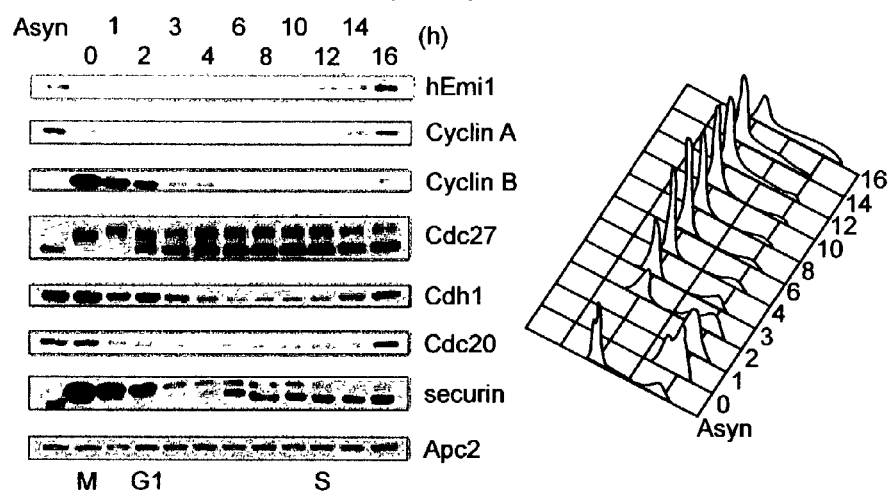
FIGS. 10a–10b. hEmi1 accumulates at the G1-S transition and is destroyed in early mitosis. a, hEmi1 protein is unstable in early mitosis and accumulates at the G1-S transition. Western blots of hEmi1, cyclin A, cyclin B, Cdc27, Cdh1, Cdc20, securin, and Apc2 from HeLa cells released from a nocodazole block (left) and DNA content of the cells at indicated timepoints (right). Asynchronously growing HeLa cells (asyn) were also processed for Western blotting and FACS. b, hEmi1 is stable at the G1-S transition and is destroyed in early mitosis. hEmi1 is stable at a double thymidine block while cyclin A levels are still accumulating. Western blots of proteins from HeLa cells released from a double thymidine block into nocodazole (left) and DNA content of cells at indicated timepoints (right). Asynchronously growing HeLa cells (asyn) were also processed for Western blotting and FACS.
Figure 10B:
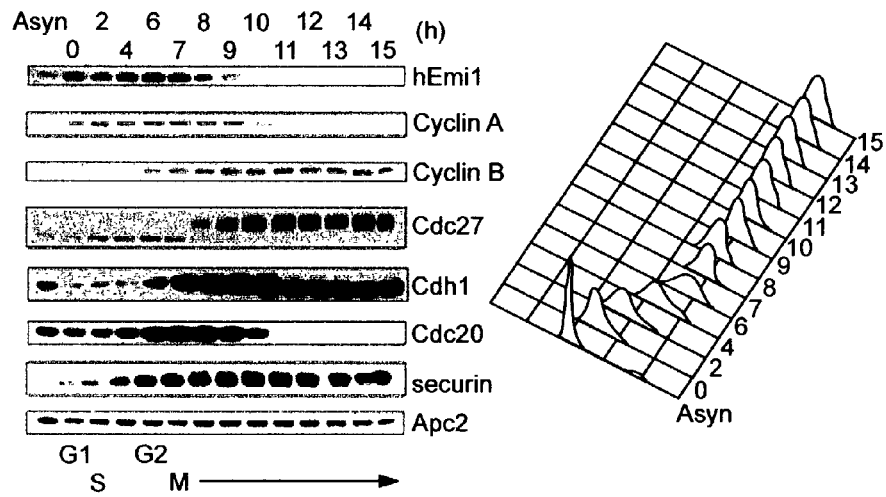

Results hEmi1 has activities similar to the APC$^{Cdc20}$ inhibitor xEmi1. An affinity-purified rabbit polyclonal antibody was generated that recognizes both recombinant and endogenous human Emi1. Human Emi1 has similar properties to the Xenopus Emi1 (xEmi1) in various assays. First, much like xEmi1, hEmi1 localized diffusely in interphase and to the mitotic spindle in early mitosis. Second, overexpression of hEmi1 in human U20S cells caused an accumulation of cells in prometaphase, and a hEmi1 C-terminal fragment (hEmi1-CT) corresponding to the active xEmi1 C-terminal fragment was sufficient for this delay. Microinjection of hEmi1-CT into Xenopus embryos also caused a mitotic block. Third, xEmi1 forms a complex with Cdc20. hEmi1 bound Cdc20 protein in vitro and co-immunoprecipitated endogenous Cdc20 from HeLa lysate. Fourth, hEmi1 protein inhibited cyclin A and cyclin B destruction in Xenopus cycling egg extract and cyclin B ubiquitylation in a reconstituted APC$^{Cdc20}$ ubiquitylation assay. Thus, hEmi1 is similar to xEmi1 in its ability to inhibit APC$^{Cdc20}$.

hEmi1 accumulates in late G1 and is destroyed in early mitosis. To determine when in the somatic cell cycle hEmi1 functions, hEmi1 protein levels were characterized in synchronized human somatic cells. Using various synchronization protocols on human HeLa cells, it was found that hEmi1 protein levels oscillate during the cell cycle, accumulating in late G1 and disappearing in early mitosis. In a nocodazole block, hEmi1 levels were strongly reduced, whereas cyclin B was stabilized by the ability of nocodazole to activate the spindle checkpoint (FIG. 10a). When HeLa cells were released from a nocodazole block, cells exited mitosis and progressed through G1, and hEmi1 levels rose as cells entered S phase. When cells were released from a double thymidine block into nocodazole, hEmi1 was stable through S phase and destroyed in early mitosis (FIG. 10b). This cell cycle profile was similar to that seen for cyclin A protein which is also unstable in the presence of nocodazole and indicate that the destruction of both hEmi1 and cyclin A are independent of the spindle checkpoint. Interestingly, hEmi1 is at maximal levels in the double-thymidine block while cyclin A levels increase several hours after release, suggesting that the hEmi1 protein may accumulate slightly before cyclin A. The destruction of hEmi1 in mitosis agrees with results in *Xenopus* egg extracts showing that in vitro translated human Emi1 is destroyed in mitotic extract. Destruction of xEmi1, and most likely hEmi1, is thought to be APC-independent. Interestingly, Cdh1 levels in both cell cycle treatments do seem to oscillate, as has been previously observed.

hEmi1 is an E2F transcriptional target. The accumulation of hEmi1 at the G1-S transition suggested that hEmi1 might be a target of the transcription factor E2F, a key regulator of the G1-S transition that activates transcription of specific S phase genes including cyclin A. When contact-inhibited human BJ fibroblasts were replated to re-enter the cell cycle, hEmi1 and cyclin A transcript and protein levels coordinately increased as the cells entered S phase. The levels of hEmi1 and cyclin A also increased upon S phase entry following Rb phosphorylation (detected by Western blot using the pRbs$^{795-P}$ phospho-specific antibody), a correlate of E2F activation. To test directly whether E2F activity controls hEmi1 transcription, we used a U2OS cell line inducibly expressing a non-phosphorylatable, constitutively active allele of the retinoblastoma protein (pRb Cdk), which causes transcriptional repression of E2F target genes. hEmi1 transcription was rapidly inactivated upon induction of pRb Cdk. Protein levels of hEmi1 also strongly decreased upon induction of pRb Cdk expression. This effect reflected a loss of hEmi1 mRNA because later addition of the proteasome inhibitor LLnL did not rescue hEmi1 protein levels, indicating that hEmi1 mRNA was no longer present. Thus, the expression profile as well as sensitivity to a potent E2F repressor indicate that hEmi1 belongs to a growing group of genes whose E2F-mediated stimulation at the G1-S transition coordinate S phase entry.

In order to test whether hEmi1 is a direct transcriptional target of E2F, we utilized U2OS cell lines which expressed a chimeric protein of the estrogen receptor fused to either the E2F-1 or E2F-3 transcription factors. Addition of an estrogen analog causes rapid activation of the E2F protein and induction of E2F-dependent transcription. In large-scale comprehensive screens for E2F transcriptional targets through the use of DNA microarrays, several E2F family members were found to upregulate hEmi1 transcription. In order to verify these microarray results, we performed quantitative RT-PCR experiments with these E2F-ER expressing cell lines. Even in the presence of the protein synthesis inhibitor cycloheximide, hEmi1 transcription was increased upon induction of either E2F-3(ER) or E2F-1 (ER). This data argues against the existence of an intermediate factor induced by E2F that is responsible for hEmi1 transcription. Analysis of genomic sequence revealed three potential E2F binding sites less than 500 nucleotides upstream of the transcriptional start site of hEmi1.

hEmi1 associates with Cdh1 and inhibits APC$^{Cdh1}$ in vitro. The APC activators Cdc20 and Cdh1 are highly related proteins. As shown in Example 1, Emi1 is an inhibitor of APC$^{Cdc20}$ in the *Xenopus* embryo, where Cdh1 is not present. xEmi1 also binds and inhibits APC$^{Cdh1}$ activity in a reconstituted *Xenopus* system where purified interphase APC is activated with in vitro translated Cdh1.

To test the model that the accumulation of hEmi1 at the G1-S transition inactivates the APC$^{Cdh1}$ complex to allow stabilization and accumulation of cyclin A, it was tested whether hEmi1 could bind to Cdh1 in vivo and inhibit the APC$^{Cdh1}$ complex in vitro. Transfected hEmi1 and Cdh1 co-immunoprecipitated, whereas a control protein (the cyclin-dependent kinase inhibitor p27$^{Kip1}$) did not co-immunoprecipitate Cdh1. Endogenous Cdh1 also co-immunoprecipitated with hEmi1. In order to test whether hEmi1 associates with Cdh1 at the proper time during the G1-S transition, co-immunoprecipitation experiments were performed from the same synchronized HeLa cells released from a nocodazole block. The amount of endogenous Cdh1 co-immunoprecipitating with hEmi1 increased as cells progressed toward the G1-S transition. In addition, in vitro translated Cdh1 was bound by MBP-hEmi1 but not by MBP alone. Importantly, in vitro ubiquitylation assays using purified, reconstituted APC$^{Cdh1}$ showed that hEmi1 inhibited ubiquitylation of both *Xenopus* cyclin B and human cyclin A in a dose-dependent manner.

hEmi1 rescues accumulation of APC$^{Cdh1}$ substrates in vivo. To determine whether hEmi1 has a positive role at the G1-S transition, it was tested whether hEmi1 overexpression causes an increased S phase fraction. Transient transfection of hEmi1 into human 293T cells induced a strong increase in S phase as compared to cells transfected with vector alone, as well as a slight increase in the G2-M fraction (FIG. 11a). Cotransfection of GFP enabled the sorting of cells into transfected (GFP positive) and non-transfected (GFP negative) populations for Western blot analysis, where it was found that hEmi1 overexpression caused an increase in cyclin A and cyclin B levels, consistent with the ability of Emi1 to promote S phase, where both cyclins are expressed and stable.

Having shown that hEmi1 inhibits APC$^{Cdh1}$ ubiquitylation of cyclin A in vitro, we tested whether the increased S phase population induced by hEmi1 overexpression might be caused by hEmi1 inhibition of APC$^{Cdh1}$ activity in late G1 leading to the subsequent accumulation of cyclin A. The ability of Cdh1 to control cyclin A accumulation and the G1-S transition is supported by the following evidence: 1) cyclin A is required for S phase, and its overexpression accelerates the G1-S transition; 2) Cdh1 overexpression from an inducible line causes a transient G1 arrest, in part by blocking the accumulation of cyclin A; 3) transient overexpression of a constitutively active Cdh1 with its phosphorylation sites mutated to alanine (Cdh1$^{A1a}$), which prevents inactivation by cyclin A/Cdk2, causes an enhanced G1 arrest and more strongly blocks cyclin A and cyclin B accumulation.

Figure 11C:
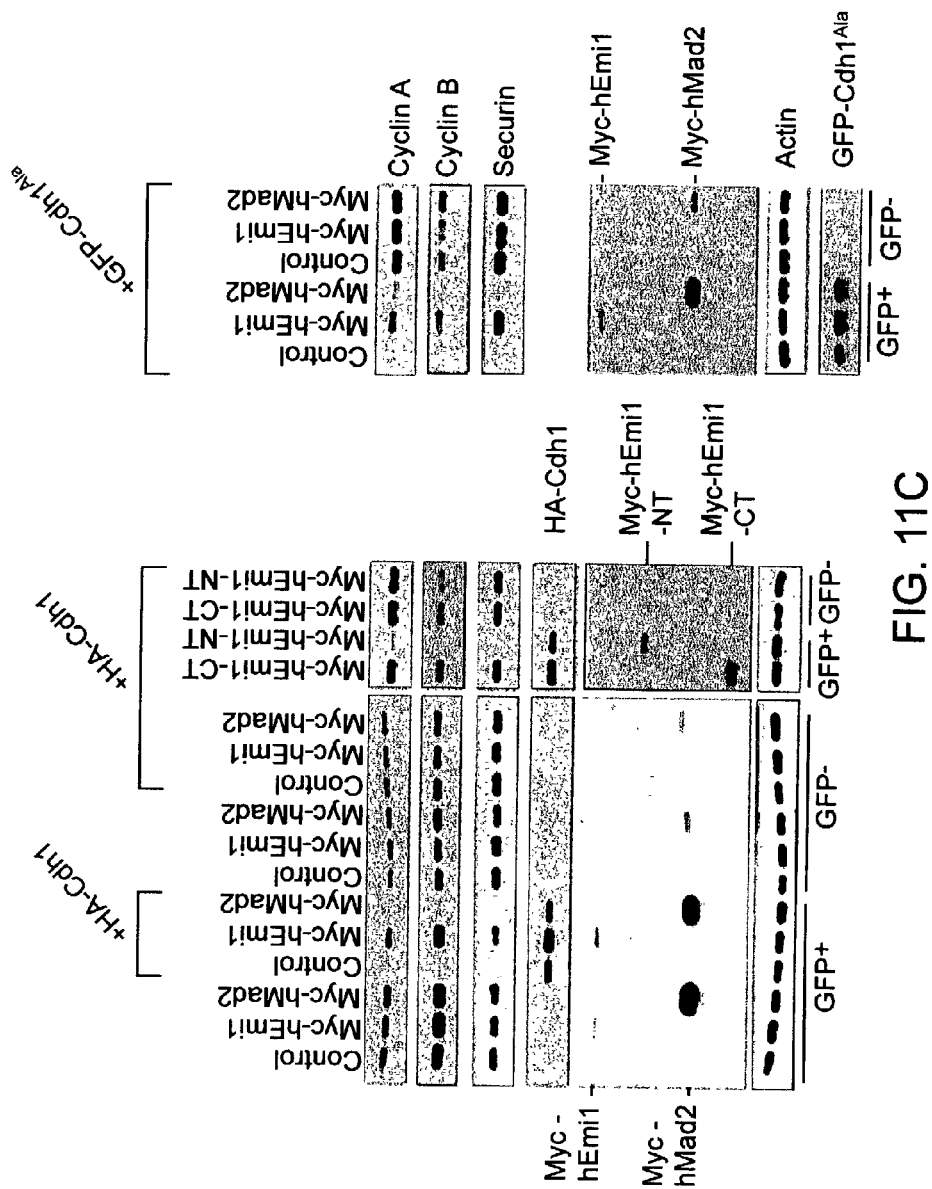

As a test of whether hEmi1 can inhibit Cdh1 in vivo, it was examined whether hEmi1 overexpression could reverse the Cdh1 block to S phase entry. In a cotransfection experiment, hEmi1, but not the APC$^{Cdc20}$ inhibitor Mad2, rescued cells from the Cdh1-induced G1 block (FIG. 11b). Thus, in addition to inhibiting APC$^{Cdc20}$ during mitosis, hEmi1 can inhibit APC$^{Cdh1}$ during late G1 and induce S phase entry. The ability of hEmi1 to drive cells into S phase correlates with the stabilization of APC$^{Cdh1}$ substrates including cyclin A, cyclin B, and securin, a regulator of sister chromatid cohesion (FIG. 11c). The active C-terminal fragment (hEmi1-CT) containing the Cdh1 interacting zinc binding region (ZBR), but not the N-terminal fragment (hEmi1-NT), was sufficient to rescue S phase entry (FIG. 11b,c), consistent with the previous structure-function analysis of xEmi1. Because the hEmi1-CT binds Cdh1 and this interaction is necessary for APC inhibition, the requirement for the hEmi1-CT to reverse the Cdh1 block supports a model of hEmi1 functioning through Cdh1.

Prior results showed that activation of cyclin A/Cdk2 is sufficient to phosphorylate Cdh1 and inactivate $APC^{Cdh1}$ activity. However, if cyclin A is unstable in G1 as a result of $APC^{Cdh1}$ activity, it is unclear how cyclin A could accumulate to inactivate Cdh1. An appealing model is that hEmi1 accumulates first to inactivate $APC^{Cdh1}$, thereby stabilizing cyclin A, and that later cyclin A/Cdk2 phosphorylation provides a second mechanism for Cdh1 inactivation. This model predicts that hEmi1 could inactivate a form of Cdh1 that was resistant to cyclin A/Cdk2 inactivation. o test this idea, hEmi1 was cotransfected with a fusion protein expressing GFP and Cdh1 lacking cyclin/Cdk phosphorylation sites ($Cdh1^{Ala}$). The $Cdh1^{Ala}$ mutant can block cells in G1 more strongly than wild-type Cdh1. Indeed, we found that hEmi1 rescued a G1 arrest induced by the GFP-Cdh1 Ala mutant (FIG. 11b,c).

Figure 11D:
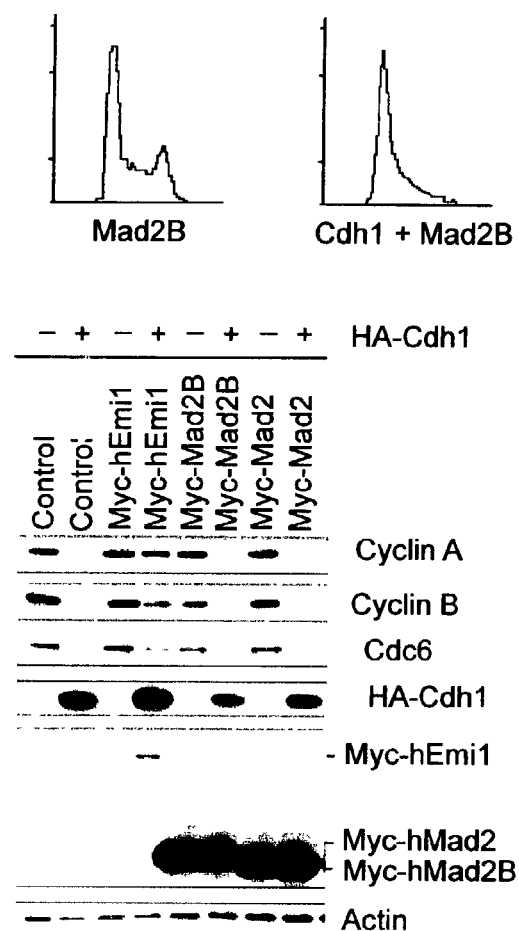

Recent studies have identified Mad2B as a Mad2-related protein that inhibits the $APC^{Cdh1}$ complex. It was tested whether Mad2B is able to rescue the accumulation of $APC^{Cdh1}$ substrates cyclin A and the replication initiation protein Cdc6 when cotransfected with Cdh1. Whereas hEmi1 was able to rescue expression, Mad2B failed to rescue either $APC^{Cdh1}$ substrate accumulation or S phase entry (FIG. 11d). It may be that Mad2B acts on Cdh1 at another time or for another function.

hEmi1 promotes S phase entry. A characteristic of S phase promoting cyclin/Cdk complexes is their ability to overcome a G1 block induced by overexpression of a dominant pRbΔCdk. To test whether hEmi1 can also interfere with the pRbΔCdk G1 block, we transiently transfected U2OS cells with control vector, pRbΔCdk alone, or pRbΔCdk plus various S phase regulators including hEmi1. Nocodazole was added 36 hours post-transfection to trap the cells that had successfully passed the G1 block in mitosis and to prevent their re-entry back into G1. Indeed, it was found that hEmi1 rescued the pRbΔCdk-induced G1 arrest (FIG. 12a) to a very similar extent as that achieved by cyclin A or cyclin E (FIG. 12b). Hence, hEmi1 is the third known gene that can overcome the pRbΔCdk cell cycle arrest.

As a further test of the ability of hEmi1 to affect S phase entry, we microinjected various hEmi1 expression plasmids into rat fibroblasts released from serum starvation. Microinjection of wild-type hEmi1 resulted in an acceleration into S phase as measured by the percentage of BrdU-positive cells (FIG. 12c). In contrast, microinjection of a ZBR mutant hEmi1-C401S did not accelerate S phase, consistent with the importance of the ZBR-Cdh1 interface for the S phase promoting activity of hEmi1. In fact, microinjection of the hEmi1-C401S resulted in a delay in S phase entry. It is possible that the C401S mutant could exert a dominant-negative effect by competing with endogenous hEmi1 for binding $APC^{Cdh1}$ complexes.

Accumulation of cyclin A requires hEmi1. To test whether hEmi1 is required for cyclin A accumulation, hEmi1 was inactivated using small interfering RNAs (siRNAs). Treatment of HeLa cells with siRNA duplexes corresponding to hEmi1 sequence caused a downregulation of hEmi1 protein levels after 24 hours. A corresponding downregulation of cyclin A protein levels was observed. Three out of the four siRNAs (hEmi1 siRNA #1–3) were successful in inactivating hEmi1 expression 24 hours post-transfection. After 24 hours, cells were also analyzed for BrdU incorporation to determine the S phase fraction. The percentage of BrdU-positive cells was decreased in cells treated with hEmi1 siRNA #1–3, but not for hEmi1 siRNA #4 as compared to a control transfection. In order to examine whether decreasing hEmi1 levels might delay the accumulation of cyclin A, HeLa cells were transfected with either control or hEmi1 siRNA four hours prior to an 18 hour nocodazole treatment. Transfection of cells before the nocodazole block allowed sufficient time for the siRNA to reduce hEmi1 levels. Compared to transfection of a control siRNA, transfection of hEmi1 siRNA #1 caused a decrease in hEmi1 levels and a delay in cyclin A accumulation.

Restraining the activity of the anaphase promoting complex is important for preventing premature or improper ubiquitylation and destruction of substrates. Notably, in G1, the $APC^{Cdh1}$ complex prevents accumulation of cyclins A and B. hEmi1 is a potent negative regulator of $APC^{Cdh1}$. hEmi1 accumulates at the G1-S transition at the same time that $APC^{Cdh1}$ is inactivated. In addition, hEmi1 can inhibit Cdh1-dependent ubiquitylation activity in vitro and reverses a Cdh1-induced G1 block to S phase entry in vivo. The ability of Cdh1 to restrain S phase entry may work by inhibiting accumulation of cyclin A, but also by controlling the accumulation of other S phase regulators including $Cdc6^{33}$.

xEmi1 is able to bind and inhibit the ubiquitylation activity of a pre-formed, active $APC^{Cdh1}$ complex, thus suggesting that in late G1 hEmi1 can inhibit an already active $APC^{Cdh1}$. Thereafter, hEmi1 can inhibit $APC^{Cdh1}$ during S and G2 phases before its own destruction in early mitosis. In contrast, the recently described Mad2B protein will not inactivate an already active $APC^{Cdh1}$ complex, suggesting that even though Mad2B can inhibit APC activation by Cdh1 in vitro, it is not as strong a candidate as hEmi1 for the activity that inactivates $APC^{Cdh1}$ at the G1-S transition. The fact that Mad2B is not able to restore accumulation of $APC^{Cdh1}$ substrates like cyclin A and Cdc6 also points to hEmi1 as the critical regulator of $APC^{Cdh1}$ activity at the G1-S transition.

From co-immunoprecipitation experiments, it is calculated that approximately 20–30% of the Cdh1 is co-immunoprecipitating with hEmi1. From sucrose gradient experiments, it is estimated that as much as 75% of Cdh1 co-fractionates with hEmi1. hEmi1 may be able to selectively inhibit ubiquitylation of cyclin A at specific locations such as on chromatin. Chromatin association has been found to be important for ubiquitylation of other proteins, such as Cdk inhibitors.

In G1, an $APC^{Cdh1}$ complex prevents accumulation of substrates such as cyclin A. As cells approach S phase, E2F activates transcription of hEmi1 and cyclin A. hEmi1 initiates the blockade of $APC^{Cdh1}$ ubiquitylation of cyclin A, allowing cyclin A accumulation. Cyclin A activates Cdk2, allowing completion of $APC^{Cdh1}$ inhibition through phosphorylation-dependent dissociation of Cdh1 from the APC. This two-step mechanism allows maximal inhibition of the APC and accumulation of APC substrates important for S phase entry such as cyclin A and the Cdc6 replication factor.

In somatic cells, hEmi1 is a strong S phase promoting factor. It is one of three known genes (including cyclin A and cyclin E) that is able to bypass a G1 block induced by a constitutively active pRb. In contrast, other E2F transcriptional targets such as cyclin D, Cdc6, and various MCMs are unable to overcome the pRbΔcdk-induced G1 block. The function of hEmi1 as an S phase promoting factor is also supported by the observation that microinjection of hEmi1 caused an acceleration of S phase entry and that loss of function of hEmi1 through treatment of cells with siRNA or microinjection of a dominant-negative hEmi1 mutant caused a decrease in cyclin A levels and a delay in S phase entry.

hEmi1 is likely to be a direct transcriptional target of the transcription factors E2F-1 and E2F-3, which are important regulators of the G1-S transition. Recent results with the E2F triple knockout cell line emphasize the importance of E2F-3 for cell proliferation. E2F-3 is the dominant periodic E2F activity in cycling cells. The fact that hEmi1 and cyclin A are both under control of the E2F transcriptional circuit suggests that the E2F-controlled S-phase promoting events include both synthesis and stabilization of critical S phase regulators, notably cyclin A.

The important regulatory role that hEmi1 plays in mitosis in APC$^{Cdc20}$ regulation and in S phase entry suggests that hEmi1 misexpression has deleterious consequences in a variety of human tumors. Indeed, hEmi1 overexpression can cause aberrancies in chromosome segregation, suggesting that hEmi1 overexpression in tumors might contribute to genomic instability by subverting early mitotic events as well as the balance of the S-phase promoting transcriptional program. Recent studies have also implicated a requirement for Cdh1 in G1 cell cycle arrest and the DNA damage-induced G2 checkpoint. Thus, alterations in hEmi1 expression might be expected to affect the level or timing of APC$^{Cdh1}$ activity, leading to genomic instability by several mechanisms.

Because the E2F pathway is activated in highly proliferative cells in tumors, hEmi1 levels are expected to behave similarly, and it is found that hEmi1 transcript levels are elevated in highly proliferative tissues including the thymus, testis, and ovary. hEmi1 transcript and protein levels are also upregulated in a variety of tumors. Examination of hEmi1 mRNA levels in a panel of 250 tumors revealed that 30–40% of tumors of the breast, ovary, uterus, colon, and lung show a substantial increase in expression relative to matched normal tissue (FIG. 13). The central proteins in the Rb/E2F pathway including Rb, p16$^{Ink4a}$, and cyclin D are frequently mutated in cancers, resulting in E2F activation, which we might expect to cause an increase in hEmi1 levels. Highlighting a role for hEmi1 in cancer initiation and progression, a recent large-scale DNA microarray screen of 25,000 genes identified hEmi1 as one of the top 231 genes whose overexpression correlates with estrogen-receptor negative breast tumors and with a poor clinical outcome in breast cancer.

Methods

Antibodies. A bacterially produced MBP-hEmi1-CT (amino acids 299–447) fusion was used to raise polyclonal antibodies in rabbits and mice. Rabbit polyclonal antibodies were affinity-purified with the same C-terminal fragment of hEmi1 fused to GST. For blocking experiments, affinity-purified antibody was pre-incubated with 3 molar excess of MBP-hEmi1-CT antigen. Mouse monoclonal anti-Myc 9E10 antibody and 3F10 antibody rat monoclonal anti-HA antibody (Roche) were used. Other antibodies used were for human cyclin A, cyclin B, human Cdk2, actin, and Cdc20 (Santa Cruz Biotechnology), Cdc27 (Transduction Labs), Apc2 and Cdh1 (Neomarkers), securin (Zymed), phospho-Rb Ser795 (Sigma Israel), and Cdc6 (BioSource International). Mouse monoclonal antibody to Mcm7 was previously described (Sorensen et aL (2000) *Mol Cell Biol* 20, 7613–23). Rabbit polyclonal Cdh1 antibody was from J. Peters (IMP) and *Xenopus* cyclin B2 and cyclin A1 were from T. Hunt (ICRF). Two antibodies were used for Western blot analysis of Cdh1 levels: the affinity-purified rabbit polyclonal antibody and a commercial mouse monoclonal anti-Cdh1 antibody (NeoMarkers DH01). Both antibodies gave the same results, and the mouse monoclonal antibody was also able to co-immunoprecipitate the APC.

Plasmids. Sequences from human and murine Genbank ESTs allowed the design of primers for RACE (rapid amplification of cDNA ends) used to isolate full length Emi1 cDNAs from human prostate and murine testis cDNA libraries (Clontech). Inserts were subcloned into pCS2-Myc$_5$ and pCS2-HA$_3$, pCS2-eGFP-c1 (Clontech), pMAL-c2 (New England Biolabs) and pGEX-4T1 (Pharmacia) vectors. The N-terminal fragment (hEmi1-NT) consists of amino acids 1–244. Site-directed mutagenesis was performed using the Quickchange kit (Stratagene). Wild-type Cdc20 and Cdh1 cDNAs were subcloned into pCS2-Myc$_5$ and pCS2-HA$_3$.

Cell culture. HeLa and 293T cells were grown in DMEM supplemented with 10% fetal bovine serum. HeLa cells were synchronized by a double thymidine block as described and released into medium with or without 330 nM nocodazole (Kramer et al. (2000) *Mol. Cell. Biol.* 11:1555–1569). For the nocodazole release experiments, HeLa cells were blocked with 330 nM nocodazole for 18 h, washed twice in PBS, and released into medium as described in Waizenegger et al. (2000) *Cell* 103:399–410.

At the indicated timepoints, cells were harvested for Western blotting and flow cytometry DNA analysis. Cell pellets were resuspended in RIP-B (Reimann et al. (2001) *Cell* 105:645–655). 25 µg of lysate was loaded onto SDS-PAGE gels, transferred, and probed by various antibodies. For FACS analysis, cells were trypsinized, washed in PBS, and fixed in 70% ethanol overnight. Fixed cells were washed in PBS and stained in 10 ug ml$^{-1}$ RNase A and 20 ug ml$^{-1}$ propidium iodide (PI) for 1 h at 37° C. For GFP/PI staining of cells, cells were first fixed in 0.5% paraformaldehyde for 20 min on ice and washed twice in PBS before the 70% ethanol fixation and treatment with RNase A and propidium iodide. Cells were run on a Coulter ALTRA flow cytometer. Cell cycle analysis software included WinMidi 2.8 and CellQuest Pro.

BJ fibroblasts and U2OS tetracycline-inducible cell lines were passaged and harvested for Northern and Western blots as described (Lukas et al. (1999) *Nature* 401:815–818). U2OS cells stably expressed fusion proteins of the estrogen receptor (ER) with the transcription factors E2F-1 or E2F-3. Experiments involving quantitative reverse-transcriptase polymerase chain reaction (RT-PCR) were performed as described (Muller et al. (2001) *Genes Dev.* 15:267–285). The primer sequences for hEmi1 were as follows: 5'-GTA GAT CGG GAG GAG AGG-3' (forward) and 5'-CAA CTG GCT TTG AGG-3' (reverse).

Microinjections. Serum-starved Rat12 fibroblasts were microinjected by the AIS 2 microinjection unit with expression plasmids for either wild-type Myc-hEmi1 or inactive Myc-hEmi1-C401S mutant at a needle concentration of 100 µg ml$^{-1}$. Immediately after injection, the cells were stimulated to re-enter the cell cycle by 10% fetal calf serum, and the culture medium was supplemented with BrdU. During three consecutive time-points (between 12 h and 20 h to cover the peak of the G1-S transition), cells were fixed, stained for anti-Myc and assayed for BrdU incorporation.

Transfections. 293T cells were transfected with Fugene 6 following the manufacturer's protocol (Roche). Briefly, 293T cells were plated at 2×10$^6$ cells on 10 cm plates the night before transfection. Cells were harvested 24 h after transfection and sorted and processed for GFP/PI staining and for Western blot analysis. Cells were harvested for flow cytometry, immunoblotting, immunofluorescence, and co-immunoprecipitation as described, (Reimann et al., supra.)

For the pRbΔCdk cotransfections, exponentially growing U-2-OS cells were transfected with the indicated plasmids together with CD-20 surface marker. After 36 h, nocodazole (40 ng ml$^{-1}$) was added for additional 12 h into the culture medium. Productively transfected cells were fixed, stained and sorted and their DNA content analyzed by flow cytometry.

RNA interference in mammalian cells. siRNA duplexes were synthesized by Dharmacon. Four duplexes were designed according to hEmi1 sequence. siRNAs duplexes corresponded to nucleotides 567–589 (hEmi1 #1), 182–204 (hEmi1 #2), 401–423 (hEmi1 #3), and 239–261 (hEmi1 #4). A negative control was used which corresponded to green fluorescent protein (GFP). RNA interference was performed as described except that transfection sizes were scaled up to 60 mm dishes (Elbashir et al. (2001) *Nature* 411:494–498). For experiments involving the release from nocodazole, HeLa cells were transfected four hours prior to nocodazole treatment. After an 18 h nocodazole treatment, cells were washed twice in PBS, and released into fresh medium.

Co-immunoprecipitations. Cells were harvested 48 h after transfection. Cell pellets were resuspended in immunoprecipitation (IP) buffer (100 mM NaCl, 50 mM β-glycerophosphate, 5 mM EDTA, 0.1% Triton X-100 at pH 7.2). Lysate was spun out at 14,000 rpm for 15 min at 4° C. Lysate was pre-cleared with Protein G-Sepharose beads (Sigma). 3 μg primary antibody was added to lysate and allowed incubate on ice for 1.5 h. Mouse monoclonal IgG (Jackson Immunoresearch) was used as a negative control. Protein G-Sepharose was added and tubes were rocked for 45 min at 4° C. Immunoprecipitates were washed 4 times in IP buffer and transferred to new tubes. Immunoprecipitates were resuspended in 20 μl 2× protein sample buffer and boiled. Samples were loaded for SDS-PAGE, transferred, and immunoblotted with the appropriate antibodies. For endogenous co-immunoprecipitation experiments, 200 μl of 5 mg ml$^{-1}$ HeLa lysate was pre-cleared by incubating the lysate with 20 μl of Protein G-Sepharose beads for 30 minutes. Lysates were then incubated with 5–10 μl of mouse preimmune or polyclonal anti-hEmi1 antibody for 1.5 h. Next, 20 μl Protein G-Sepharose beads were added and mixed for 40 min. Immunoprecipitates were processed as described for transfected cells.

Proteins. Recombinant MBP-hEmi1 and GST-hEmi1 fusion proteins were constructed by subcloning hEmi1 into the pMAL-c2 (New England Biolabs) and pGEX-4T1 (Pharmacia) vectors, respectively. Recombinant protein was concentrated, dialyzed into XB- (20 mM Hepes pH 7.7 and 50 mM KCl), and flash frozen.

Immunofluorescence. HeLa cells were plated at 1×10$^6$ cells per 10 cm plate containing 22 mm cover slips (Fisher) that were coated with fibronectin (Sigma). The next day, HeLa cells were washed twice in PBS and fixed in ice-cold methanol. For U2OS transfected cells, cells were fixed 3 days post-transfection in 4% ice-cold paraformaldehyde for 30 minutes before proceeding with immunostaining. Cells were washed twice in PBS and twice in IF Buffer (3% BSA, 0.1% Triton X-100 in PBS). Cells were blocked in 5% normal donkey serum (Jackson Immunoresearch) for 40 min. Rat anti-tubulin (1:150, Serotec) and rabbit anti-hEmi1 antibody were incubated with the cells for 1 h. Cells were washed five times in IF buffer. Fluorescently conjugated secondary antibodies (Texas Red donkey anti-rat IgG and fluorescein donkey anti-rabbit IgG; Jackson lmmunoresearch) were added for 45 min. Cell DNA was counterstained by Hoechst stain. Cover slips were mounted with Fluoromount (Southern Biotechnology Associates) and phenylenediamine. Fluorescent cells were visualized with a Zeiss Axioskop microscope using a 63× Neofluor (N.A.=1.3) lens, and photographed using a Princeton Instruments PentaMAX digital camera controlled by computer using Metamorph software (Universal Imaging Corporation).

For BrdU staining, cells were pulsed with 10 uM BrdU (Sigma) for 2 h prior to fixation. Cells on cover slips were fixed in room temperature 70% ethanol for 30 min. The cover slips were rinsed in PBS, incubated in 2 N HCl for 30 min, neutralized in 1×TBE for 5 min, and rinsed in PBS before being treated with the primary antibody mouse monoclonal anti-BrdU (BD Biosciences). Immunofluorescence procedure was followed as above as cells were stained with a Texas Red Donkey anti-Mouse IgG secondary antibody. 400 cells were counted from randomly chosen fields under the microscope and scored for positive BrdU staining.

In vitro binding assays. In vitro translated proteins were centrifuged at 14,000 rpm for 5 min and mixed with equimolar amounts of MBP (0.2 mg) or MBP-hEmi1 (0.5 mg). Proteins were allowed to bind in 20 μl XB- on ice for 1.5 h. The mixture was centrifuged at 14,000 rpm for 10 min. Samples were transferred to new tubes, and the XB- added to a final volume of 100 μl. Next, 40 μl 50% amylose slurry was added and the mixture tumbled for 45 min at 4° C. Samples were washed five times with 200 μl RIP-B, and boiled in 25 μl sample buffer. Samples were run on SDS-PAGE, stained with Coomassie blue, and exposed on a Phosphorimager cassette.

*Xenopus* extract. Experiments involving *Xenopus* extract were performed as previously described (Reimann et al., supra.)

hEmi1 promoter analysis. The hEmi1 mRNA sequence (Genbank AF129535) was searched against human genomic sequence and identified a sequence that included the 5' untranslated region (Genbank AL08276.9). A genomic fragment containing 3 kb of upstream sequence and 1 kb of downstream sequence was inputted to search for transcription factor consensus binding sites using the program TFSEARCH. Highly matched hits (threshold>85.0) corresponding to putative E2F binding sites were found. Decreasing the search threshold did not identify any other E2F binding sites.

Multiple Tissue Northern blots and Cancer Profiling Array. A radioactive probe was generated using a hEmi1 cDNA fragment and was hybridized against two Multiple Tissue Northern blots (Clontech) and a Cancer Profiling Array (Clontech) according to manufacturer's instructions.

EXAMPLE 3

Emi1 is Required for Cytostatic Factor Arrest in Vertebrate Eggs

Vertebrate eggs are arrested at metaphase of meiosis II (MII) with stable cyclin B and high cyclin B/Cdc2 kinase activity. The ability of the anaphase-promoting complex/ cyclosome (APC), an E3 ubiquitin ligase, to trigger cyclin B destruction and metaphase exit is blocked in eggs by the activity of cytostatic factor (CSF). CSF was defined as an activity in mature oocytes that caused mitotic arrest when injected into dividing embryos. Fertilization causes a transient increase in cytoplasmic calcium leading to CSF inactivation, APC activation, cyclin B destruction, and mitotic exit. The APC activator Cdc20 is required for APC activation following fertilization. It is shown herein that the $APC^{Cdc20}$ inhibitor Emi1 is required and sufficient to inhibit the APC and prevent mitotic exit in CSF-arrested eggs. CSF extracts immunodepleted of Emi1 degrade cyclin B and prematurely exit mitosis in the absence of calcium. Addition of Emi1 to these Emi1-depleted extracts blocks premature inactivation of the CSF-arrested state. Emi1 is required to arrest unfertilized eggs at metaphase of meiosis II and is the mediator of CSF activity.

Emi1 is an $APC^{Cdc20}$ inhibitor. In the mitotic cell cycle, Emi1 accumulates before mitosis and binds Cdc20 to inhibit its ability to activate the APC, thus allowing cyclin B to accumulate. In mitosis, Emi is ubiquitylated and destroyed independently of the APC. Microinjection of Emi1 into cleaving embryos causes a CSF-like mitotic arrest. It was tested whether Emi1 is a component of CSF.

Figures 14A, 14B, 14C, 14D:
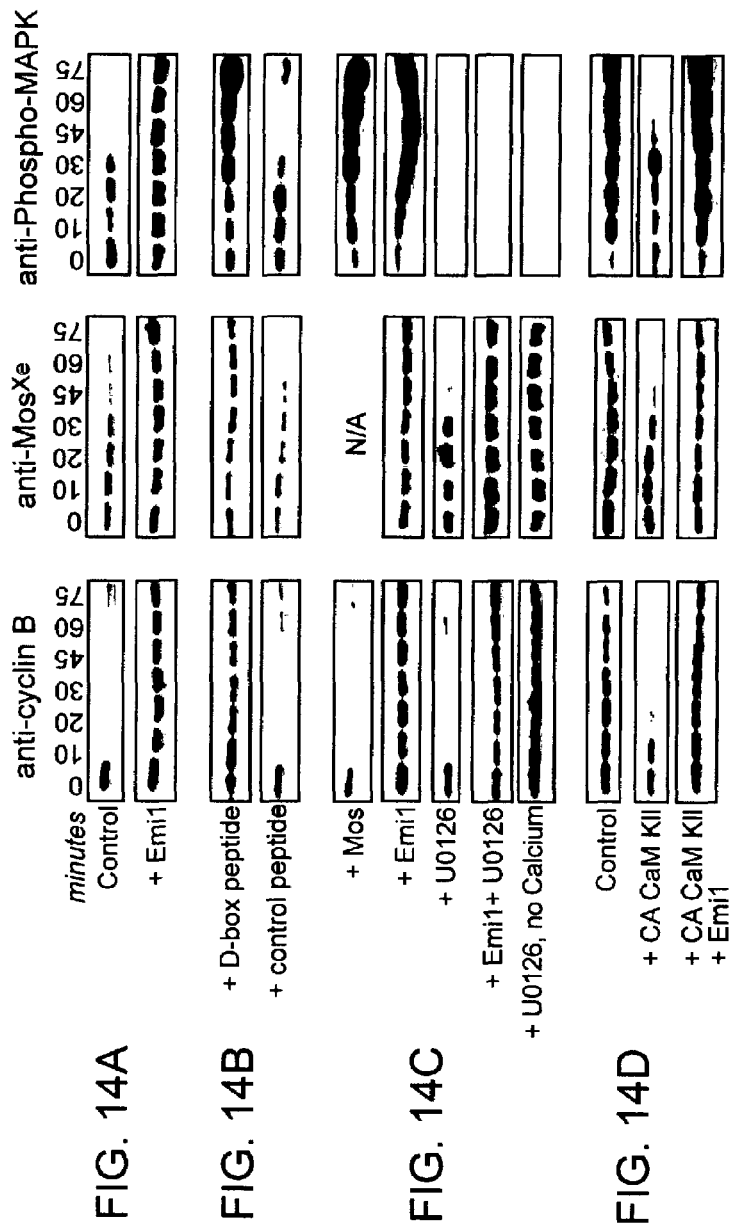

Cyclin B and Mos are stable and MAPK is active in extracts prepared from metaphase of MII-arrested eggs (CSF extracts). In CSF extracts treated with control protein, cyclin B is destroyed, Mos is inactivated and destroyed, and MAPK is inactivated, following calcium addition. Addition of purified MBP-Emi1 protein (1 μM, versus ~300 nM endogenous Emi1) to CSF extracts prevented calcium-induced cyclin B and Mos destruction, and MAPK inactivation (FIG. 14a). Although Mos is not an APC substrate, Mos is stabilized when the APC is inhibited because Mos destruction requires cyclin B/cdc2 inactivation. Examination of DNA morphology revealed that control extracts exited mitosis by 15 minutes, whereas Emi1-treated extracts remained arrested in metaphase>90 minutes. Inhibiting the APC by adding a destruction box (D-box) peptide also blocked CSF release (FIG. 14b). Thus, the APC is required for release from CSF arrest.

Mos inactivation and destruction occur later than cyclin B destruction following either egg activation or calcium addition to CSF extracts (FIG. 14a). Incubation of CSF extracts with Mos protein before calcium addition did not prevent cyclin B destruction even though MAPK remained activated (FIG. 1c), further indicating that Mos inactivation is not required to exit CSF arrest. Addition of the MEK inhibitor U0126 to CSF extracts led to MAPK and $p90^{Rsk}$ inactivation, but did not release extracts from the CSF state (FIG. 14c), consistent with previously reported results on depletion of the MEK target $p90^{Rsk}$ from CSF extracts. These data strongly indicate that the MAPK pathway is not required to maintain CSF arrest.

To test whether Emi1 requires the MAPK pathway to inhibit calcium-induced CSF release, CSF extracts were incubated with U0126 and it was found that Emi1 addition still prevented cyclin B and Mos destruction and mitotic exit in the presence of calcium (FIG. 14c). Thus, Emi1's APC inhibitory activity does not require the MAPK pathway.

Calmodulin-dependent protein kinase II (CaMKII) is required for release from metaphase of MII, and constitutively active (CA) CaMKII is sufficient to trigger cyclin B destruction and mitotic exit without fertilization or calcium addition. Thus, the major calcium-sensitive mediator of CSF release is CaMKII. We found that CA CaMKII did not trigger cyclin B destruction, Mos destruction, or mitotic exit in CSF extracts in the presence of excess Emi1 (FIG. 14d), suggesting that Emi1 acts downstream of CaMKII. These results are consistent with the observation that Cdc20 depletion also prevents CA CaMKII-induced release from CSF arrest. Additionally, much like Cdc20 depletion, excess Emi1 can block okadaic acid-induced cyclin B destruction in CSF extracts in the absence of calcium.

It was examined whether the Emi1 protein accumulates in maturing oocytes in sufficient time to account for CSF arrest. Emi1 is first expressed to significant levels in stage VI G2/prophase oocytes (FIG. 15a). After progesterone addition, Emi1 levels increased by GVBD (germinal vesicle breakdown), similar to Cdc20 (FIG. 15a). Emi1 levels and phosphorylation state did not appear to fluctuate significantly during oocyte maturation, whereas Cdc20 protein levels did (FIG. 15a). In mature oocytes, Emi1 is present in sufficient amounts (~300 nM) to inhibit the endogenous pool of Cdc20 (~40–100 nM).

To test whether Emi1 is required for the maintenance of the MII metaphase arrest, it was examined whether Emi1 depletion caused exit from CSF arrest. Incubation of CSF extracts with magnetic beads precoupled to Emi1 antibodies depleted>80 percent of Emi1 (FIG. 15b). Even though a small amount of Cdc20 coimmunoprecipitated with the anti-Emi1 beads, the majority of Cdc20 (~80%) remained in the extracts (FIG. 15b). As shown in FIG. 2, (c to h), mock-depletion of CSF extracts did not affect cyclin B stability, metaphase arrest or sensitivity to calcium. In contrast, Emi1 depletion reproducibly induced cyclin B destruction and mitotic exit (FIG. 15, c to h). Emi1 depleted extracts also degraded Mos in the absence of calcium.

At time 0 in Emi1-depleted extracts, cyclin B levels were already lower than in mock-depleted extracts (FIG. 15, c and f). Because cyclin B interacts with Emi1, we needed to exclude the possibility that Emi1 depletion caused mitotic exit by co-depleting cyclin B. Only a small amount of cyclin B (~6.3%) was codepleted with Emi1 (FIG. 15b). Moreover, addition of the proteasome inhibitor MG-132 prevented the cyclin B decrease and mitotic exit in Emi1-depleted extracts. Thus, the decrease in cyclin B at time 0 in Emi1-depleted extracts is due to APC activation occurring as Emi1 is depleted.

To verify that the cyclin B destruction and mitotic exit observed in Emi-depleted extracts reflected the loss of Emi1's APC inhibitory function, extracts were preincubated with a stable Emi1 C-terminal fragment that is sufficient to inhibit APC activation in vitro and in vivo. Pre-addition of this purified MBP-Emi1-CT protein rescued cyclin B stability and CSF metaphase arrest (FIG. 15, f to h). Further, addition of purified Emi1 protein to CSF extracts after partial depletion of Emi1 stabilized the remaining cyclin B and prevented mitotic exit. These data strongly indicate that Emi1 is required for the maintenance of CSF arrest in *Xenopus* eggs.

If Emi1 acts in CSF-arrested eggs to inhibit APC activation by Cdc20, then addition of excess Cdc20 might be expected to overwhelm the inhibitory effect of endogenous Emi1, and cause APC activation and mitotic exit. To test this idea, increasing amounts of purified recombinant his-Cdc20 were added to CSF-arrested extracts and it was examined whether these extracts exited CSF arrest in the absence of calcium. Indeed, Cdc20 induced cyclin B degradation and mitotic exit in CSF extracts in a dose-dependent fashion. This effect was blocked by addition of purified MBP-Emi1 protein but not by addition of purified MBP-Mos protein (FIG. 16, a to c).

Cyclin B protein is destroyed by ~10 minutes following egg activation or release of CSF arrest in extracts (FIG. 14). Thus, the activation signal from CaMKII to the APC must be transduced quickly. Emi1 protein levels do not fluctuate significantly until the first mitosis following fertilization, and Cdc20 protein is stable in the early embryo. How, therefore, is Emi1 prevented from inhibiting Cdc20 following fertilization? One possibility is that CaMKII activation leads to a change in binding between Emi1 and Cdc20. To test this idea, we analyzed the binding of endogenous Emi1 and Cdc20 following calcium addition. Emi1 interacts specifically with Cdc20 in vitro and in vivo. Before calcium addition (t=0), Cdc20 coimmunoprecipitated with Emi1. By 2.5 minutes following calcium addition, only background amounts of Cdc20 binding were detectable. A similar loss of binding was seen when $^{35}$S-labeled in vitro translated Cdc20 was added to CSF extracts and coimmunoprecipitated with Emi1 (FIG. 16e).

The mechanism that releases Cdc20 from Emi1 may result from a change in modification in either protein. After calcium addition, we observed a rapid increase in Cdc20 electrophoretic mobility consistent with dephosphorylation (FIG. 16d–e). Alternatively, Emi1 may be a target of CaMKII following its calcium-induced activation. Interestingly, Emi1 contains one consensus, as well as 3 additional less conserved CaMKII phosphorylation sites.

These data demonstrate that Emi1 is essential for the maintenance of CSF metaphase arrest. Unlike the Mos/MAPK pathway, which is not sufficient to maintain CSF arrest, Emi1 is both required and sufficient for metaphase of meiosis II arrest. Thus there appears to be a CSF biochemical pathway that acts to prevent cyclin B/Cdc2 inactivation until fertilization (FIG. 17). The Mos/MAPK pathway acts to keep Cdc2 active through positive regulation and by increasing cyclin B synthesis during the MI-MII transition whereas Emi1 acts to prevent cyclin B destruction through APC inhibition in MII.

Methods

Plasmids and Proteins. Emi1 and Mos constructs were as described in Example 1 and proteins were produced and purified according to standard protocols. To prepare constitutively active (CA) CaMKII, residues 1–290 were subcloned from Rat brain CaMKII α into pCS2 vector.

*Xenopus* extracts and oocytes. *Xenopus* CSF extracts were prepared and 400 μM CaCl$_2$ was used to release extracts from the CSF state. For addition experiments, CSF extracts were pre-incubated (15 min, 4 C) with the indicated reagent. Extracts (+/− calcium addition at t=0) were warmed to 23 C, and equal aliquots taken at the indicated times. For CA CaMKII addition experiments, CSF extracts were preincubated (15 min, 4 C) with buffer or MBP-Emi1 (300 nM). Constitutively active, in vitro translated CaMKII was added (1:14) at time 0, extracts were warmed to 23 C without addition of calcium, and equal aliquots taken at the indicated times. For oocyte maturation experiments, Stage VI oocytes were treated with 5 μg/ml progesterone and equal aliquots collected and lysed over 10 hrs. Cyclin B associated H1 kinase assay was as described in Murray (1991) *Methods in Cell Biology* 36, 581–605 (1991).

Depletion experiments. Affinity purified anti-Emi1 rabbit antibodies (5 μM) or anti-Emi1 mouse polyclonal sera (0.2 μl sera/μl extract) were bound to magnetic protein A-dynabeads or protein G-dynabeads, respectively (Dynal). Beads were washed (20 mM HEPES, pH7.7, 100 mM KCl), incubated with CSF extracts (1 hr, 4 C) and samples cleared of beads with a magnet. The process was repeated twice more (30 min, 4 C) and the triple depleted extracts warmed to 23 C for analysis. Mock-depletions were performed exactly the same, except that purified rabbit IgG (5 μM) or mouse preimmune sera (0.2 μl sera/μl extract) were used instead. For DNA morphology analysis, sperm DNA was added (1000 per μl) and DNA analyzed by Hoechst 33258 staining. MBP-Emi1-CT domain (1 μM) was added for rescue experiments. We performed these Emi1 depletion experiments 10 different times using anti-Emi1 depleting antibodies (1) from several different rabbits, (2) against the full-length and an N-terminal Emi1 fragment, (3) using affinity purified versus crude sera, and (4) using anti-Emi1 sera from several different mice.

Coimmunoprecipitation assays. Calcium (400 μM) was added at time 0 to CSF extracts or CSF extracts preincubated (15 min, 4 C) with $^{35}$S-labeled in vitro translated Cdc20. Extracts were warmed to 23 C, and samples taken at the indicated times after calcium addition and flash frozen. Samples were diluted 1:10 in RIPB buffer, precleared with protein G sepharose, incubated with anti-Emi1 sera (1 hr, 4), bound to protein G sepharose (45 min, 4 C), washed 4× in NETN buffer (20 mM Tris-HCl pH7.5, 150 mM NaCl, 0.5% NP-40, 1 mM dtt, 1 mM EDTA, 1% aprotinin), and bound Cdc20 resolved by SDS-PAGE and immunoblotting or autoradiography.

What is claimed is:

1. A method of inhibiting the anaphase promoting complex (APC) in a proliferating cell, the method comprising:
providing a cell undergoing mitosis with an Emi1 polypeptide;
wherein said providing step comprises introduction of a nucleic acid into said cell, where said nucleic acid comprises the sequence set forth in SEQ ID NO: 3;
wherein said APC activity is inhibited.

2. The method according to claim 1, wherein said inhibiting APC activity results in S phase entry.

3. The method according to claim 1, wherein said Inhibiting APC activity inhibits mitotic progression.

4. The method according to claim 1, wherein said inhibiting APC activity inhibits oocyte activation.

* * * * *

UNITED STATES PATENT AND TRADEMARK OFFICE
CERTIFICATE OF CORRECTION

| | | |
|---|---|---|
| PATENT NO. | : 7,189,569 B2 | Page 1 of 1 |
| APPLICATION NO. | : 10/155789 | |
| DATED | : March 13, 2007 | |
| INVENTOR(S) | : Jackson et al. | |

It is certified that error appears in the above-identified patent and that said Letters Patent is hereby corrected as shown below:

In The Specification Under Column 1:

• Please replace lines 7-10 with:

-- This invention was made with Government support under contracts GM060439 and GM054811 awarded by the National Institutes of Health. The Government has certain rights in this invention. --

Signed and Sealed this
Twelfth Day of April, 2011

David J. Kappos
*Director of the United States Patent and Trademark Office*